(12) United States Patent
Michalowski et al.

(10) Patent No.: US 8,030,475 B2
(45) Date of Patent: *Oct. 4, 2011

(54) INHIBITORS OF RETROVIRAL REVERSE TRANSCRIPTASE

(75) Inventors: Daniel Michalowski, Frederick, MD (US); Donald H. Burke-Aguero, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/471,166

(22) Filed: May 22, 2009

(65) Prior Publication Data

US 2009/0305281 A1     Dec. 10, 2009

Related U.S. Application Data

(60) Provisional application No. 61/128,478, filed on May 22, 2008.

(51) Int. Cl.
C07H 21/04 (2006.01)
C12N 15/00 (2006.01)
(52) U.S. Cl. .................. 536/24.5; 435/320.1
(58) Field of Classification Search .............. 536/23.1; 435/320.1
See application file for complete search history.

(56) References Cited

U.S. PATENT DOCUMENTS

| | | | |
|---|---|---|---|
| 5,503,978 | A | 4/1996 | Schneider et al. |
| 6,323,185 | B1 | 11/2001 | Rondo et al. |
| 2007/0128116 | A1 | 6/2007 | Wang et al. |

OTHER PUBLICATIONS

Abdool Karim, S.S. et al, Global Epidemiology of HIV-AIDS, Infect Dis. Clin. N. Am., 2007, pp. 1-17, vol. 21.
Ambrus, A., et al, Solution Structure of the Biologically Relevant G-Quadruplex Element in the Human c-MYC Promoter. Implications for G-Quadruplex Stabilization, 2005, pp. 2048-2058, vol. 44.
Andreola, M.L., et al, DNA Aptamers Selected against the HIV-1 RNase H Display in Vitro Antiviral Activity, Biochemistry, 2001, pp. 10087-10094, vol. 40.
Arnold, E., et al, Structure of HIV-1 reverse transcriptase/DNA complex at 7 Å resolution showing active site locations, Nature, 1992, pp. 85-87, vol. 357.
Burge, S., et al, Survey and Summary, Quadruplex DNA: sequence, topology and structure, Nucleic Acids Research, 2006, pp. 5402-5415, vol. 34, No. 19.
Chaloin, L., et al, Endogenous expression of a high-affinity pseudoknot RNA aptamer suppresses replication of HIV-1, Nucleic Acids Research, 2002, pp. 4001-4008, vol. 30, No. 18.
Chen, Y., et al, In Vivo Expression of Single-Stranded DNA in Mammalian Cells with DNA Enzyme Sequences Targeted to C-raf, Antisense & Nucleic Acid Drug Development, 2000, pp. 415-422, vol. 10.
Christiansen, J., et al, A guanosine quadruplex and two stable hairpins flank a major cleavage site in insulin-like growth factor II mRNA, Nucleic Acids Research, 1994, pp. 5709-5716, vol. 22, No. 25.
Cogoi, S. and Luigi, E., G-quadruplex formation within the promoter of the KRAS proto-oncogene and its effect on transcription, Nucleic Acids Research, 2006, pp. 2536-2549, vol. 34, No. 9.
Dai, J. et al, Structure of the intramolecular human telomeric G-quadruplex in potassium solution: a novel adenine triple formation, Nucleic Acids Research, 2007, pp. 2440-2450, vol. 35, No. 7.
De Soultrait, V.R., et al, DNA Aptamers Derived from HIV-1 RNase H Inhibitors are Strong Anti-integrase Agents, JMB, 2002, pp. 195-203, vol. 324.
Destefano, J. and Cristofaro, J.V., Selection of primer-template sequences that bind human immunodeficiency virus reverse transcriptase with high affinity, Nucleic Acids Research, 2006, pp. 130-139, vol. 34, No. 1.
Ellington, A.D. and Szostak, J.W., In vitro selection of RNA molecules that bind specific ligands, Nature, 1990, pp. 818-822, vol. 346.
Etzioni, S. et al, Homodimeric MyoD Preferentially Binds Tetraplex Structures of Regulatory Sequences of Muscle-specific Genes, J. Biological Chemistry, 2005, pp. 26805-26812, vol. 280, No. 29.
Fisher, T., et al, HIV-1 reverse transcriptase mutations that confer decreased in vitro susceptibility to anti-RT DNA aptamer RT1t49 confer cross resistance to other anti-RT aptamers but not to standard RT inhibitors, AIDS Research and Therapy, 2005, pp. 8, vol. 2.
Fisher, T., et al, Mutations That Confer Resistance to Template-Analog Inhibitors of Human Immunodeficiency Virus (HIV) Type 1 Reverse Transcriptase Lead to Severe Defects in HIV Replication, Journal of Virology, 2002, pp. 4068-4072, vol. 76, No. 8.
Held, D. M., et al, Differential Susceptibility of HIV-1 Reverse Transcriptase to Inhibition by RNA Aptamers in Enzymatic Reactions Monitoring Specific Steps during Genome Replication, J. Biol. Chem, 2006, pp. 25712-25722, vol. 281, No. 35.
Held, D. M., et al, Cross-Clade Inhibition of Recombinant Human Immunodeficiency Virus Type 1 (HIV-1), HIV-2, and Simian Immunodeficiency Virus SIVcpz Reverse Transcriptases by RNA Pseudoknot Aptamers, J. Virology, 2007, pp. 5375-5384, vol. 81, No. 10.
Hershman, S. G., et al, Genomic distribution and functional analyses of potential G-quadruplex-forming sequences in *Saccharomyces cerevisiae*, Nucleic Acids Research, 2007, pp. 144-156, vol. 36, No. 1.
Huang, H., et al, Structure of a Covalently Trapped Catalytic Complex of HIV-1 Reverse Transcriptase: Implications for Drug Resistance, Science, 1998, pp. 1669-1675, vol. 282. Jacobo-Molina, A., et al, Crystal structure of human immunodeficiency virus type 1 reverse transcriptase complexed with double-stranded DNA at 3.0 Å resolution shows bent DNA, PNAS, 1993, pp. 6320-6324, vol. 90.
Jaeger, J., et al, The structure of HIV-1 reverse transcriptase complexed with an RNA pseudoknot inhibitor, EMBO J., 1998, pp. 4535-4542, vol. 17, No. 15.
Jing, N. et al, Potassium-Induced Loop Conformational Transition of a Potent Anti-HIV Oligonucleotide, J. Biomolecular Structure & Dynamics, 1997, pp. 573-585, vol. 15, No. 3.

(Continued)

*Primary Examiner* — J. E. Angell
(74) *Attorney, Agent, or Firm* — Polsinelli Shughart PC

(57) ABSTRACT

Disclosed are nucleic acid molecules, and methods of their use, which have a specific structure including a double helical domain and a G-quadruplex domain physically connected by a linker domain which may be nucleosidic or non-nucleosidic. These aptamers demonstrate potent inhibition of phylogenetically diverse primate lentiviral reverse transcriptases, which effect is largely independent of aptamer sequence provided that the aptamer has the specified structure.

19 Claims, 21 Drawing Sheets

OTHER PUBLICATIONS

Jing, N., et al, Ion Selective Folding of Loop Domains in a Potent Anti-HIV Oligonucleotide, Biochemistry, 1997, pp. 12498-12505, vol. 36.

Jing, N., et al, Potassium-Dependent Folding: A Key to Intracellular Delivery of G-Quartet Oligonucleotides as HIV Inhibitors, Biochemistry, 2002, pp. 5397-5403, vol. 41.

Jing, N. and Hogan, M.E., Structure-Activity of Tetrad-forming Oligonucleotides as a Potent Anti-HIV Therapeutic Drug, J. Biological Chemistry, 1998, pp. 34992-34999, vol. 273, No. 52.

Jing, N., et al, Stability-Activity Relationships of a Family of G-tetrad Forming Oligonucleotides as Potent HIV Inhibitors, J. Biological Chemistry, 2000, pp. 3421-3430, vol. 275, No. 5.

Joshi, P. and Prasad, V.R., Potent Inhibition of Human Immunodeficiency Virus Type 1 Replication by Template Analog Reverse Transcriptase Inhibitors Derived by SELEX (Systematic Evolution of Ligands by Exponential Enrichment), J. Virology, 2002, pp. 6545-6557, vol. 76, No. 13.

Joshi, P.J., et al, Aptamers Directed to HIV-1 Reverse Transcriptase Display Greater Efficacy over Small Hairpin RNAs Targeted to Viral RNA in Blocking HIV-1 Replication, Molecular Therapy, 2005, pp. 677-686, vol. 11, No. 5.

Kissel, J.D., et al, Single-Stranded DNA Aptamer RT1t49 Inhibits RT Polymerase and RNase H Functions of HIV Type 1, HIV Type 2, and SIV CPZ RTs, Aids Research and Human Retroviruses, 2007, pp. 699-708, vol. 23, No. 5.

Kissel, J.D., et al, Active site binding and sequence requirements for inhibition of HIV-1 reverse transcriptase by the RT1 family of single-stranded DNA aptamers, Nucleic Acids Research, 2007, pp. 5039-5050, vol. 35, No. 15.

Kohlstaedt, J., et al, Crystal Structure at 3.5 Å Resolution of HIV-1 Reverse Transcriptase Complexed with an Inhibitor, Science, 1992, pp. 1783-1790, vol. 256.

Kvaratskhelia, M., et al, Identification of specific HIV-1 reverse transcriptase contacts to the viral RNA:tRNA complex by mass spectrometry and a primary amine selective reagent, PNAS, 2002, pp. 15988-15993, vol. 99, No. 25.

Lyonnais, S., et al, G-Quartets assembly within a G-rich DNA flap. A possible event at the center of the HIV-1 genome, Nucleic Acids Research, 2002, pp. 5276-5283, vol. 30, No. 23.

Macaya, R., et al, Thrombin-binding DNA aptamer forms a unimolecular quadruplex structure in solution, PNAS, 1993, pp. 3745-3749, vol. 90.

Mathews, D.H. et al, Expanded Sequence Dependence of Thermodynamic Parameters Improves Prediction of RNA Secondary Structure, JMB, 1999, pp. 911-940, vol. 288.

Mazumder, A., et al, Inhibition of the Human Immunodeficiency Virus Type 1 Integrase by Guanosine Quartet Structures, Biochemistry, 1996, pp. 13762-13771, vol. 35.

Mosing, R. K., et al, Capillary Electrophoresis—SELEX Selection of Aptamers with Affinity for HIV-1 Reverse Transcriptase, Anal. Chem., 2005, pp. 6107-6112, vol. 77.

Phan, A. T., et al, An interlocked dimeric parallel-stranded DNA quadruplex: A potent inhibitor of HIV-1 integrase, PNAS, 2005, pp. 634-639, vol. 102, No. 3.

Qin, Y., et al, Characterization of the G-quadruplexes in the duplex nuclease hypersensitive element of the PDGF-A promoter and modulation of PDGF-A promoter activity by TMPyP4, Nucleic Acids Research, 2007, pp. 7698-7713, vol. 35, No. 22.

Rachwal, P.A., et al, Effect of G-Tract Length on the Topology and Stability of Intramolecular DNA Quadruplexes, Biochemistry, 2007, pp. 3036-3044, vol. 46.

Rachwal, P.A., et al, Intramolecular DNA quadruplexes with different arrangements of short and long loops, Nucleic Acids Research, 2007, pp. 4214-4222, vol. 35, No. 12.

Risitano, A. and Fox, K. R., Stability of Intramolecular DNA Quadruplexes: Comparison with DNA Duplexes, Biochemistry, 2003, pp. 6507-6513, vol. 42.

Jing, N. et al, Mechanism of Inhibition of HIV-1 Integrase by G-tetrad-forming Oligonucleotides in Vitro, J. Biol. Chem., 2000, pp. 21460-21467, vol. 275, No. 28.

Risitano, A. and Fox, K. R., Influence of loop size on the stability of intramolecular DNA quadruplexes, Nucleic Acids Research, 2004, pp. 2598-2606, vol. 32, No. 8.

Sarafianos, S.G., et al, Crystal structure of HIV-1 reverse transcriptase in complex with a polypurine tract RNA: DNA, EMBO J. 2001, pp. 1449-1461, vol. 20, No. 6.

Schneider, D.J., et al, High-Affinity ssDNA Inhibitors of the Reverse Transcriptase of Type 1 Human Immunodeficiency Virus, Biochemistry, 1995, pp. 9599-9610, vol. 34.

Shafer, R. H. and Smirnov, I., Biological Aspects of DNA/RNA Quadruplexes, Nucleic Acid Sci, 2001, pp. 209-227, vol. 56.

Simonsson, T., G-Quadruplex DNA Structures—Variations on a Theme, Biol. Chem., 2001, pp. 621-628, vol. 382.

Somasunderam, A., et al, Combinatorial Selection, Inhibition and Antiviral Activity of DNA Thioaptamers Targeting the RNase H Domain of HIV-1 Reverse Transcriptase, NIH Public Access, 2005, pp. 10388-10395, vol. 44, No. 30.

Teng, Y., et al, AS1411 Alters the Localization of a Complex Containing Protein Arginine Methyltransferase 5 and Nucleolin, Cancer Res., 2007, pp. 10491-10500, vol. 67, No. 21.

Tohl, J. and Eimer, W., Interaction Energies and Dynamics of Alkali and Alkaline-Earth Cations in Quadruplex-DNA-Structures, J. Mol. Model., 1996, pp. 327-329, vol. 2.

Travascio, P. et al, The Peroxidase Activity of a Hemin-DNA Oligonucleotide Complex: Free Radical Damage to Specific Guanine Bases of the DNA, J. Am. Chem. Soc., 2001, pp. 1337-1348, vol. 123.

Tuerk, C., et al, RNA pseudoknots that inhibit human immunodeficiency virus type 1 reverse transcriptase, PNAS, 1992, pp. 6988-6992, vol. 89.

Tuerk, C. and Gold, L., Systematic Evolution of Ligands by Exponential Enrichment: RNA Ligands to Bacteriophage T4 DNA Polymerase, Science, 1990, pp. 505-510, vol. 249.

Tuske, S. et al, Structures of HIV-1 RT-DNA complexes before and after incorporation of the anti-AIDS drug tenofovir, Nature Structural and Molecular Biology, 2004, pp. 469-474, vol. 11, No. 5.

U.N. Report, HIV Infection on the rise worldwide: UN. Report. Clin. Infect. Dis, 2007, pp. iii-iv, vol. 44.

Zuker, Michael, Mfold web server for nucleic acid folding and hybridization prediction, Nucleic Acids Research, 2003, pp. 3406-3415, vol. 31, No. 13.

Burke, D.H., et al, Bent pseudoknots and novel RNA inhibitors of type 1 human immunodeficiency virus (HIV-1) reverse transcriptase, J. Mol. Biol., 1996, pp. 650-666, vol. 264.

Ulrich, H., et al, DNA & RNA aptamers: from tools for basic research towards therapeutic applications, Comb Chem High Throughput Screen, 2006, pp. 619-632, vol. 9.

Michalowski, D., et al, Novel bimodular DNA aptamers with guanosine quadruplexes inihibit phylogenetically diverse HIV-1 reverse transcriptases, Nucleic Acids Res., 2008, pp. 7124-7135, vol. 36, No. 22.

International Search Report dated Feb. 2, 2010 regarding PCT/US2009/45057, 5 pages.

Purschke, W., et al, An L-RNA-based aquaretic agent that inhibits vasopressin in vivo, PNAS, 2006, pp. 5173-5178, vol. 103, No. 13.

A

| | | | |
|---|---|---|---|
| RT5 | atccgcctgattagcgatact | CAGGGGCCGGGGGGTGGAATACAGTGATCAGCG | acttgagcaaaatcacctgcaggg |
| RT6 | atccgcctgattagcgatact | CAGGGGTTAGGAAGGGGTTGAAAGCAGGTGG | acttgagcaaaatcacctgcaggg |
| RT7 | atccgcctgattagcgatact | CAGGCCTTGGGGGCCGGGACAATGGAGAGATTT | acttgagcaaaatcacctgcaggg |

FIG. 12A

FIG. 13 ed. Recently, non-telomeric quadruplexes have been identified, e.g. in the proto-oncogene c-myc, H-ras, N-ras promoter regions. Thus, quadruplex structures may be a common control element of gene expression. Increasing interest exists in finding and identifying small molecules and naturally occurring proteins that may be control targets of G-quadruplex structures and thus may be candidates for specific therapeutic interventions. The SELEX technique for generating aptamers has been used to generate a few sequence variants that produce variants of the G-quadruplex structure.
INHIBITORS OF RETROVIRAL REVERSE TRANSCRIPTASE

RELATED APPLICATION INFORMATION

This application claims the benefit of U.S. Patent Application Ser. No. 61/128,478, filed May 22, 2008, the disclosure of which is herein incorporated by reference in its entirety.

FEDERALLY SPONSORED RESEARCH OR DEVELOPMENT

This invention was made with government support under grant number AI 62513 by the National Institutes of Health. The government has certain rights in the invention.

INCORPORATION OF SEQUENCE LISTING

The entire contents of a paper copy of the "Sequence Listing" and a computer readable form of the sequence listing on diskette, containing the file named 400090_Updated_SequenceListing_ST25.txt, which is 62 kilobytes in size and was created on Mar. 7, 2011, are herein incorporated by reference.

TECHNICAL FIELD

The present invention relates to the field of oligonucleotide chemistry and more specifically to novel oligonucleotide molecules and their use as anti-viral agents.

BACKGROUND

Aptamers are oligonucleic acid or peptide molecules that are characterized by specific binding to a target molecule. The specific binding underlies the ability of aptamers to act as potent modifiers of protein function. Although they are now known to occur naturally in riboswitches, aptamers as originally described are engineered molecules produced through iterative selection processes drawing from a large random sequence pool. Aptamers are useful in basic research and hold special promise for clinical applications as macromolecular drugs.

A nucelic acid aptamer is essentially a single-stranded oligonucleotide (DNA or RNA), or a series thereof. Selection processes for producing nucleic acid aptamers include a combinatorial technique known as SELEX ("Systematic Evolution of Ligands by Exponential Enrichment"; Tuerk C. & Gold L., SCIENCE (1990), 249 (4968): 505-510), and the process known as in vitro selection in which RNA ligands are selected against various organic dyes (Ellington A. D. & Szostak J. W., NATURE (1990), 346: 818-822). In any case, the resulting aptamers bind tightly and selectively to their ligands and may potentially be employed in targeted molecular therapies.

Certain aptamers and their molecular ligands have been tested for potential therapeutic applications. In particular, the FDA has approved clinical trials for Macugen™ (pegaptinib sodium), an aptamer with application in ophthalmic pathologies. DNA and RNA aptamers also have been generated against HIV-1 proteins to target viral enzymes (Reverse Transcriptase, Protease, Integrase) or viral expression (Rev, Tat), packaging and entry (Gag, nucleocapsid, gp120). For example, certain RNA aptamers against HIV-1 Reverse Transcriptase have been isolated and tested in vitro and in vivo, and some single-stranded DNA aptamers against HIV-1 Reverse Transcriptase have also been described.

A "G-quadruplex" (also known as a G-tetrad or G4-DNA) is a four-stranded nucleic acid structure formed from a sequence that is guanine-rich and thus capable of forming a square arrangement of guanines (a tetrad), which is stabilized by Hoogsteen hydrogen bonding and further stabilized by the existence of a monovalent cation (especially potassium) in the center of the tetrads. A G-quadruplex can be formed of DNA, RNA, LNA and PNA, and may be intramolecular, bimolecular or tetramolecular. Depending on the direction of the strands or parts of a strand that form the tetrads, structures may be described as parallel or antiparallel. Potential quadruplex sequences have been identified in eukaryotic telomeres.

G-rich oligonucleotides (GRO), a novel class of antiproliferative agents, have also been described. The DNA aptamer AGRO100 is an experimental anticancer drug that has entered human clinical trials. It is a non-antisense, guanosine-rich phosphodiester oligodeoxynucleotide that also forms stable G-quadruplex structures. The biological activity of GROs results from their specific binding to specific cellular proteins as aptamers. Nucleolin has is an important target protein of GROs, and is a multifunctional protein expressed at high levels by cancer cells.

Certain DNA oligomers having G-quadruplex structures have been described as inhibitors of certain retroviral functions. For example, the DNA oligomers Zintevir™, 93del, and 112 del are different G-quadruplex aptamers possessing anti-HIV activity. Zintevir™ is a unimolecular 17-mer ODN-derived aptamer (AR177, T30177, and T30695) which prevents the binding of HIV gp120 to CD4 cells and inhibits HIV integrase, and is among the first oligonucleotides to enter human clinical trials. 93 del and 112 del are dimeric DNA G-quadruplex aptamers (shorter DNA aptamers derived from ODN93 and ODN112) originally selected as inhibitors against RNaseH activity).

Thus, the quadruplex structure may be important structural component of new antiviral and ant-cancer drugs, and may be useful in the development of strategies for designing new anti-viral and anti-cancer drugs, particularly for combating the immunodeficiency viruses including HIV-1, HIV-2 and SIV. Consequently, there is a need in the art for methods that allow the identification of aptamers that inhibit proteins that are critical to HIV-1, HIV-2 and SIV replication, as well as specific aptamers that recognize these molecules.

SUMMARY

In one aspect, the present disclosure relates to an isolated nucleic acid molecule comprising a double-helical domain and a G-quadruplex domain coupled by a linker domain.

In another aspect the present disclosure relates to an isolated nucleic acid molecule having a sequence selected from the group consisting of SEQ ID NOS. 15-56 and SEQ ID NOS. 59-63.

In another aspect the present disclosure relates to a method of binding a nucleic acid molecule to a primate lentiviral reverse transcriptase polypeptide comprising combining the nucleic acid molecule and the lentiviral reverse transcriptase polypeptide for a time and under conditions effective to allow the nucleic acid molecule to bind to the lentiviral reverse transcriptase polypeptide such that said binding occurs, wherein the lentiviral reverse transcriptase polypeptide has at least 60% sequence identity with SEQ ID. NO: 1, and the isolated nucleic acid molecule comprises a double-helical domain and a G-quadruplex domain coupled by a linker domain.

In another aspect the present disclosure relates to a method of preparing an isolated nucleic acid molecule that binds a primate lentiviral reverse transcriptase polypeptide, the method including identifying a first nucleotide sequence that provides a double-helical domain, identifying a second nucleotide sequence that provides a G-quadruplex domain, identifying a linker domain; and identifying an aptamer sequence for the isolated nucleic acid molecule that comprises the double helical domain coupled to the G-quadruplex domain by the linker domain.

In another aspect the present disclosure relates to a kit for inhibiting a primate lentiviral reverse transcriptase, the kit comprising at least one nucleic acid molecule as provided above, and written material describing methods for its use to inhibit a primate lentiviral reverse transcriptase.

DETAILED DESCRIPTION

Figure 1:
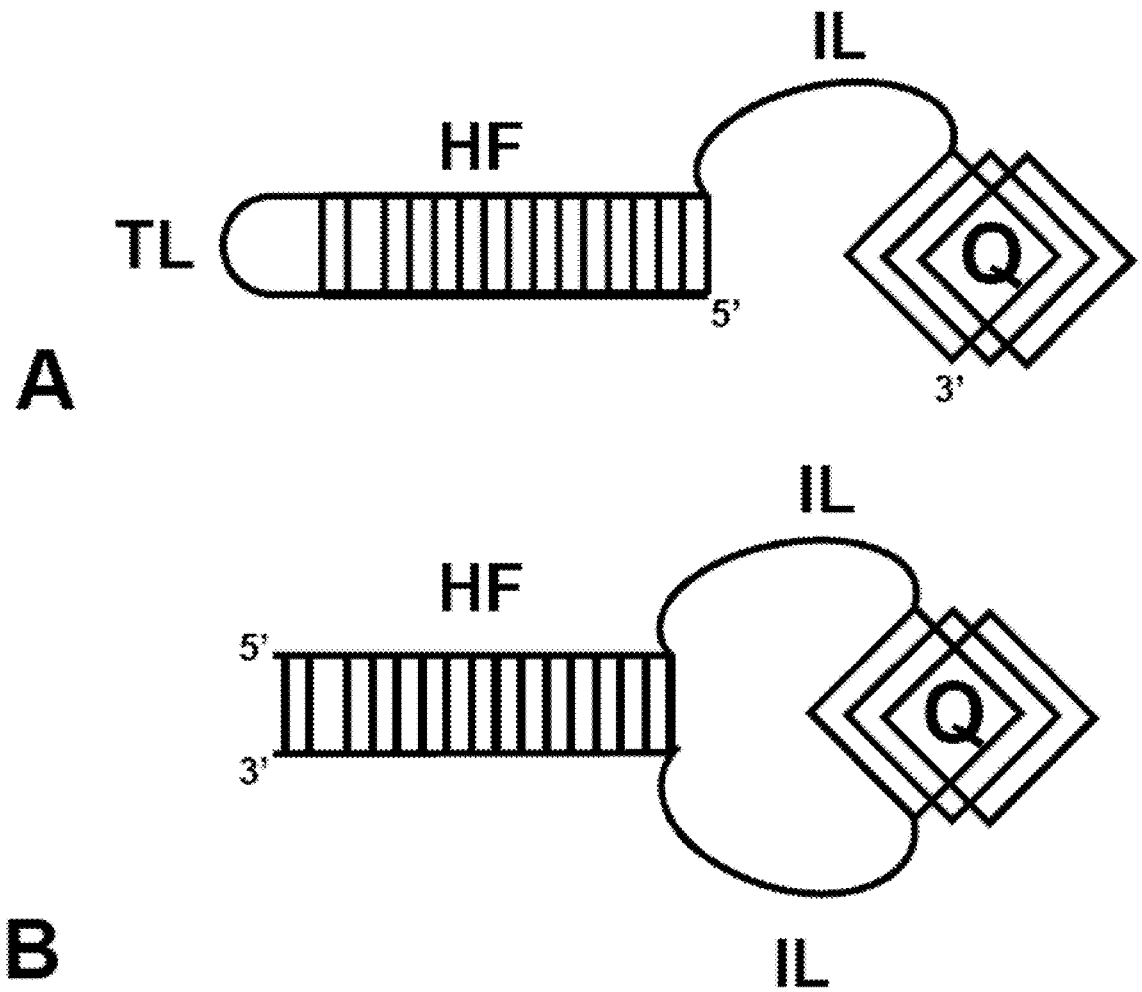
FIG. 1 shows the scheme two variants of the invented inhibitory structure. The difference is in the localization of the terminal ends. Q-quadruplex structure; HF-double helical fragment; IL-inter-module linker/bridge; TL-terminal loop; The quadruplex linkers/loops are not marked.

The present disclosure relates to novel nucleic acid molecules that are characterized by a novel set of structural features and which are strong inhibitors of retroviral Reverse Transcriptase (RT) activity. The nucleic acids of the present disclosure have been found to demonstrate potent inhibition of phylogenetically diverse primate lentiviral reverse transcriptases (RT), including HIV-1 reverse transcriptases. These nucleic acid molecules are characterized in particular by a double helical domain and a guanosine-rich, G-quadruplex domain, wherein these two elements are physically coupled by a linker domain that may be nucleosidic or may be a non-nucleosidic molecule. Surprisingly, the exact nucleotide sequence of the double helical domain and the G-quadruplex domain matters less to the anti-RT activity of the molecule than whether the resulting nucleic acid molecule exhibits the above-specified structural features and other characteristics as further set forth herein below. The present disclosure further provides methods of using the nucleic acid molecules, including in the preparation of nucleic acid molecules that inhibit the activity of primate lentiviral reverse transcriptases.

A. DEFINITIONS

Section headings as used in this section and the entire disclosure herein are not intended to be limiting.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety.

As used herein, the singular forms "a," "an" and "the" include plural referents unless the context clearly dictates otherwise. For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

As used herein, the term "polynucleotide" means any macromolecule that is a polymer of monomeric nucleotides, which is at least 10 bases, or paired bases in length. The nucleotiode bases may be either ribonucleotides or deoxynucleotides or a modified form of either type of nucleotide, including those that display increased thermal stabilities when hybridized to complementary DNAs or RNAs as compared to unmodified DNA:DNA and DNA:RNA pairs. Such modified nucleotides include morpholino and locked nucleic acids (LNAs), peptide nucleic acids (PNAs), 1',5'-anhydrohexitol nucleic acids (HNAs), glycol nucleic acids (GNAs) and threose nucleic acids (TNAs), all of which are characterized by changes to the backbone of the molecule and are capable of folding to form quadruplex structures. The term "polynucleotide" also is meant to encompass single and double stranded forms of nucleotides. As used herein and in the art, the term "polynucleotide" is interchangeable with "oligonucleotide". Polynucleotides that comprise a nucleotide sequence as disclosed herein also encompass those polynucleotides wherein thymidine (T) may be replaced in the sequence by uracil (U), such as when uracil (U) in an RNA sequence replaces thymidine (T) in a corresponding DNA sequence, inasmuch as one of the four major bases in RNA is uracil (U) rather than thymidine (T) as in DNA.

The term "nucleic acid" refers to a macromolecule composed of chains of monomeric nucleotides, which forms a structure that demonstrates a biological function and may also carry genetic information. As is the case with polynucleotides, nucleic acids encompass DNA and RNA in double- and single-stranded forms, and also encompass nucleic acids wherein the bases are a modified form of either type of nucleotide, including LNAs, PNAs, HNAs, GNAs and TNAs. It will be understood that nucleic acids that comprise a nucleotide sequence as disclosed herein also encompass those nucleic acids wherein thymidine (T) may be replaced in the sequence by uracil (U), such as when uracil (U) in an RNA sequence replaces thymidine (T) in a corresponding DNA sequence.

As used herein, the term "polypeptide" means a polymer of at least about 4 to about 10 amino acids. Throughout the specification, standard three letter or single letter designations for amino acids are used. As used herein and in the art, this term is often used interchangeably with "peptide" or "protein".

As used herein, the term "isolated" refers to a molecule that has been identified and separated out from components of the environment in which the molecule is produced, particularly those components of the environment that may interfere with uses for the nucleic acids of the present disclosure. Such components include for example polypeptides, proteins, other polynucleotides, and non-proteinaceous solutes.

As used herein the term "lentiviral reverse transcriptase" encompasses any of a number of known, phylogenetically diverse enzymes all characterized by reverse transcriptase activity, examples of which are provided herein, and including their homodimeric precursors, heterodimeric forms, and any subunit thereof, i.e. either the p66 subunit or the p51 subunit, including any such peptide having at least about 60% sequence identity with SEQ ID NO.: 1 (BH10). The term encompasses for example each of the peptides of SEQ ID NOS. 1-9.

As used herein the term "vector" encompasses any nucleic acid that can drive the expression of a gene incorporated therein, in a cell containing the vector. As used herein the term encompasses for example a circular DNA (plasmid), linear or circular DNA in a package (e.g. in a virus-like adenovirus or AAV), or RNA in a package (e.g. a retrovirus).

As used herein the term "in vitro" refers to activities conducted in cells in a controlled environment. As used herein and in the art, this term is often used interchangeably with "in culture", which may refer to cells in a cell culture or cells in an organ culture.

As used herein the term "in vivo" refers to activities conducted in a whole organism, particularly an animal, for example a mouse, a rat, a cat, a dog, a pig, a sheep, a horse or a human.

As used herein the term "aptamer sequence" refers to the one-dimensional order of a series of monomeric nucleotides, which are covalently linked to from a nucleic acid molecule, wherein the order defines a primary structure of the nucleic acid that includes a double helical domain and a G-quadruplex domain coupled by a linker domain.

As used herein the term "double helical domain" encompasses any polynucleotide having a sequence defining two antiparallel base-paired strands capable of forming helices intertwined about a common axis, without further limitation as to nucleotide sequence, length of the sequence, or localization of terminal ends, including any conformational and structural variants thereof. A double helical domain as used herein encompasses a polynucleotide that forms a hairpin or terminal loop such that a single polynucleotide strand doubles back on itself and forms base parings to form a double helix.

As used herein the term "G-quadruplex domain" refers to any guanosine-rich polynucleotide sequence capable of forming G-tetrads, each of which is a square arrangement of guanines stabilized by Hoogsteen hydrogen bonding, and which may be further stabilized by the presence of a monovalent cation (especially potassium) in the center of the tetrads, without further limitation as to sequence. A G-quadruplex structure may include 2, 3, 4, 5 or more tetrads. A G-quadruplex structure may be formed of DNA, RNA or a modified nucleic acid such as an LNA or a PNA. Resources including algorithms for identifying and predicting sequences which have the capacity to form G-quadruplexes are readily available, for example online and in QUADRUPLEX NUCLEIC ACIDS, Neidle & Balasubramanian (Eds.) 2006.

As used herein the term "linker domain" refers to any nucleosidic or non-nucleosidic molecule that can provide a physical connection between the double helical domain and the G-quadruplex domain, without further limitation as to precise sequence (in the case of a nucleosidic molecule). The linker domain may couple one end of the double helical domain to one end of the G-quadruple domain, or may couple both ends the G-quadruplex domain and both ends of the G-quadruplex domain.

B. LENITVIRAL REVERSE TRANSCRIPTASES

Lentiviral reverse transcriptases (RT's) include several phylogenetically diverse enzymes, or subunits thereof, that were used in functional assays of the nucleic acid molecules described herein. All such RT's have at least about 60% sequence identity with RT from HIV-1 strain BH10 (SEQ ID NO:1) as listed herein below. Typically, testing a nucleic acid molecule of the present disclosure for RT inhibition includes testing the nucleic acid molecule for inhibition of the RT from HIV-1 strain HXB2 (SEQ ID NO: 2) as provided below. However, several different RT's were and can be used in evaluating RT inhibition by nucleic acid molecules according to the present disclosure. All of these demonstrate at least 60% sequence identity with that of the RT from HIV-1 strain BH10. The RT's used and their sequence identity to that from HIV1 strain BH10 are as follows (% sequence identity in complete RT sequences in comparison with HIV-1 strain BH10):

| | |
|---|---|
| HXB2 | 98.9 |
| 94CY pol | 90.4 |
| 92UG021 | 92.9 |
| 93TH253.3 | 90.5 |
| 98CN009 | 92.9 |
| MVP5180 | 78.2 |
| HIV-2 EHO-287 | 60.5 |
| SIVcpzTAN1 | 72.7 |

The amino acid sequence of the RT from strain BH10 is:

```
                                         (SEQ ID NO: 1)
PISPIETVPVKLKPGMDGPKVKQWPLTEEKIKALVEICTEMEKEGKISKI

GPENPYNTPVFAIKKKDSTKWRKLVDFRELNKRTQDFWEVQLGIPHPAGL

KKKKSVTVLDVGDAYFSVPLDEDFRKYTAFTIPSINNETPGIRYQYNVLP

QGWKGSPAIFQSSMTKILEPFKKQNPDIVIYQYMDDLYVGSDLEIGQHRT

KIEELRQHLLRWGLTTPDKKHQKEPPFLWMGYELHPDKWTVQPIVLPEKD

SWTVNDIQKLVGKLNWASQIYPGIKVRQLCKLLRGTKALTEVIPLTEEAE

LELAENREILKEPVHGVYYDPSKDLIAEIQKQGQGQWTYQIYQEPFKNLK

TGKYARMRGAHTNDVKQLTEAVQKITTESIVIWGKTPKFKLPIQKETWET

WWTEYWQATWIPEWEFVNTPPLVKLWYQLEKEPIVGAETFYVDGAANRET

KLGKAGYVTNKGRQKVVPLTNTTNQKTELQAIYLALQDSGLEVNIVTDSQ

YALGIIQAQPDKSESELVNQIIEQLIKKEKVYLAWVPAHKGIGGNEQVDK

LVSAGIRKIL.
```

The amino acid sequence of the RT from strain HXB2 is:

```
                                         (SEQ ID NO: 2)
PISPIETVPVKLKPGMDGPKVKQWPLTEEKIKALVEICTEMEKEGKISKI

GPENPYNTPVFAIKKKDSTKWRKLVDFRELNKRTQDFWEVQLGIPHPAGL

KKKKSVTVLDVGDAYFSVPLDEDFRKYTAFTIPSINNETPGIRYQYNVLP

QGWKGSPAIFQSSMTKILEPFRKQNPDIVIYQYMDDLYVGSDLEIGQHRT

KIEELRQHLLRWGLTTPDKKHQKEPPFLWMGYELHPDKWTVQPIVLPEKD

SWTVNDIQKLVGKLNWASQIYPGIKVRQLCKLLRGTKALTEVIPLTEEAE

LELAENREILKEPVHGVYYDPSKDLIAEIQKQGQGQWTYQIYQEPFKNLK

TGKYARMRGAHTNDVKQLTEAVQKITTESIVIWGKTPKFKLPIQKETWET

WWTEYWQATWIPEWEFVNTPPLVKLWYQLEKEPIVGAETFYVDGAANRET

KLGKAGYVTNRGRQKVVTLTDTTNQKTELQAIYLALQDSGLEVNIVTDSQ

YALGIIQAQPDQSESELVNQIIEQLIKKEKVYLAWVPAHKGIGGNEQVDK

LVSAGIRKVL.
```

The amino acid sequence of the RT from strain 94CY pol is:

```
                                         (SEQ ID NO: 3)
PISPIETVPVKLKPGMDGPKVKQWPLTEEKIKALTEICKEMEKEGKISKI

GPENPYNTPVFAIKKKDSTKWRKLVDFRELNKRTQDFWEVQLGIPHPAGL

KKKKAVTVLDVGDAYFSVPLHEDFRKYTAFTIPSTNNETPGVRYQYNVLP

QGWKGSPAIFQSSMTKILEPFRSKNTELIIYQYMDDLYVGSDLEISQHRV

KIEELRAHLLKWGFYTPDKKHQKEPPFLWMGYELHPDKWTVQPIKLPEKD

SWTVNDIQKLVGKLNWASQIYAGIKVKQLCKLLRGAKALTDIVTLTKEAE

LELEENREILKTPVHGVYYDPSKDLIAEIQKQGQDQWTYQIYQEPFKNLK

TGKYAKRRSTHTNDIKQLTEAVQKITMESIVIWGKTPKFKLPIQKETWET

WWAEYWQATWIPEWEFVNTPPLVKLWYQLEKEPIAGAETFYVDGAANRET

KLGKAGYVTDRGRQKIVSLTETTNQKTELHAIYLALQDSGLEVNIVTDSQ

YALGIIQAQPERSESEIVNQIIEKLIEKERVYLSWVPAHKGIGGNEQVDK

LVSSGIRKVL..
```

The amino acid sequence of the RT from strain 92UG021 is:

```
                                         SEQ ID NO: 4)
PISPIDTVPVKLKPGMDGPKVKQWPLTEEKIKALTEICTEMEKEGKISRI

GPENPYNTPIFAIKKKDSTKWRKLVDFRELNKRTQDFWEVQLGIPHPAGL

KKKKSVTVLDVGDAYFSVPLCEDFRKYTAFTIPSINNETPGIRYQYNVLP

QGWKGSPAIFQSSMTKILDPFRKQNPEMVIYQYMDDLYVGSDLEIGQHRT

KIEELREHLLKWGFTTPDKKHQKEPPFLWMGYELHPDKWTVQPIMLPEKE

SWTVNDIQKLVGKLNWASQIYPGIRVKQLCKCLRGAKALTEVIPLTEEAE

LELAENREILKEPVHGVYYDPSKDLIAEIQKQGQDPWTYQIYQEQYKNLK

TGKYAKTRGTHTNDVKQLTEAVQKIAQECIVIWGKTPKFRLPIQKETWET

WWTEYWQATWVPEWEFVNTPPLVKLWYQLEKEPIVGAETFYVDGAANRET

KLGKAGYVTDKGRQKVVSMTDITNQKAELQAINLALQDSGLEVNIVTDSQ

YALGIIQAQPDKSESELVSQIIEQLIKKEKVYLSWVPAHKGIGGNEQVDK

LVSNGIRKIL.
```

The amino acid sequence of the RT from strain 93TH253.3 is:

```
                                         (SEQ ID NO: 5)
PISPIDTVPVKLKPGMDGPKVKQWPLTEEKIKALTEICKEMEEEGKISKI

GPENPYNTPVFAIKKKDSTKWRKLVDFRELNKRTQDFWEVQLGIPHPAGL

KKKKSVTVLDVGDAYFSVPLDESFRKYTAFTIPSINNETPGIRYQYNVLP

QGWKGSPAIFQSSMTKILEPFRIKNPEMVIYQYMDDLYVGSDLEIGQHRT

KIEELRAHLLSWGFTTPDKKHQKEPPFLWMGYELHPDRWTVQPIELPEKD

SWTVNDIQKLVGKLNWASQIYAGIKVKQLCKLLRGTKALTDIVPLTEEAE

LELEENREILRIPVHGVYYDPSKDLVAEVQKQGQDQWTYQIYQEPFKNLK

TGKYSRKRSAHTNDVRQLTEVVQKIATESIVIWGKTPKFRLPIQRETWET

WWMEYWQATWIPEWEFVNTPPLVKLWYQLEKDPIVGAETFYVDGAASRET

KLGKAGYVTDRGRQKVISLTETTNQKTELHAIHLALQDSGSEVNIVTDSQ

YALGIIQAQPDRSESEVVSQIIEELIKKEKVYLSWVPAHKGIGGNEQVDK

LVISGIRKVL.
```

The amino acid sequence of the RT from strain 98CN009 pol is:

(SEQ ID NO: 6)
PISPIETVPVKLKPGMDGPKVKQWPLTEEKIKALTAICDEMEKEGKITKI
GPENPYNTPIFAIKKKDSTKWRKLVDFRELNKRTQDFWEVQLGIPHPAGL
KRKKSVTVLDVGDAYFSVPLYEDFRKYTAFTIPSTNNETPGIRYQYNVLP
QGWKGSPAIFQSSMTKILEPFRKQNPDIVIYQYMDDLYVGSDLEIGQHRT
KIEELRQHLLRWGFTTPDKKHQKEPPFLWMGYELHPDKWTVQPIQLPEKD
SWTVNDIQKLVGKLNWASQIYPGIKVRQLCKLLRGAKALTDIVPLTEEAE
LELAENREILKEPVHGIYYDPSKDLIAEIQKQGQDQWTYQIYQEPFKNLK
TGKYAKMRTAHTNDVKQLTEAVQKIAMESIVIWGKTPKFRLPIQKETWEI
WWTDYWQATWIPEWEFVNTPPLVKLWYQLEKDPIVGVETFYVDGAANRET
KIGKAGYVTDRGRKKVVSLTETTNQKTELHAICIALQDSGSEVNIVTDSQ
YALGIIQAQPDKSESELVNQIIEQLIKKERVYLSWVPAHKGIGGNEQVDK
LVSSGIRKVL.

The amino acid sequence of the RT from strain HIV-2 EHO-287 pol is:

(SEQ ID NO: 7)
PVARIEPVKVQLKPEKDGPKIRQWPLSKEKILALKEICEKMEKEGQLEEA
PPTNPYNSPTFAIKKKDKNKWRMLIDFRELNKVTQEFTEVQLGIPHPAGL
ASKKRITVLDVGDAYFSVPLDPDFRQYTAFTLPAVNNAEPGKRYLYKVLP
QGWKGSPAIFQYTMAKVLDPFRKANNDVTIIQYMDDILVASDRSDLEHDR
VVSQLKELLNNMGFSTPEEKFQKDPPFKWMGYELWPKKWKLQKIQLPEKE
VWTVNDIQKLVGVLNWAAQLFPGIKTRHICKLIRGKMTLTEEVQWTELAE
AEFQENKIILEQEQEGSYYKEGVPLEATVQKNLANQWTYKIHQGDKILKV
GKYAKVKNTHTNGVRLLAHVVQKIGKEALVIWGEIPMFHLPVERETWDQW
WTDYWQVTWIPEWDFVSTPPLIRLAYNLVKDPLEGVETYYTDGSCNKASK
EGKAGYVTDRGKDKVKPLEQTTNQQAELEAFALALQDSGPQVNIIVDSQY
VMGIVAAQPTETESPIVREIIEEMIKKEKIYVGWVPAHKGLGGNQEVDHL
VSQGIRQIL..

The amino acid sequence of the RT from strain MVP5180 is:

(SEQ ID NO: 8)
PISPIAPVPVKLKPGMDGPKVKQWPLSREKIEALTAICQEMEQEGKISRI
GPENPYNTPIFAIKKKDSTKWRKLVDFRELNKRTQDFWEVQLGIPHPGGL
KQRQSVTVLDVGDAYFSCPLDPDFRKYTAFTIPSVNNETPGVRYQYNVLP
QGWKGSPAIFQSSMTKILDPFRKSNPEVEIYQYIDDLYVGSDLPLAEHRK
RVELLREHLYQWGFTTPDKKHQKEPPFLWMGYELHPDKWTVQPIQLPDKE
VWTVNDIQKLVGKLNWASQIYQGIRVKELCKLIRGTKSLTEVVPLSKEAE
LELEENREKLKEPVHGVYYQPDKDLWVSIQKHGEGQWTYQVYQDEHKNLK
TGKYARQKASHTNDIRQLAEVVQKVSQEAIVIWGKLPKFRLPVTRETWET
WWAEYWQATWIPEWEFVSTPPLIKLWYQLETEPIVGAETFYVDGAANRNT

KLGKAGYVTEQGKQNIIKLEETTNQKAELMAVLIALQDSKEQVNIVTDSQ
YVLGIISSQPTQSDSPIVQQIIEELTKKERVYLTWVPAHKGIGGNEKIDK
LVSKDIRRVL..

The amino acid sequence of the RT from strain SIVcpz-TAN1 is:

(SEQ ID NO: 9)
PISPIEVVKVQLKEGMDGPKVKQWPLSKEKIEALTEICKTLEKEGKISAV
GPENPYNTPIFAIKKKDTSKWRKLVDFRELNKRTQDFWELQLGIPHPAGL
RKRNMVTVLDVGDAYFSIPLDPDFRKYTAFTIPSLNNNTPGKRFQYNVLP
QGWKGSPAIFQSSMTMLDPFRKEHPDVDIYQYMDDLYIGSDLNEEEHRKL
IKKLRQHLLTWGLETPDKKYQEKPPFMWMGYELHPNKWTVQNITLPEPEQ
WTVNHIQKLVGKLNWASQIYHGIKTKELCKLIRGVKGLTEPVEMTREAEL
ELEENKQILKEKVQGAYYDPKLPLQAAIQKQGQGQWTYQIYQEEGKNLKT
GKYAKSPGTHTNEIRQLAGLIQKIGNESIIIWGIVPKFLLPVSKETWSQW
WTDYWQVTWVPEWEFINTPPLIRLWYNLLSDPIPEAETFYVDGAANRDSK
KGRAGYVTNRGRYRSKDLENTTNQQAELWAVDLALKDSGAQVNIVTDSQY
VMGVLQGLPDQSDSPIVEQIIQKLTQKTAIYLAWVPAHKGIGGNEEVDKL
VSKNIRKIL..

RT's can be expressed in *E. coli* and purified as well known in the art and described for example in Held, D., et al., (2006) J. Biol. Chem., 281, 25712-25722.

C. APTAMERS

The present disclosure describes aptamers having a bimodular structure comprising quadruplex and helical domains. Both domains are required for the observed RT inhibition, and they must be physically connected by a linker domain. (See Michalowski, D. et al., (2008) Nucleic Acids Research 36, 7124-7135, which is herein incorporated by reference in its entirety). Relatively few sequence constraints exist within either of the two main domains or in the linkage between them. Moreover, the chemical nature of the linkages between the two major structural elements and within the G-quadruplex plays no significant role in determining inhibition of RT. Importantly, the bimodular aptamer exhibits potent inhibition of RT derived from phylogenetically diverse HIV and SIV strains. These novel nucleic acid molecules are useful for variety of applications, including methods for investigating the mechanism of HIV RT inhibition with structured DNA inhibitors, methods for developing targeted small molecules for therapeutic applications in treating HIV and SIV, and in therapeutic compositions.

The aptamers described herein can be generated based on a set of 81 nt ssDNA aptamers selected to bind HIV-1 RT as described in Schneider, D. J. et al., (1995) Biochem. 34, 9599-9610. Sequences of starting "full-length" aptamers are listed below:

"RT5":

(SEQ ID NO: 10)
TCCGCCTGATTAGCGATACTCAGGCGCCgggGgggTgggAATACAGTGAT

CAGCGACTTGA GCAAAATCACCTGCAgggg.

-continued

"RT47":
(SEQ ID NO: 11)
ATCCGCCTGATTAGCGATACTCAGGCCTTgggCgggCCgggACAATGGAG

AGATTTACTTGA GCAAAATCACCTGCAgggg.

"RT6":
(SEQ ID NO: 12)
ATCCGCCTGATTAGCGATACTCAGGCGTTAgggAAgggCGTCGAAAGCAg ggTgggACTTGA GCAAAATCACCTGCAgggg.

"RT6-A":
(SEQ ID NO: 13)
ATCCGCCTGATTAGCGATACTCAGGCGTTAgggAAgggTAGCGATACAgg gTggg.

"RT6-B" ("Vor"):
(SEQ ID NO: 14)
CGCCTGATTAGCGATACTCAGGCGTTAgggAAgggCGTCGAAAGCAgggT ggg.

Aptamers such as the nucleic acid molecules described herein can be and are derived from the combinatorial method of in vitro selection, or SELEX (for Selective Evolution of Ligands by EXponential enrichment; Tuerk C. & Gold L., SCIENCE (1990), 249 (4968): 505-510). Aptamers having sequences generated according to the teachings of the present disclosure can be commercially synthesized and purified by any of a number of contract laboratories, such as for example, Operon Biotechnologies, Inc., (Huntsville, Ala.), or Integrated DNA Technologies, Inc.

The nucleic acids molecules of the present disclosure have a bi-modular structure consisting of the double helical domain coupled to a guanosine-rich domain forming a G-quadruplex. These two domains are physically coupled by a short, for example (but not limited to) a 2, 3, or 4 nt single stranded fragment, or by another chemical compound(s), such as for example, Sp-C18 (hexaethylene glycol, HEG). In one embodiment, as shown in FIG. 1A, the double helical domain (HF) forms a hairpin, terminal loop and the 3' end of the double helical domain is coupled to a single-stranded linker domain, and the linker domain is coupled to the 5'-end of the G-quadruplex domain. In another embodiment, as shown in FIG. 1B, the 3' end of the double helical domain is coupled to a linker domain first strand, which is coupled to the 5' end of the G-quadruplex domain, and the 5' end of the double helical domain is coupled to a second linker domain strand, which is coupled to the 3' end of the G-quadruplex domain, leaving two free terminal ends of the double helical domain. Nucleic acids having the configuration shown in FIG. 1B appear to be especially structurally plastic and well-suited to various modifications as described herein, such as in drug delivery as carriers, or as therapeutic agents coupled to a carrier or cell-penetrating peptide. Representative nucleic acid molecules having the structure shown in FIG. 1B include those identified as Dyl1 (SEQ ID NO:49), Dyl3 (SEQ ID NO:51), and Dyl5 (SEQ ID NO:52).

Surprisingly, the nucleotide sequence of the nucleic acid molecules is not a primary determining factor for inhibitory activity of these molecules with respect to RT. Provided that the sequence includes a double helical domain and the G-quadruplex domain coupled by a linker domain, such that the sequence is capable of forming these structures, many different and varied sequences are shown to provide the observed inhibitory activity against RT. This holds true for the complete apatmer sequence as well as for the individual domains, particularly the linker domain and the G-quadruplex domain.

That is, neither the exact sequence nor the chemical composition of the nucleic acid used is necessarily limiting of the inhibitory activity of the resulting nucleic acid molecule. For example, within the provisions stated herein, various changes can be made to any of the domain sequences without eliminating inhibition by the molecule of RT. The nucleic acid molecules of the present disclosure also encompass different structural variants of double helical fragments, G-quadruplex structures and different single stranded connectors/linkers/bridges using different 3' and 5' ends in any possible combinations.

Double Helical Domain

The double helical domain encompasses any polynucleotide forming a double helical structure, i.e. a "stem", regardless of length or localization of the 3' and 5' terminal ends. The sequence of the double helical domain is not critical provided only that the sequence allows for the folding needed to from a duplex structure. Preferably the sequence is any sequence that provides at least the thermodynamical stability equivalent of four (4) continuous Watson-Crick base pairs. Exemplary nucleic acids demonstrating a range of sequences suitable for the double helical domain are provided in Tables 2 and 4 below and identified as S1, S2, S4, S5, Dyl1, Dyl2, Dyl3, Dyl5, Acut, and Bcut.

Preferably the double helical domain has a sequence of about 4 to about 20 base pairs in length. However, helical domains of much longer length are also contemplated. In one exemplary embodiment the double helical domain is a sequence of 7, 8, 9 or 10 base pairs in length. In another embodiment the double helical domain is a sequence of 15 base pairs in length. An exemplary double helical domain sequence is CGCCTGA paired with TCAGGCG. The double helical element may include a hairpin, terminal loop. The loop may include a sequence having a length of 1 to 15 bases, in addition to the base-paired portion. In an exemplary embodiment a double helical element includes a hairpin loop having 10 bases. In an exemplary embodiment a double helical element includes a hairpin loop having 7 bases. In an exemplary embodiment a double helical element includes a hairpin loop having 3 bases. The exact sequence of the loop if present is not critical.

The double helical domain may be a DNA, and RNA, or a modified nucleic acid such as a LNA, PNA, GNA, HNA and the like. The double helical domain may also include chemical modifications, different conformations of the helices, and/or additional structural motifs (e.g. a bulge, internal loops, mismatches, etc.). The double helical may be intramolecular, but also may be extended to form an intermolecular duplex, or a hybrid duplex or triplex.

G-Quadruplex Domain

The G-quadruplex domain has a sequence capable of forming at least two layers of G-tetrads that will form a G-quadruplex. In various embodiments the G-quadruplex domain can comprise a sequence capable of forming 2, 3, 4, 5, 6 or more G-tetrad layers, preferably two or three G-tetrad layers. The G-quadruplex domain sequence is guanosine-rich, such as but not limited to a sequence including about 8 to about 24 guanosines as four pairs (gg), triplets (ggg), or quadruplets (gggg), wherein the pairs, triplets or quadruplets are separated by at least one intervening base, which may be any nucleotide base. Alternatively the pairs, triplets or quadruplets may be separated by another intervening molecule, such as HEG.

In an exemplary embodiment the sequence includes 12 guanosines as four triplets. The intervening base is for example any of adenine (A), cytosine (C), or thymidine (T), and may be multiples or combinations thereof. The intervening base(s) may form a loop. In certain embodiments the intervening base is thymidine (T), and the intervening base can be two or more thymidines. In certain embodiments the intervening base is cytosine (C), and the intervening base can be two or more cytosines. In certain embodiments the intervening base is adenine (A), and the intervening base can be two or more adenines. In an exemplary embodiment the G-quadruplex domain has the sequence: gggTgggTgggTggg (SEQ ID NO: 84). In another exemplary embodiment the G-quadruplex domain has the sequence: gggTTgggTTgggT-Tggg (SEQ ID NO: 85). In another exemplary embodiment the G-quadruplex domain has the sequence: gggTTTgggTTTgggTTTggg (SEQ ID NO: 68). In another exemplary embodiment the G-quadruplex domain has the sequence: gggTTTTgggTTTTgggTTTTggg (SEQ ID NO: 86). In another exemplary embodiment the G-quadruplex domain has the sequence: gggTTTTTgggTTTTTgggTTTTTggg (SEQ ID NO: 69). In another exemplary embodiment the G-quadruplex domain has the sequence: gggTTTTTTgggTTTTTTgggTTTTTTggg (SEQ ID NO: 70). In another exemplary embodiment the G-quadruplex domain has the sequence: gggTTTTTTTgggTTTTTTTgggTTTTTTTggg (SEQ ID NO: 71). In another exemplary embodiment the G-quadruplex domain has the sequence: gggTTTTTTTTgggTTTTTTTTgggTTTTTTTTggg (SEQ ID NO: 87). In another exemplary embodiment the G-quadruplex domain has the sequence: gggAgggAgggAggg (SEQ ID NO: 88). In another exemplary embodiment the G-quadruplex domain has the sequence: gggAAgggAAgggAAggg (SEQ ID NO: 89). In another exemplary embodiment the G-quadruplex domain has the sequence: gggAAAgggAAAgggAAAggg (SEQ ID NO: 72). In another exemplary embodiment the G-quadruplex domain has the sequence: gggAAAAgggAAAAgggAAAAggg (SEQ ID NO: 90). In another exemplary embodiment the G-quadruplex domain has the sequence: gggCgggCgggCggg (SEQ ID NO: 93). In another exemplary embodiment the G-quadruplex domain has the sequence: gggCCgggCCgggCCggg (SEQ ID NO: 91). In another exemplary embodiment the G-quadruplex domain has the sequence: gggCCCgggCCCgggCCCggg (SEQ ID NO: 73). In another exemplary embodiment the G-quadruplex domain has the sequence: gggCCCCgggCCCCgggCCCCggg (SEQ ID NO: 92). However, it is not a requirement that the intervening sequences all include the same bases, or same number of bases, and different intervening sequences may include combinations of bases. For example, in another exemplary embodiment the G-quadruplex domain has the sequence: gggAAgggCGTCGAAAG-CAgggTggg (SEQ ID NO: 74). In yet another exemplary embodiment in which the G-pairs, triplets or quadruplets are separated by a non-nucleosidic molecule, the G-quadruplex domain has the sequence: ggg(HEG)ggg(HEG)ggg(HEG)ggg (SEQ ID NO: 83), where HEG indicates hexaethylene glycol. An exemplary formula for the G-quadruplex domain sequence is: $G_nL_nG_nL_nG_nL_nG_n$, where n is >=1 and L is a nucleotide, deoxynucleotide, LNA nucleotide or any chemical compound (propanediol, octanediol, hexaethylene glycol, etc). In one embodiment, the following rule can be used to generate a sequence capable of forming a G-qaudruplex structure:

$G_{3+}L_{1-7}G_{3+}L_{1-7}G_{3+}L_{1-7}G_{3+}$.

Thus it will be understood that a variety of G-rich sequences are capable of providing the G-quadruplex domain. The G-quadruplex domain may also take the form of any one of several recognized structural variants, such as a "chair"-like type, or a "basket"-like type. Other sequences that have the capacity to form G-quadruplexes can be readily identified using any of a number of other G-quadruplex predicting algorithms. As explained above, L may also include any combination of two or more different bases. Further guidance on identifying sequences that form G-quadruplex structures can be found for example in QUADRUPLEX NUCLEIC ACIDS, Neidle & Balasubramanian (Eds.) 2006.

Linker Domain

The linker domain coupling the double helical domain and the G-quadruplex domain can be any nucleosidic or non-nucleosidic molecule having appropriate moities for coupling at least one end of the double helical domain to at least one end of the G-quadruplex domain. The linker domain may be single or double-stranded. For example, the linker domain can be a single-stranded nucleotide sequence of any one of adenine (A), cytosine (C), guanine (G) or thymidine (T), or multiples thereof or a combination thereof. Preferably the linker is no more than about 16 nucleotides or base pairs in length, or if non-nucleosidic, its length equivalent. For example in one embodiment, the linker domain sequence is 1-16 thymidines (T's) in series. In another embodiment the linker domain is 1-16 adenines (A's) in series. In another embodiment the linker domain is 1-16 cytosines (C's) in series. In an exemplary embodiment the linker domain sequence is TT. Alternatively the linker domain may be a non-nucleosidic molecule such as but not limited to SP-C18 (HEG). Linker domains including octanediol, propanediol, and the like are also contemplated.

The linker domain may connect the double helical domain and the G-quadruplex domain to one another using the terminal ends of each domain in any possible combination. FIG. 1 shows two possible configurations that are exemplary of the nucleic acids of the present disclosure. However, other configurations are contemplated provided only that the linker domain provides a physical connection between at least one terminal end of the double helical domain and at least one terminal end of the G-quadruplex domain. A surprising finding is that a nucleic acid according to the present disclosure exhibits strong inhibition of RT regardless of whether the double helical domain or G-quadruplex fragment independently show any such inhibitory activity, whether alone or combined in a mixture but lacking a physical linkage.

The discovery of the basic structural elements of the nucleic acid molecules according to the present disclosure was surprising because the structural elements identified herein were not previously predicted or expected by the starting full-length aptamer sequences. Surprisingly, the novel nucleic acid molecules according to the present disclosure all demonstrated, on a nanomolar scale, strong inhibition of primate lentiviral reverse transcriptase function in vitro. Moreover, RT proteins isolated from different clades and subtypes of HIV-1, HIV-2 and SIV (Held D. M., et. al., J. Virol. (2007), 81(10):5375-5384) were tested, and the inhibitory effects were observed across a phylogenetically diverse group of RT's tested.

Representative DNA aptamers which are nucleic acid molecules according to the present disclosure include all those listed in Tables 1-5 below, except that the apatmers identified as 93del and Stem 93del (SEQ ID NOS: 57 and 58) were used as controls.

TABLE 1

R1T Family

| SEQ ID NO. | Aptamer ID | Sequence |
|---|---|---|
| SEQ ID NO. 15 | R1T | CGCCTGATTAGCGATACTCAGGCGTTgggTgggTgggTggg |
| SEQ ID NO. 16 | R2T | CGCCTGATTAGCGATACTCAGGCGTTgggTTgggTTgggTTggg |
| SEQ ID NO. 17 | R4T | CGCCTGATTAGCGATACTCAGGCGTTgggTTTTgggTTTTgggTTTTggg |
| SEQ ID NO. 18 | R8T | CGCCTGATTAGCGATACTCAGGCGTTgggTTTTTTTTgggTTTTTTTTgggTTTTTTTTggg |
| SEQ ID NO. 19 | R1A | CGCCTGATTAGCGATACTCAGGCGTTgggAgggAgggAggg |
| SEQ ID NO. 20 | R2A | CGCCTGATTAGCGATACTCAGGCGTTgggAAgggAAgggAAggg |
| SEQ ID NO. 21 | R4A | CGCCTGATTAGCGATACTCAGGCGTTgggAAAAgggAAAAgggAAAAggg |
| SEQ ID NO. 22 | R8A | CGCCTGATTAGCGATACTCAGGCGTTgggAAAAAAAAgggAAAAAAAAgggAAAAAAAAggg |
| SEQ ID NO. 23 | R1C | CGCCTGATTAGCGATACTCAGGCGTTgggCgggCgggCggg |
| SEQ ID NO. 24 | R2C | CGCCTGATTAGCGATACTCAGGCGTTgggCCgggCCgggCCggg |
| SEQ ID NO. 25 | R4C | CGCCTGATTAGCGATACTCAGGCGTTgggCCCCgggCCCCgggCCCCggg |
| SEQ ID NO. 26 | SN | CGCCTGATTAGCGATACTCAGGCGTTggg(HEG)ggg(HEG)ggg(HEG)ggg |

TABLE 2

Modifications to Helical domain

| SEQ ID NO. | Aptamer ID | Sequence |
|---|---|---|
| SEQ ID NO. 27 | S1 | CGTGATTAGCGATACTCACGTTgggTgggTgggTggg |
| SEQ ID NO. 28 | S2 | CGGATTAGCGATACTCCGTTgggTgggTgggTggg |
| SEQ ID NO. 29 | S4 | CGCCTGAccctTCAGGCGTTgggTgggTgggTggg |
| SEQ ID NO. 30 | S5 | ATCCGCCTGATTAGCGATACTCAGAAGGATTTgggTgggTgggTggg |
| SEQ ID NO. 31 | ZAM1 | CGCCTGATTAGCGCGCGCCGCGTTTTCGCGGCGCGCGCTACTCAGGCGTTgggTgggTgggTggg |
| SEQ ID NO. 32 | Srevstem | CCGGACTCATAGCGATTAGTCCGGTTgggTgggTgggTggg |

TABLE 3

Mutations establishing a three-tiered quadruplex

| SEQ ID NO. | Aptamer ID | Sequence |
|---|---|---|
| SEQ ID NO. 33 | TQK1 | CGCCTGATTAGCGATACTCAGGCGTTAggTgggTgggTggg |
| SEQ ID NO. 34 | TQK2 | CGCCTGATTAGCGATACTCAGGCGTTgAgTgggTgggTggg |
| SEQ ID NO. 35 | TQK3 | CGCCTGATTAGCGATACTCAGGCGTTggATgggTgggTggg |
| SEQ ID NO. 36 | TQK4 | CGCCTGATTAGCGATACTCAGGCGTTgggTAggTgggTggg |
| SEQ ID NO. 37 | TQK5 | CGCCTGATTAGCGATACTCAGGCGTTgggTgAgTgggTggg |
| SEQ ID NO. 38 | TQK6 | CGCCTGATTAGCGATACTCAGGCGTTgggTggATgggTggg |
| SEQ ID NO. 39 | TQK7 | CGCCTGATTAGCGATACTCAGGCGTTgggTgggTAggTggg |
| SEQ ID NO. 40 | TQK8 | CGCCTGATTAGCGATACTCAGGCGTTgggTgggTgAgTggg |
| SEQ ID NO. 41 | TQK9 | CGCCTGATTAGCGATACTCAGGCGTTgggTgggTggATggg |
| SEQ ID NO. 42 | TQK10 | CGCCTGATTAGCGATACTCAGGCGTTgggTgggTgggTAgg |
| SEQ ID NO. 43 | TQK11 | CGCCTGATTAGCGATACTCAGGCGTTgggTgggTgggTgAg |
| SEQ ID NO. 44 | TQK12 | CGCCTGATTAGCGATACTCAGGCGTTgggTgggTgggTggA |
| SEQ ID NO. 45 | ML2 | CGCCTGATTAGCGATACTCAGGCGTTggTggTggTgg |
| SEQ ID NO. 46 | ML4 | CGCCTGATTAGCGATACTCAGGCGTTggggTggggTggggTgggg |

TABLE 4

Topological variants

| SEQ ID NO. | Aptamer ID | Sequence |
|---|---|---|
| SEQ ID NO. 47 | Stem | CGCCTGATTAGCGATACTCAGGCG |
| SEQ ID NO. 48 | Q16 | TgggTgggTgggTggg |
| SEQ ID NO. 49 | Dy11 | CGCGCTACTCAGGCGTTgggTgggTgggTgggTTCGCCTGATTAGCGCG |
| SEQ ID NO. 50 | Dy12 | CGCGCGCGCTACTCAGGCGTTgggTgggTgggTgggTTCGCCTGATTAGCGCGCGCG |
| SEQ ID NO. 51 | Dy13 | CGCGGCGCGCGCTACTCAGGCGTTgggTgggTgggTgggTTCGCCTGATTAGCGCGCGCCGCG |
| SEQ ID NO: 52 | Dy15 | CGCGCGCGCGCGGCGGCGCGCGCTACTCAGGCGTTgggTgggTgggTgggTTCGCCTGATT AGCGCGCGCCGCCGCGCGCGCGCG |
| SEQ ID NO. 53 | Acut | gggTgggTTCGCCTGATTAGCGATACTCAGGCGTTgggTggg |
| SEQ ID NO. 54 | Acutrev | gggTgggTTGCGGACTCATAGCGATTAGTCCGCTTgggTggg |
| SEQ ID NO. 55 | Bcut | gggTTCGCCTGATTAGCGATACTCAGGCGTTgggTgggTggg |
| SEQ ID NO. 56 | Ecut | gggTgggTgggTTCGCCTGATTAGCGATACTCAGGCGTTggg |
| SEQ ID NO. 57 | 93del | GgggTggGAggAGggT (control) |
| SEQ ID NO. 58 | Stem-93del | CGCCTGATTAGCGATACTCAGGCGTTGggGTggGAggAGggT (control) |

TABLE 5

Intermodule linker variants

| SEQ ID NO. | Aptamer ID | Sequence |
|---|---|---|
| SEQ ID NO. 59 | L3 | CGCCTGATTAGCGATACTCAGGCGTTTTgggTgggTgggTggg |
| SEQ ID NO. 60 | L4 | CGCCTGATTAGCGATACTCAGGCGTTTTTTTTgggTgggTgggTggg |
| SEQ ID NO. 61 | L6 | CGCCTGATTAGCGATACTCAGGCGAAgggTgggTgggTggg |
| SEQ ID NO. 62 | L10 | CGCCTGATTAGCGATACTCAGGCGTTTTTTTTTTTTTTgggTgggTgggTggg |
| SEQ ID NO. 63 | HEG | CGCCTGATTAGCGATACTCAGGCG(HEG)gggTgggTgggTggg | directly or indirectly to the nucleic acid molecule. Such labels include, for example, a radiolabel, a fluorescent probe, an enzyme, oligonucleotide, a nanoparticle, or chemiluminophore. As is well known, in detection methods employing an optical signal, the optical signal can be measured as a concentration dependent change in chemiluminescence, fluorescence, phosphorescence, electrochemiluminescence, ultraviolet absorption, visible absorption, infrared absorption, refraction, and the like. Similarly, in detection methods employing an an electrical signal, the electrical signal is measured as a concentration dependent change in current, resistance, potential, mass to charge ratio, or ion count.

Useful labels according to the present disclosure include for example fluorescent dyes (e.g., fluorescein, Texas Red, rhodamine, green fluorescent protein) and the like (see, e.g., Molecular Probes, Eugene, Oreg., USA), and radiolabels (e.g., 3H, 125I, 35S, 14C, or 32P), and catalysts such as enzymes (e.g., horse radish peroxidase, alkaline phosphatase, beta-galactosidase and others).

Alternatively, the nucleic acid can be coupled or conjugated to another molecule or molecules with other useful functions. For example, the nucleic acid may be advantageously coupled to a polypeptide, such as a carrier peptide or a cell-penetrating polypeptide. Such peptides can be useful in delivering the nucleic acids to cells to provide inhibition of RT.

Peptide carriers are increasingly well known and have been described for use in the delivery of anti-tumoral, anti-viral or antibiotic drugs, which otherwise cannot cross the cell membrane. Peptide carriers, particularly in the present context, are useful because they are readily synthesized and modified and therefore readily adapted for attaching cargo consisting of small molecules. The ability of a wide variety of short peptides to act as carriers for the delivery of oligonucleotides into a cell has been demonstrated. Examples include human calcitonin (hCT), fragments of transduction proteins domains such as VP22, Tat (HIV transactivator of transcription), Antennapedia (Antp), MPG peptide (N-methylpurine DNA glycosylase, or 3-methyladenine; "3MeA"), Pep1, arginine-rich peptides, β-peptides, peptoids and loligomers (branched peptides rich in Lys). All these cell penetrating peptides have proven to be valuable in the delivery of biologically active cargoes to the cytoplasm and nucleus.

Typically a complex of a nucleic acid molecule with a cell-penetrating peptide is formed through covalent bonding. Such complexes have been synthesized using either stable or cleavable linkages. A common method is to form cleavable disulfide linkages through total stepwise solid-phase synthesis or solution-phase or solid-phase fragment coupling. Other linking strategies include forming stable amide, thiazolidine,

D. COMPOSITIONS INCLUDING DETECTABLE LABELS AND OTHER MOLECULES

The nucleic acid molecules according to the present disclosure may be coupled with other molecules for use in a variety of applications. For example, the nucleic acid molecules may be labeled with a detectable label. Alternatively, the nucleic acid molecules may be coupled to a peptide, such as a carrier peptide or a cell-penetrating polypeptide. As is well known, nucleic acids are especially well-suited to chemical modifications of many kinds.

Detectable labels suitable for such use include any compound or composition having a moiety that is detectable by spectroscopic, photochemical, biochemical, immunochemical, electrical, optical, or chemical means, and can be coupled oxime and hydrazine linkages. Newer, non-covalent linking strategies using either electrostatic or hydrophobic interactions can avoid the need for chemical modification. This approach may be preferred to maintain full biological activity.

E. PHARMACEUTICAL COMPOSITIONS

A nucleic acid molecule of the present disclosure can be contained within a pharmaceutical composition, for example together with a pharmaceutical carrier, excipient or stabilizer. The present disclosure also relates to drug-carrier complexes and to the use of the nucleic acids in drug-carrier complexes used as pharmaceutical compositions to deliver specific drugs in cells, tissues and organisms. In particular such compositions can be useful in antiviral therapies directed against a primate lentivirus such as HIV1, HIV-2 and SIV. Methods for systemic delivery of such compositions include typical routes of administration, as well as intracellular production of ssDNA and RNA. Methods for local delivery include delivery into cells by lipid-DNA complexes and the like, as further described in the art (see e.g., Chen Y., et al., Antisense & Nucleic Acid Drug Development (2000), 10:415-420; and Jing N., et al., Biochemistry (2002), 41:5397-5403).

The present disclosure provides methods for modulating RT activity in mammalian cells, wherein the method includes exposing the cells to an amount of the anti-RT aptamer sufficient to inhibit RT activity in the cells. Preferably, the amount of anti-RT aptamer employed will be an amount effective to reduce or eliminate the activity of RT so to achieve a therapeutic effect. This can be accomplished in vivo or ex vivo in accordance, for instance, with the methods described below. Exemplary conditions or disorders to be treated with anti-RT aptamers include infection with HIV-1, HIV-2 or SIV. In particular, the molecules described herein are useful in treating various pathological conditions associated with HIV-1, HIV-2 or SIV infection. Such conditions can be treated by modulating a selected activity associated with RT activity in a mammal through, for example, administration of one or more anti-RT aptamers as described herein.

The anti-RT aptamers can be administered by known routes of administration including intravenous administration, intramuscular, intraperitoneal, intracerebrospinal, subcutaneous, intra-articular, intrasynovial, intrathecal, oral, topical, or inhalation routes. Effective dosages and schedules for administering antagonists or agonists are determined empirically according to guidelines generally recognized by those of skill in the art. Single or multiple dosages may be employed.

As noted above, the anti-RT aptamers useful in the methods of the present disclosure can be incorporated into pharmaceutical compositions suitable for administration into an animal such as a mammal. Methods for formulating such compositions are generally well known. Guidance is available for example from Remington: THE SCIENCE AND PRACTICE OF PHARMACY, 19th Edition, Gennaro (ed.) 1995, Mack Publishing Company, Easton, Pa. Such compositions typically comprise at least one anti-RT aptamer and a pharmaceutically acceptable carrier. The term "pharmaceutically acceptable carrier" refers to any and all coatings, excipients, solvents, dispersion media, absorption delaying agents, and the like, compatible with pharmaceutical administration. Such carriers also include for example sodium chloride, colloidal silica, talc, various polymeric carriers including polyvinyl pyrrolidone, cellulose-based compounds such as carboxymethylcellulose or methylcellulose, polyvinylpyrrolidone, polyacrylates, and polyethylene glycol.

Dosage forms include, for example, oral or sublingual tablets, pellets, micro- and nano-capsules, liposomes, inhalation forms, nasal sprays, and sustained-release preparations.

Pharmaceutical compositions of the present disclosure, comprising anti-RT aptamers, are administered in therapeutically effective amounts. As used herein, the term "therapeutically effective amount" refers to a nontoxic dosage level sufficient to induce a targeted biological effect (e.g. a diminution of the severity of the symptoms associated with a pathological condition such as breast or ovarian cancer). Amounts for administration may vary depending on the current condition of the animal being treated, the selected dosage form and route of administration, and other patient-specific factors such as age, gender and cooperativeness. A therapeutically effective amount may be provided in a broad range of amounts. Such amounts can be selected according to in vitro and/or in vivo assays.

Solutions or suspensions used for administering anti-RT aptamers can include one or more of the following components: a sterile diluent such as water for injection, saline solution; fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as EDTA; buffers such as acetates, citrates or phosphates and agents for the adjustment of tonicity such as sodium chloride or dextrose. In one embodiment, a pharmaceutical composition can be delivered via slow release formulation or matrix comprising anti-RT aptamers or DNA constructs suitable for expression of anti-RT aptamers in or around a site within the body.

In another aspect the present disclosure provides novel compositions for antiviral therapy. For example, the nucleic acids of the present disclosure can serve as a carrier for other known or novel antiviral or other drugs. For example these nucleic acids can be used in a pharmaceutical composition targeting biological targets in cells, tissues, organisms, etc. Given the suitability of nucleic acid molecules to modification, a drug-carrier complex can be formed by chemical modifications to any one or more of the domains described herein. In particular any free end of the helical domain, and portions of the linker domain, can be coupled to or conjugated with other molecules to accomplish delivery and inhibition of targeted proteins. In particular, other drug molecules can be covalent bound or reversibly associated with any domain of the nucleic acid molecules described herein, but particularly the linker domain and the double helical domain. Moreover, each domain may be separately introduced to another known drug molecule to from a modified domain that may then be incorporated into a nucleic acid molecule as described herein. For example, the double helical domain or G-quadruplex domain can be separately introduced to another known drug then incorporated into a nucleic acid molecule as described herein, to provide a carrier for the drug.

F. VECTORS

Other embodiments of the present disclosure include a vector comprising the nucleic acid molecules of the present disclosure. Generally a vector can be any nucleic acid that in a cell or cells directs expression of a sequence, gene or genes of interest that is incorporated in the vector sequence. Such vectors are useful for propagating the nucleic acid molecules or for expression as well as other applications. Such vectors, methods of producing them, and methods for cloning the nucleic acids molecules into said vectors are generally well known in the art.

The vector may particularly be a plasmid, a cosmid, a virus, recombinant virus or a bacteriophage such as any of those used conventionally in genetic engineering. The vector may be for example a DNA vector wherein thymidine (T) replaces uridine (U). Also encompassed by the present disclosure is a host cell or cells comprising such vectors. Vectors may also include marker genes, such as, e.g., luciferase and green fluorescent protein genes. Sequences, inserts, clones, vectors and the like can be isolated from natural sources, obtained from such known sources such as ATCC or GenBank libraries or from commercial sources, or prepared by synthetic or recombinant methods.

Expression vectors can be derived for example from viruses, especially retroviruses, vaccinia virus, adeno-associated virus, herpes viruses, or bovine papilloma virus. Those of skill in the art are well-acquainted with methods for constructing recombinant viral vectors. Further guidance can be obtained for example from Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1989).

The vectors containing the nucleic acid molecules of the present disclosure can be transferred into the host cell by well-known methods. Such methods may vary depending on the cellular host (prokaryotic or eukaryotic cells). In particular, eukaryotic cells can be transfected with a variety of known transfection agents, such as calcium phosphate treatment or electroporation techniques. For transfection of prokaryotic cells, calcium chloride for example can be used.

The vectors may further include genes such as marker genes. Marker genes can be used to select the vector in a suitable host cell and under suitable conditions. In an exemplary embodiment, a nucleic acid molecule of the present disclosure is operatively linked to expression control sequences allowing expression in prokaryotic or eukaryotic cells. By "expression" is meant transcription of the polynucleotide into a translatable mRNA. In some embodiments, regulatory elements such as are well known to those of skill in the art can be used to promote expression in eukaryotic cells, especially expression in mammalian cells. Regulatory elements may comprise for example regulatory sequences ensuring initiation of transcription. Poly-A signals (SV40-poly-A site or the tk-poly-A site) may also be used downstream of the nucleic acid molecule to ensure termination of transcription and to stabilize the transcript. Other regulatory elements are known and include for example transcriptional and translational enhancers, and promoter regions. Examples relating to expression in prokaryotic host cells include the PL, lac, trp or tac promoter in *E. coli*. Examples relating to expression in eukaryotic host cells include the AOX1 or GAL1 promoter in yeast, the CMV-, SV40-, RSV-promoters (Rous sarcoma virus), CMV-enhancer, SV40-enhancer and the globin intron in mammalian and other animal cells.

Additionally, the invention relates to a host or host cells transformed with the vector of the invention. Appropriate hosts include transgenic animals, cells such as bacteria, yeast and animal, preferably mammalian cells, fungal cells and insect cells. Transformation protocols including transfection, microinjection, electroporation, etc., are also well known in the art.

Alternatively, the nucleic acid molecules and vectors of the invention can be reconstituted into liposomes for delivery to cells.

G. METHODS

In another aspect the present disclosure provides a method of binding a nucleic acid molecule to a primate lentiviral reverse transcriptase polypeptide. The method includes combining a nucleic acid molecule as described herein and the lentiviral reverse transcriptase polypeptide for a time and under conditions effective to allow the nucleic acid molecule to bind to the lentiviral reverse transcriptase polypeptide such that the binding occurs. The combination may take place in vitro or in vivo. In an exemplary embodiment the lentiviral reverse transcriptase polypeptide has at least 60% sequence identity with SEQ ID. NO: 1. The method can include combining the lentiviral reverse transcriptase polypeptide as expressed by a bacterial cell, and the further step of examining inhibition of the lentiviral reverse transcriptase polypeptide activity. For example, a functional assay showing inhibition of DNA-dependent DNA polymerization following combining the nucleic acid molecule as described herein and the lentiviral reverse transcriptase polypeptide, provides evidence of binding. Alternatively, evidence of binding may be obtained from a polymerase-independent RNase H activity assay. The method may further include examining the affinity of the nucleic acid molecule for the lentiviral reverse transcriptase polypeptide. The method may also include examining the number of binding sites for the nucleic acid molecule present on the lentiviral reverse transcriptase polypeptide. The method may also involve examining or measuring binding of the nucleic acid to the lentiviral reverse transcriptase polypeptide by labeling the nucleic acid molecule with a detectable marker, and then using a signal generated by the detectable marker to detect or measure binding according to method generally well known in the art.

In another aspect the present disclosure provides a method of preparing an isolated nucleic acid molecule that binds a primate lentiviral reverse transcriptase polypeptide, the method including identifying a first nucleotide sequence that provides the double-helical domain, identifying a second nucleotide sequence that provides the G-quadruplex domain, identifying a linker domain which may be nucleosidic or non-nucleosidic (such as HEG), and identifying an aptamer sequence for the isolated nucleic acid molecule that comprises the double helical domain coupled to the G-quadruplex domain by the linker domain. The aptamer sequence is for example a sequence of 30 to 80 nt. The method may further include providing the isolated nucleic acid molecule having the aptamer sequence, for example by providing the identified sequence to a contact laboratory for synthesis, and once having obtained the synthesized molecule having the aptamer sequence, combining the nucleic acid molecule and the lentiviral reverse transcriptase polypeptide expressed by a bacterial cell, for a time and under conditions effective to allow the nucleic acid molecule to bind to the lentiviral reverse transcriptase polypeptide such that binding occurs. The combining may take pale in vitro or in vivo. The method may further include examining inhibition of the lentiviral reverse transcriptase polypeptide activity, for example using any one of a number of RT functional assays such as those described in Held et al (2006). For example, such functional assays include an assay examining inhibition of DNA-dependent DNA polymerization, as described herein elsewhere and in Held et al. (2006). Alternatively the assay may be a polymerase-independent RNase H Activity Assay as described as also described herein elsewhere and in Held et al. (2006).

The method may further include examining the affinity of the nucleic acid molecule for the lentiviral reverse transcriptase polypeptide. The method may further include examining the number of binding sites for the nucleic acid molecule present on the lentiviral reverse transcriptase polypeptide. In some embodiments of the method, the nucleic acid molecule is labeled with a detectable marker which can be used to generate a signal corresponding to the occurrence or amount of binding. Alternatively, methods using the nucleic acid molecule can include conjugating the nucleic acid molecule to a polypeptide, such as a carrier peptide or a cell-penetrating polypeptide.

H. KITS

In another aspect the present disclosure relates to kits including at least one nucleic acid molecule according to the present disclosure, which is used for inhibiting a primate lentiviral reverse transcriptase. Kits according to the present disclosure can include one or more additional reagents useful for inhibiting, or measuring inhibition of a primate lentiviral RT according to the present disclosure. A kit generally includes a package with one or more containers holding the reagents, as one or more separate compositions or, optionally, as admixture where the compatibility of the reagents will allow. The kit can also include other material(s), which may be desirable from a user standpoint, such as a buffer(s), a diluent(s), a standard(s), and/or any other material useful in sample processing, washing, or conducting any other step of the assay. For example, a kit according to the present disclosure may contain a labeled DNA primer and a DNA template corresponding to a portion of a nucleotide sequence encoding the lentiviral reverse transcriptase polypeptide.

Test kits according to the present disclosure preferably include instructions for carrying out one or more assays of inhibition for measuring inhibition of a primate lentiviral RT by nucleic acid molecules according to the present disclosure. Instructions included in kits of the present disclosure can be affixed to packaging material or can be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

By way of example and not of limitation, examples of the present disclosures shall now be given.

I. EXAMPLES

Experimental Materials and Methods

For all examples, RT's were expressed in *Escherichia coli* and purified as previously described in Held, D., et al., (2006) J. Biol. Chem., 281, 25712-25722, which is herein incorporated by reference in its entirety. Except where noted, all assays utilized RT from HIV-1 strain HXB2 (group M, subtype B). Aptamer RT6 was synthesized and purified by Operon Biotechnologies, Inc., (Huntsville, Ala., USA; www.operon.com). All other aptamer oligonucleotides and primer/template substrates were synthesized and purified by Integrated DNA Technologies, Inc. (www.idtdna.com). The original full-length aptamers were 81 nt in length and previously described in Schneider, D. J., et al. (1995) Biochem. 34, 9599-9610. The "full-length" aptamers studied here were synthesized as 80-nt molecules by removing the 3'-terminal dG residue. This change was without functional consequence, as observed IC50 values were similar to those measured previously as described in Schneider, D. J., et al. (1995). Computational predictions of DNA secondary structures with mfold 3.1 (www.rpi.edu/-zukerm/; as described in Mathews, D. et al. (1999) J. Mol. Biol., 288, 911-940; and Zuker, M. (2003) Nucleic Acids Res. 31, 3406-3415) utilized only the nonquadruplex portions of each molecule. All peptides and oligonucleotides used in the examples are listed herein above, provided in Tables 1-5, or set forth below in the following section describing RT functional assays.

Inhibition of RT Enzymatic Activities

Aptamer DNA was denatured by heating to 95° C. for 5 min, followed by slow cooling at a rate of 2° per minute to room temperature and stored in frozen condition. Subsequent dilutions were made from this refolded stock without additional refolding. Measurements of DNA-dependent DNA polymerization (DDDP) were carried out essentially as described in Held, D., et al., (2006).

For DDDP assays, an 18-nt Cy3-labeled DNA primer (Cy3-GTCCCTGTTCGGGCGCCA, SEQ ID NO. 64), was annealed to a 103-nt synthetic DNA template corresponding to the primer-binding sequence and U5 segments of HIV-1 strain HXB2

(103 Template sequence:
SEQ ID NO: 65
AAGTAGTGTGTGCCCGTCTGTTGTGTGACTCTGGTAACTAGAGATCCCTC

AGACCCTTTT;.)

Reactions were assembled in reaction buffer (50 mM Tris-HCl pH 8.3, 75 mM KCl, 5 mM MgCl$_2$, 10 mM DTT) with 30 nM primer, 45 nM template and 0.2 mM dNTPs. After annealing primer and template strands, DNA aptamers were added. Reactions were initiated by adding RT to a final concentration of 3 nM active site. For IC50 measurements, final aptamer concentrations were 0 nM, 0.3 nM, 1.0 nM, 3.0 nM, 10 nM, 30 nM, 100 nM and 300 nM. Additional reactions included 1 µM and 3 µM where indicated. After 10 min at 37° C., reactions were quenched by addition of 2 volumes (20 µl) of gel-loading buffer (95% formamide with 0.01% bromophenol blue). For reactions assessing monovalent ion dependence, 75 mM KCl was replaced with 75 mM NaCl where indicated.

Reaction products were separated using denaturing (8M urea) 10% PAGE and scanned for fluorescence using a Fujifilm FLA5000 imaging system. RT activity data were collected using Fujifilm Multi Gauge V2.3 image analysis software. Competitive inhibition by aptamers is due to a decrease in the concentration of available enzyme, and is described by the two-state model for RT-aptamer binding [Equation (1)]:

$$Y=100[\text{aptamer}]=(IC50+[\text{aptamer}] \qquad 1$$

where Y is the measured percent activity at a given inhibitor concentration. This equation can be rearranged to a convenient form [Equation (2)] for curve-fitting with GraphPad Prism software to obtain IC50 values for aptamer inhibition:

$$Y=100/[1+10(\log IC50\sim Xi] \qquad 2$$

where X is the log of the inhibitor concentration. Error terms for reported IC50 values are the standard deviations among triplicate assays.

For the polymerase independent RNase H Activity Assay, a 43-nt, fluorescently labeled RNA oligonucleotide corresponding to the 5'-end of the HXB2 RNA genome (5'-Cy3-GGUCUCUCUGGUUAGACCAGAUCUGAGC-CUGGGAGCUCUCUGG-3') (SEQ ID NO: 66) was subjected to RNase H cleavage by RT when annealed to a DNA oligonucleotide complementary to the 5' 53 nt of the HXB2 genomic RNA (5'-CCCTAGTTAGCCA-GAGAGCTCCCAGGCTCAGATCTG-GTCTAACCAGAGAGACC-3') (SEQ ID NO: 66). Reactions were assembled by mixing 30 nM RNA and 60 nM DNA complement in reaction buffer, and individual reaction aliquots (including aptamer) were prepared as described above. Reactions were initiated by the addition of 4 µl of RT, incubated at 37° C. for 3 min, and quenched and analyzed as described for the above assays.

Circular Dichroism Spectroscopy

DNA aptamer samples (SN, RIT and RT6-B) were prepared essentially as for inhibition assays, by heating to 90° C. and renaturing at 25° C. for 20 min. The concentrations 4 µM or 2 µM were adjusted in the corresponding buffers (K-buffer=50 mM Tris-HCl pH 8.3, 75 mM KCl, 5 mM MgCl$_2$, 10 mM DTT; Na-buffer=50 mM Tris-HCl pH 8.3, 75 mM NaCl, 5 mM MgCl$_2$, 10 mM DTT). Near-UV circular dichroism (CD) spectra were acquired at 25° C. using an Aviv 62DS spectrometer (Lakewood, N.J.) at 1.0 nm intervals between 350 nm and 210 nm in a 1.0 mm quartz cuvette, averaging each data point for 10 s.

Example 1

Nucleic Acid Molecules with Extended Quadruplex Loops

FIG. 1 shows two alternative configurations for exemplary aptamers according to the present disclosure. The upper drawing shows a hairpin loop structure in which a 3' end of the double helical domain is coupled to the linker domain, and the linker domain is coupled to a 5' end of the G-quadruplex domain. The lower drawing shows an alternative structure involving a terminal loop, a 3' end of the double helical domain coupled to the linker domain, and a 5' end of the double helical domain coupled to the linker domain.

Figure 2:
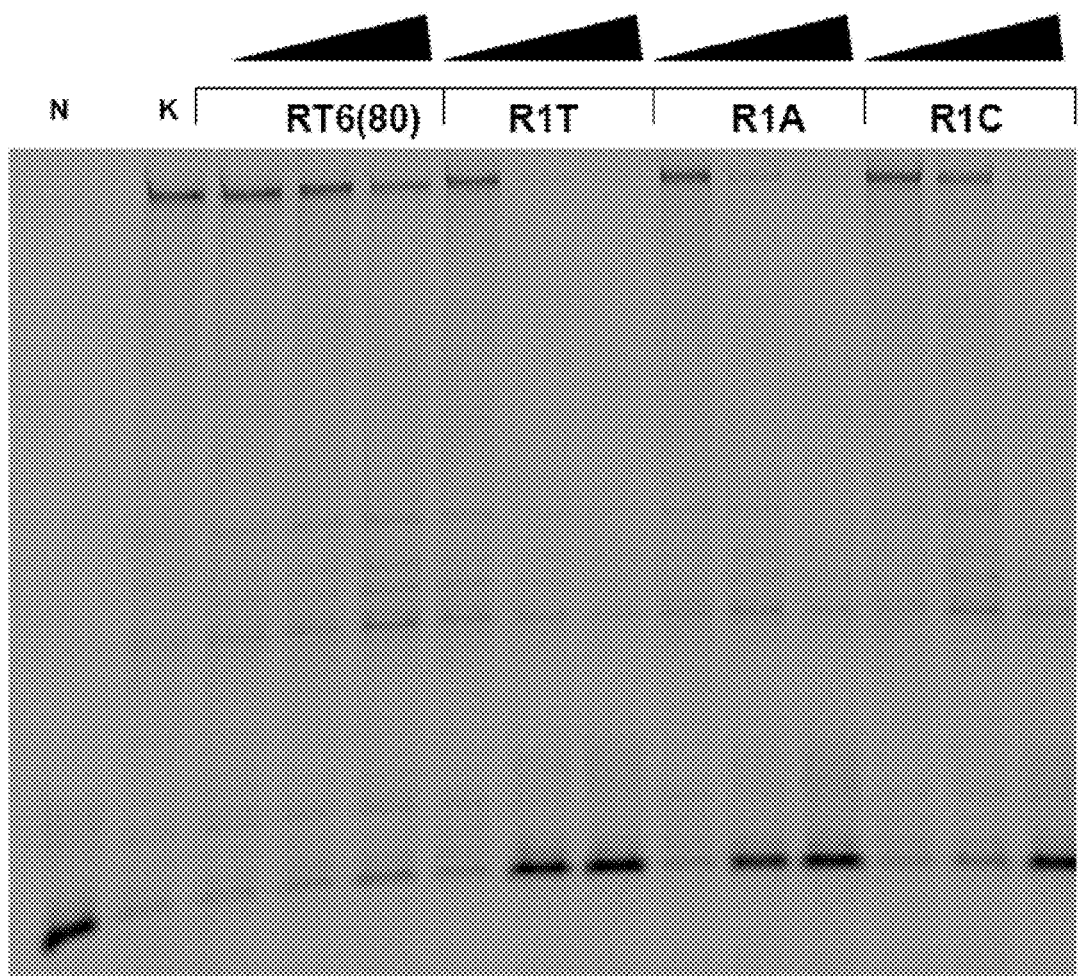
FIG. 2 shows the inhibition of HIV-1 (HXB2) RT polymerization using ssDNA molecules. RT6(80)—ssDNA aptamer (Schneider D., et. al., Biochemistry (1995), 34:9599-9610); R1T is a nucleic acid molecule in which intervening bases in the quadruplex domain are single Ts; R1C—a nucleic acid molecule in which the intervening bases in the quadruplex domain are single Cs; R1A—a nucleic acid molecule in which the intervening bases in the quadruplex domain are single As. The increasing final concentrations of inhibitor in the reactions were as follows: 10, 30 and 100 nM; N—the control reaction, without RT protein; K—the control reaction, without any inhibitor.
Figure 3:
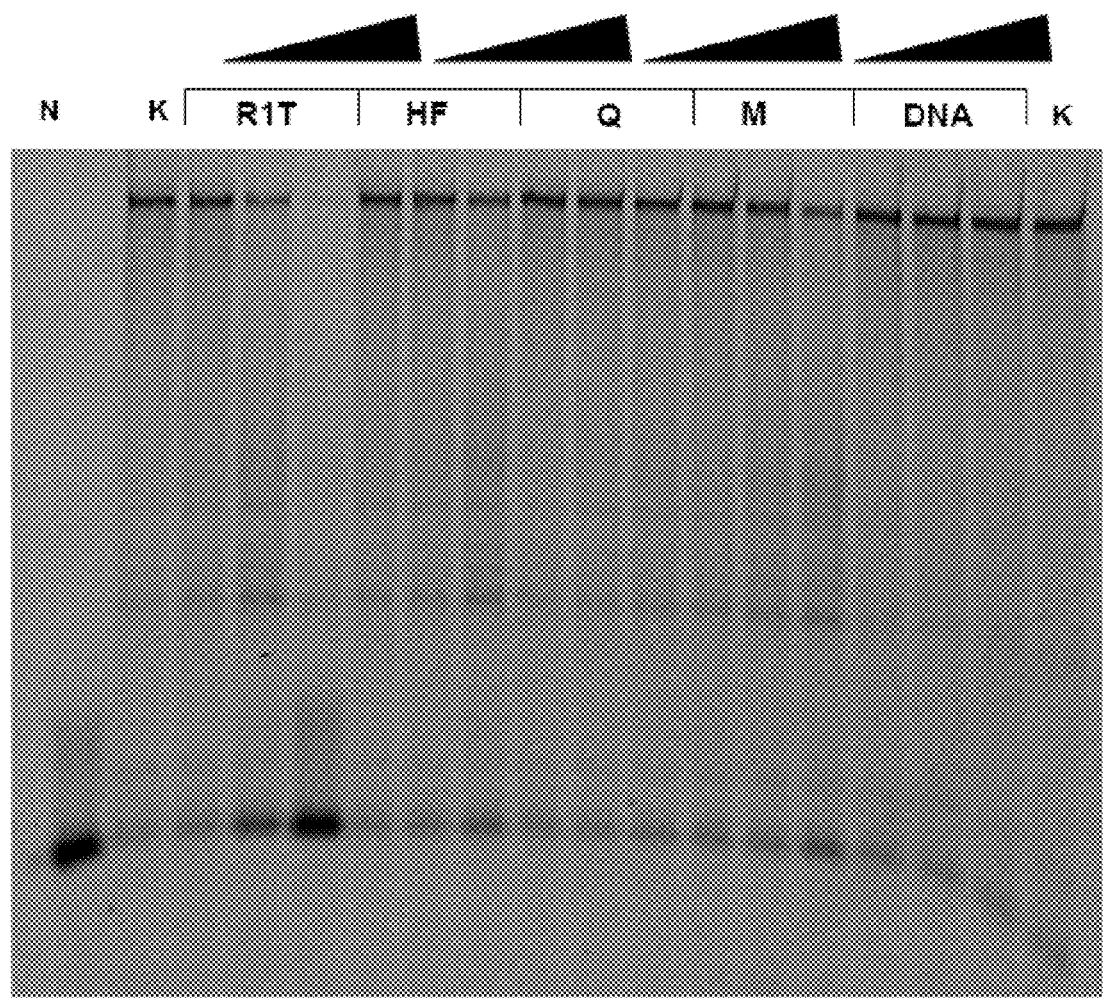
FIG. 3 shows the inhibition of HIV-1 (HXB2) RT polymerization using ssDNA molecules. R1T—the nucleic acid molecule in which the intervening bases in the quadruplex domain are single Ts; HF—the double helical domain only; Q—the quadruplex domain only; M—a mix of HF and Q in ratio, 1:1, but lacking a physical connection; DNA—random fragment of DNA molecule (increasing final concentrations of inhibitor in reactions as follows: 10, 30 and 100 nM for R1T and 10, 30 and 100 µM for HF, Q, M and DNA; N—the control reaction, without any RT protein; K—the control reaction, without any inhibitor).
Figure 4A:
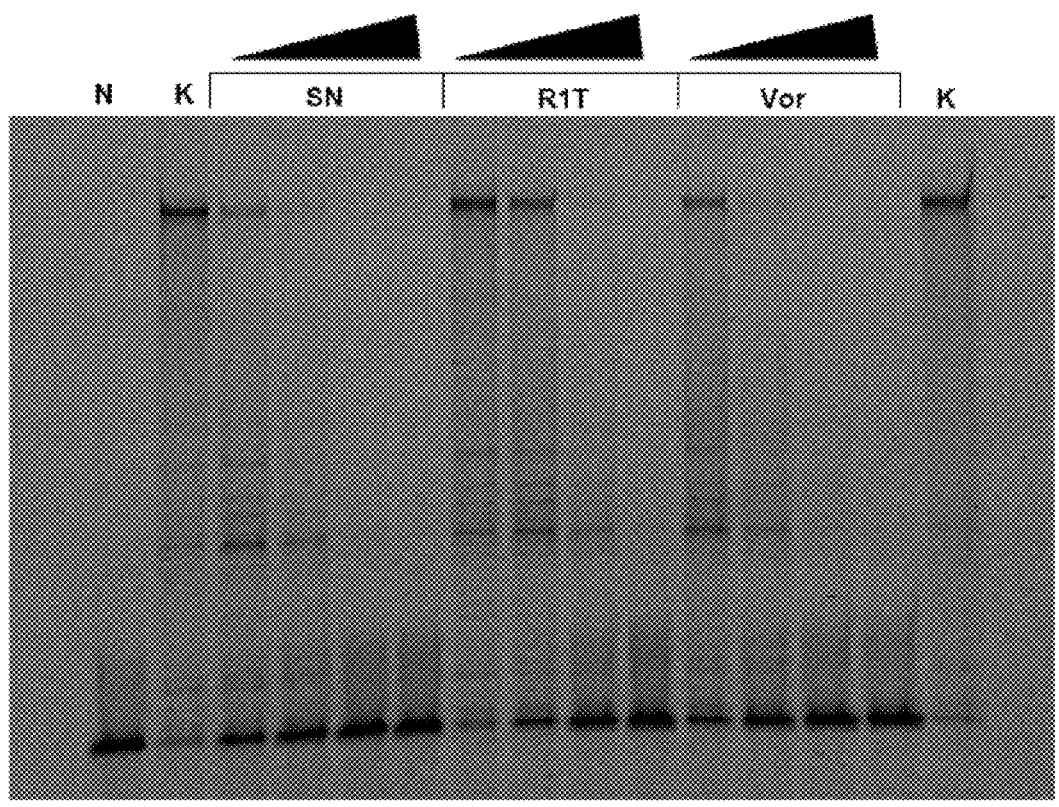
FIG. 4A shows the inhibition of HIV-1 (HXB2) RT polymerization using ssDNA molecules in standard assay buffer (K+). R1T—the nucleic acid molecule in which the intervening bases in the quadruplex domain are single Ts; SN (Supernova)—the nucleic acid molecule in which the intervening bases in the quadruplex domain are replaced by Sp-C18 (HEG); Vor ("RT6-B")—a nucleic acid molecule in which ATC is deleted from the 3' end of the RT-6 "full-length" apatmer starting sequence (increasing final concentrations of inhibitor in reactions as follows: 10, 30 and 100 nM; N—the control reaction, without RT protein; K—the control reaction, without any inhibitor).
Figure 4B:
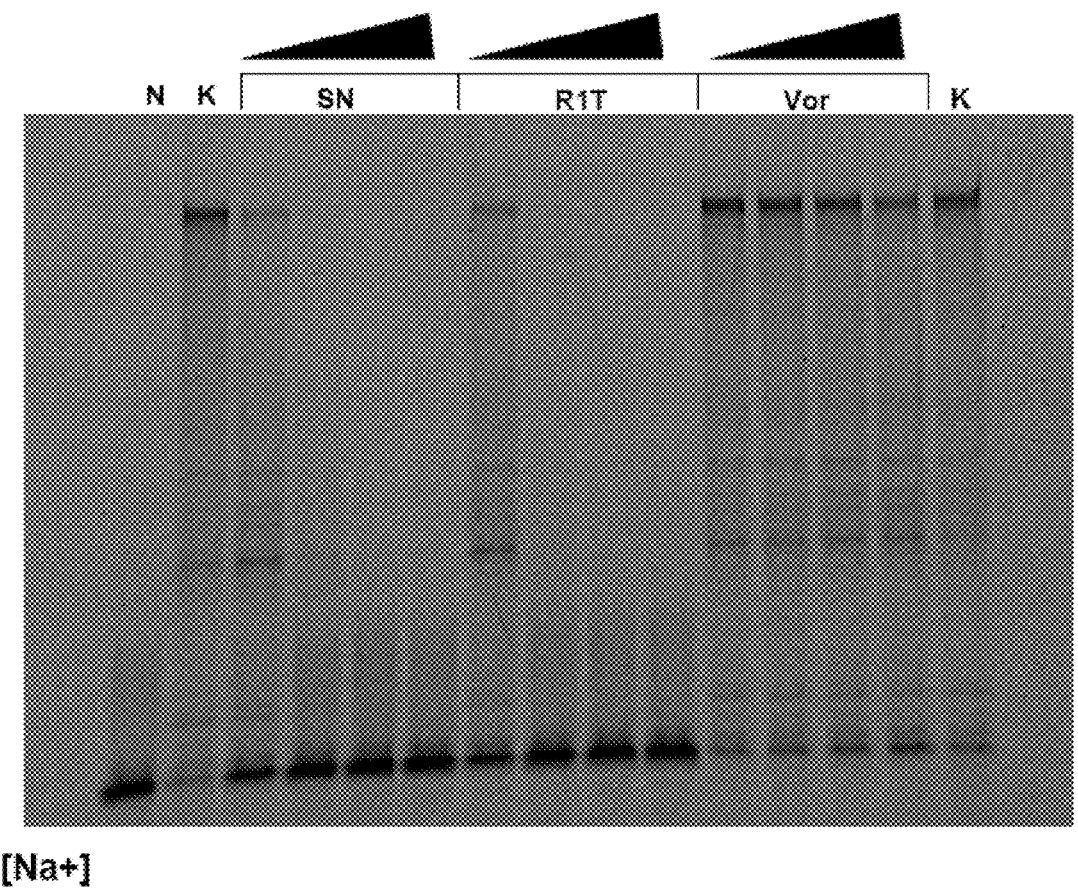
FIG. 4B shows the inhibition of HIV-1 (HXB2) RT polymerization using ssDNA molecules in buffer with Na+ as the only monovalent ion. R1T—the nucleic acid molecule in which the intervening bases in the quadruplex domain are single Ts; SN (Supernova)—the nucleic acid in which the intervening bases in the quadruplex domain are replaced by Sp-C18(HEG); Vor ("RT6-B")—a nucleic acid molecule in which ATC is deleted from the 3' end of the RT-6 "full-length" apatmer starting sequence (increasing final concentrations of inhibitor in reactions as follows: 10, 30 and 100 nM; N—the control reaction, without RT protein; K—the control reaction, without any inhibitor).
Figure 5:
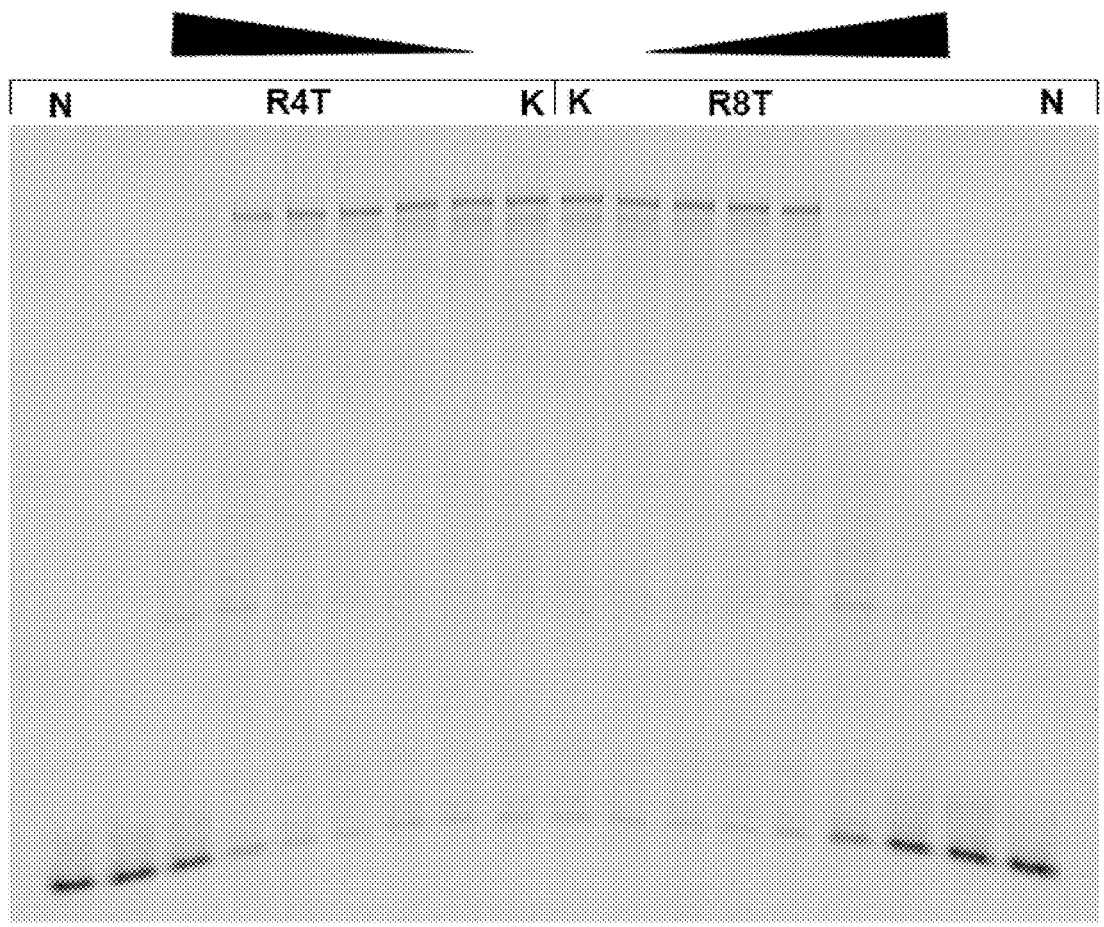
FIG. 5 shows the inhibition of HIV-1 (HXB2) RT polymerization using ssDNA molecules. R4T—the nucleic acid molecule in the intervening bases in the quadruplex domain are single Ts (increasing final concentrations of inhibitor in reactions are following: 0.3, 1, 3, 10, 30, 100 and 300 nM); R8T—the nucleic acid molecule in the intervening bases in the quadruplex domain are eight Ts (increasing final concentrations of inhibitor in reactions as follows: 0.3, 1, 3, 10, 30, 100 and 300 nM; N—the control reaction, without RT protein; K—the control reaction, without any inhibitor).

Nucleic acid molecules having one of the two forms were prepared and tested as set forth elsewhere herein. As shown in FIGS. 2-3, R1T, R1A and R1C (Table 1) demonstrated strong inhibitory effects on RT, particularly in comparison to a helical domain alone, and control sequences. These aptamers are characterized by extended mononucleotide loops of varying length. As shown in FIG. 5, R4T and R8T showed a relatively high level of RT inhibition. Also, SN, which is characterized by extended loops created by replacing nucleotides with HEG, demonstrated a relatively high level of RT inhibition as shown in FIGS. 4A-B.

Example 2

Nucleic Acid Molecules with Linker Domains of Varying Length and Composition

The effect of changing the length and composition of the linker domain in the aptamers was examined by changing the linker domain sequence, varying its length from one through sixteen nucleotides, or substituting N7 (2'-hydroxyethyl) guanine for the nucleotide sequence, and then testing each variant for inhibition of RT.

FIGS. 6-11 show various gel-blot results obtained for each aptamer tested, as indicated near the top of each figure. The results show that increasing the length of the linker domain does not significantly affect the level of RT inhibition by the aptamer. For example, the R1N type aptamers are highly tolerant of a linker of increased length. For example, the results obtained with sequence L10, in which the length of linker domain is sixteen (all T's), were not significantly different from those obtained with L1 in which the linker domain consisted of a single T.

Sequences tested included the following:

```
                                              (SEQ ID NO: 75)
L1:  CGCCTGATTAGCGATACTcaggcgTgggTgggTgggTggg (SEQ ID NO: 59)
L3:  CGCCTGATTAGCGATACTcaggcgTTTTgggTgggTgggTggg (SEQ ID NO: 60)
L4:  CGCCTGATTAGCGATACTcaggcgTTTTTTTTgggTggg
     TgggTggg (SEQ ID NO: 76)
L5:  CGCCTGATTAGCGATACTcaggcgAgggTgggTgggTggg (SEQ ID NO: 61)
L6:  CGCCTGATTAGCGATACTcaggcgAAgggTgggTgggTggg (SEQ ID NO: 77)
L7:  CGCCTGATTAGCGATACTcaggcgAAAAgggTgggTgggTggg (SEQ ID NO: 78)
L8:  CGCCTGATTAGCGATACTcaggcgAAAAAAAAgggTgggTgggTggg (SEQ ID NO: 79)
L9:  CGCCTGATTAGCGATACTcaggcgTTTTTTTTTTTTgggTggg
     TgggTggg (SEQ ID NO: 62)
L10: CGCCTGATTAGCGATACTcag-
     gcgTTTTTTTTTTTTTTTTgggTggg
     TgggTggg (SEQ ID NO: 63)
HEG (alt. R1T-HEG):
CGCCTGATTAGCGATACTcaggcg(HEG)gggTgggTgggTggg
```

Figure 6:
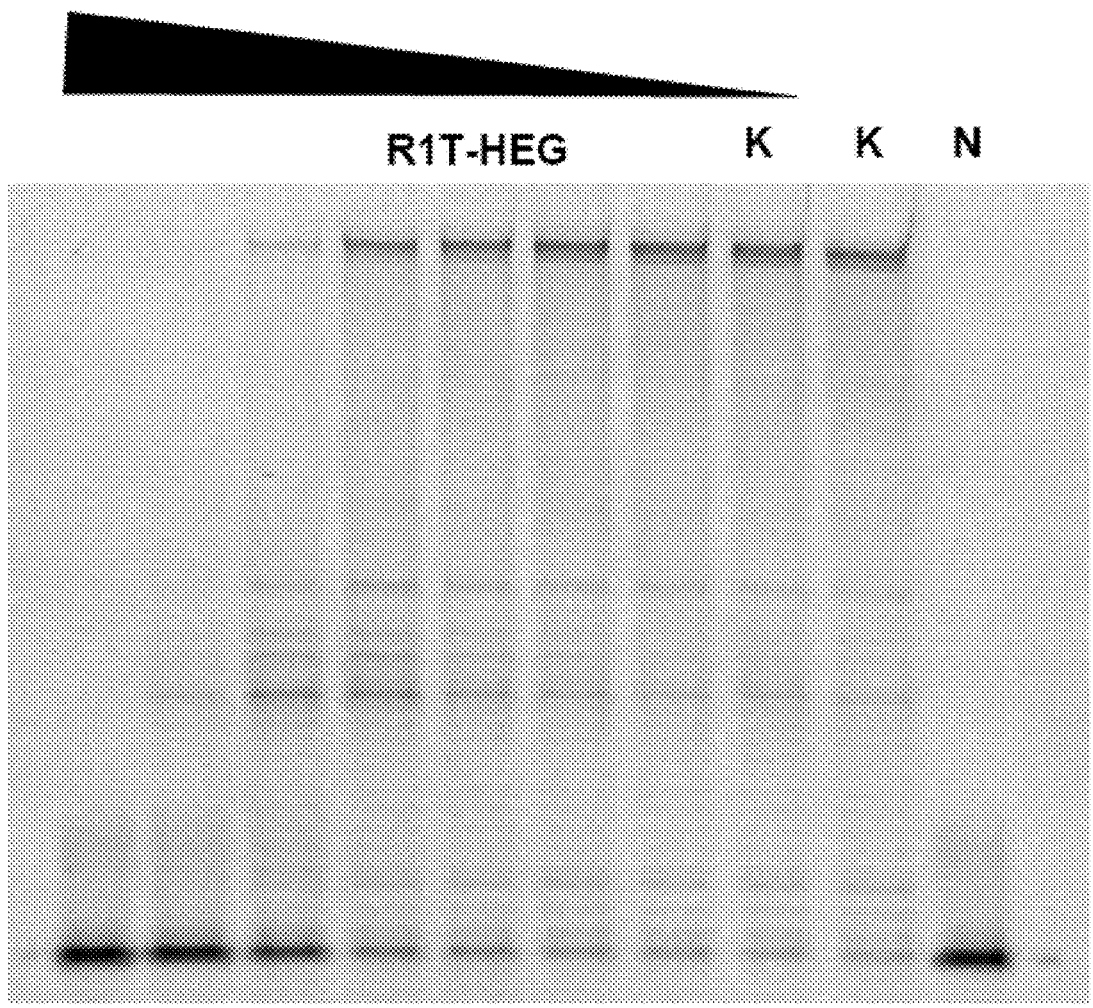
FIG. 6 shows the inhibition of HIV-1 (HXB2) RT polymerization using ssDNA molecules. R1T-HEG—the nucleic acid molecule in which the intervening bases in the quadruplex domain are single Ts and the linker domain connecting the G-quadruplex domain and the double helical domain is HEG, (increasing final concentrations of inhibitor in reactions as follows: 0.3, 1, 3, 10, 30, 100 and 300 nM; N—the control reaction, without RT protein; K—the control reaction, without any inhibitor).

Additional results from the functional assay of sequence HEG (alt. R1T-HEG) as shown in FIG. 6, also showed that substituting HEG for the linker domain did not significantly reduce RT inhibition by the aptamer.

Example 3

Figure 7:
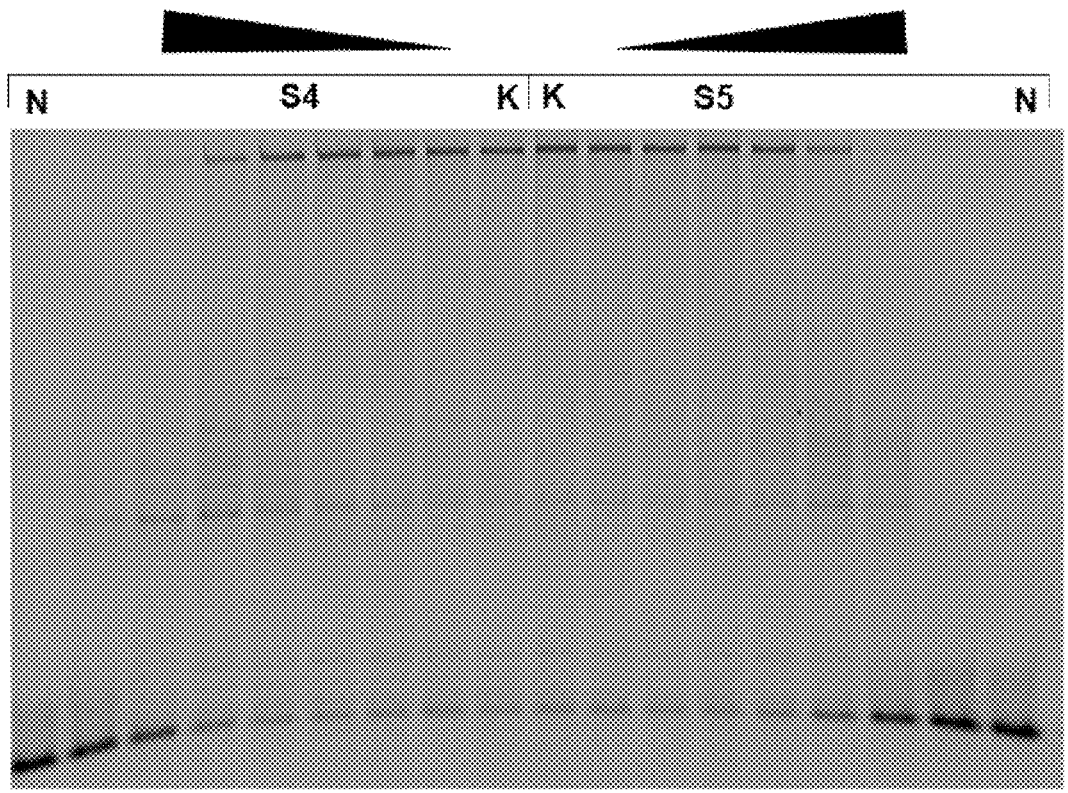
FIG. 7 shows the inhibition of HIV-1 (HXB2) RT polymerization using ssDNA molecules. S4—a nucleic acid molecule in which the intervening bases in the quadruplex domain are single Ts, and the helical domain includes a shortened hairpin loop relative to R1T. The sequence of the helical domain is otherwise identical to R1T (increasing final concentrations of inhibitor in reactions are following: 0.3, 1, 3, 10, 30, 100 and 300 nM); S5—a nucleic acid molecule in which the intervening bases in the quadruplex domain are single Ts, and the helical domain sequence is modified relative to R1T (increasing final concentrations of inhibitor in reactions as follows: 0.3, 1, 3, 10, 30, 100 and 300 nM; N—the control reaction, without RT protein; K—the control reaction, without any inhibitor).

Nucleic Acid Molecules with Varying Sequences, Sequence Length and Configuration Nucleic acid molecules having the following sequences were prepared and then assayed for RT inhibition. The results for S4 and S 5 are shown in FIG. 7. No significant differences in RT inhibition among these variants was observed.

```
                                              (SEQ ID NO: 27)
S1:   CGTGATTAGCGATACTcacgTTgggTgggTgggTggg (SEQ ID NO: 28)
S2:   CGGATTAGCGATACTccgTTgggTgggTgggTggg (SEQ ID NO: 29)
S4:   CGCCTGA ccct TcaggcgTTgggTgggTgggTggg (SEQ ID NO: 30)
S5:   ATCCGCCTGA TTAGCGATACTcagaaggat
      TTgggTgggTgggTggg
```

Example 4

Nucleic Acid Molecules with Varying Topology

Figure 8:
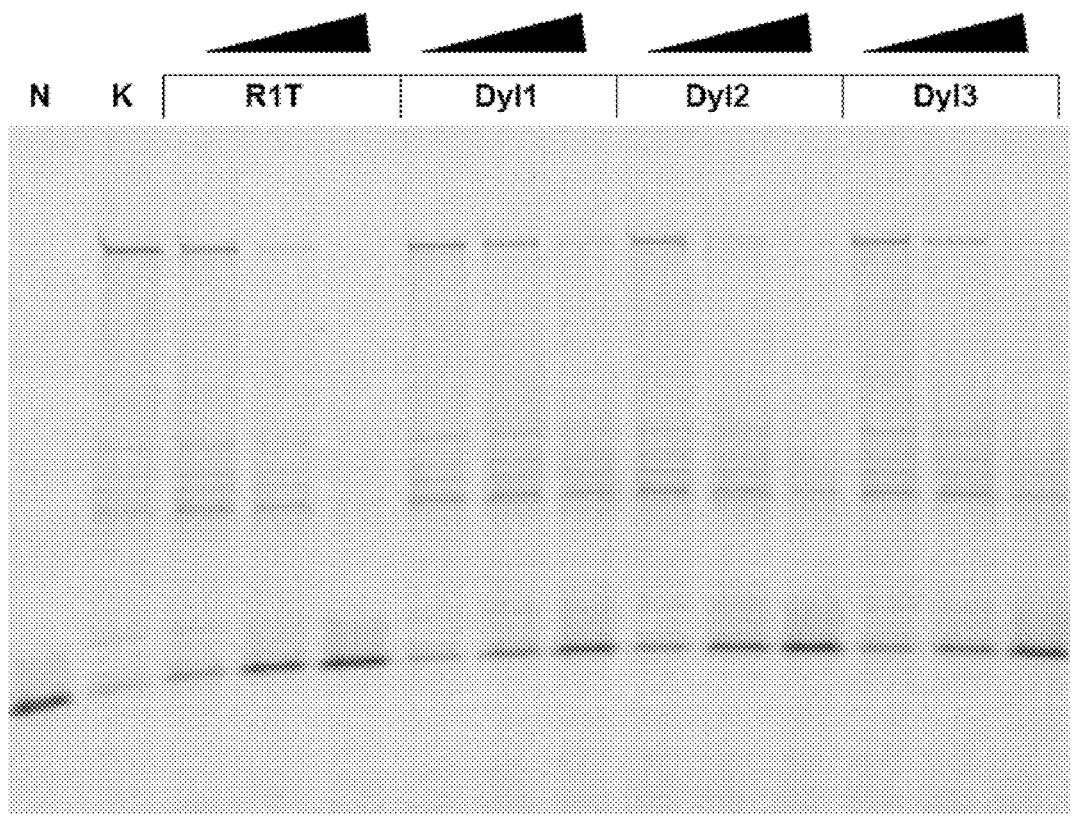
FIG. 8 shows the inhibition of HIV-1 (HXB2) RT polymerization using ssDNA molecules. R1T—the nucleic acid molecule in which the intervening bases in the quadruplex domain are single Ts (increasing final concentrations of inhibitor in reactions are following: 10, and 100 nM); Dyl1—a topologically variant nucleic acid molecule in which the intervening bases in the quadruplex domain remain single Ts (increasing final concentrations of inhibitor in reactions are following: 10, 30 and 100 nM); Dyl2—another topologically variant nucleic acid molecule in which the intervening bases in the quadruplex domain remain single Ts (increasing final concentrations of inhibitor in reactions are following: 10, 30 and 100 nM); Dyl3—another topologically variant nucleic acid molecule in which the intervening bases in the quadruplex domain remain single Ts (increasing final concentrations of inhibitor in reactions as follows: 10, and 100 nM; N—the control reaction, without RT protein; K—the control reaction, without any inhibitor).

Nucleic acid molecules having the following sequences and thus varying topology were prepared and then assayed for RT inhibition, and compared to the results obtained with R1T. The results for Dyl 1, Dyl2 and Dyl 3 are shown in FIG. 8. Dyl5 was also tested.

```
                                                 (SEQ ID NO: 49)
Dyl1:  cgcGCtacTcaggcgTTgggTgggTgggTgggTTCGCCTGAtta
       GCgcg (SEQ ID NO: 50)
Dyl2:  CGCGCGCGCTACTCAGGCGTTGGGTGGGTGGGTGGGTTCGCCTG
       ATTAGCGCGCGCG (SEQ ID NO: 51)
Dyl3:  CGCGGCGCGCGCTACTCAGGCGTTGGGTGGGTGGGTGGGTTCGC
       CTGATTAGCGCGCGCCGCG (SEQ ID NO: 53)
Acut:  GGGTGGGTTCGCCTGATTAGCGATACTcaggcgTTGGGtGGG (SEQ ID NO: 55)
Bcut:  GGGTTCGCCTGATTAGCGATACTcaggcgTTGGGtGGGtGGG
```

Example 5

Nucleic Acid Molecules with Varying G-Quadruplex Domains

Figure 9:
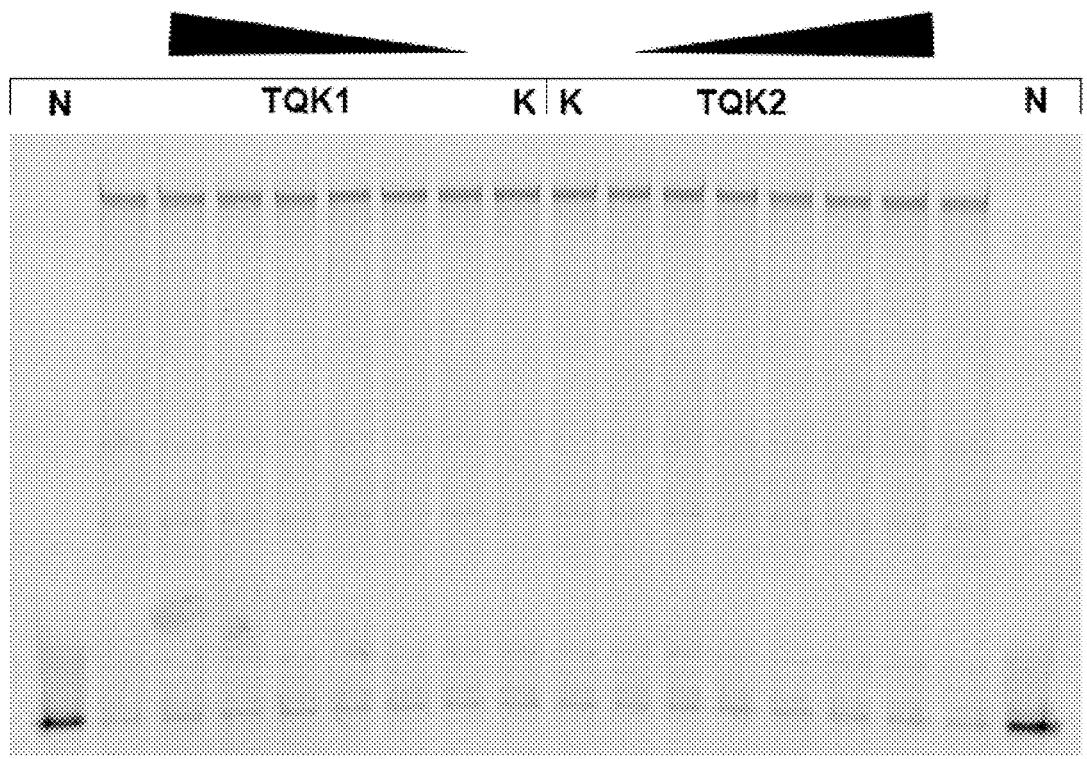
FIG. 9 shows the inhibition of HIV-1 (HXB2) RT polymerization using ssDNA molecules. TQK1—a nucleic acid molecule in which one G in the quadruplex domain is replaced with A (increasing final concentrations of inhibitor in reactions are following: 0.3, 1, 3, 10, 30, 100 and 300 nM); TQK2—another nucleic acid molecule in which another G in the quadruplex domain is replaced with A (increasing final concentrations of inhibitor in reactions as follows: 0.3, 1, 3, 10, 30, 100 and 300 nM; N—the control reaction, without RT protein; K—the control reaction, without any inhibitor).

Nucleic acid molecules having the following sequences were prepared and then assayed for RT inhibition. The results for TQK1 and TQK2 are shown in FIG. 9. The results showed that the number of guanosines in each G-quadruplex domain plays an important role in the level of RT inhibition by the nucleic acid molecule.

```
                                                 (SEQ ID NO: 33)
TQK1    CGCCTGATTAGCGATACTcaggcgTTAggTgggTgggTggg (SEQ ID NO: 34)
TQK2    CGCCTGATTAGCGATACTcaggcgTTgAgTgggTgggTggg (SEQ ID NO: 35)
TQK3    CGCCTGATTAGCGATACTcaggcgTTggATgggTgggTggg (SEQ ID NO: 36)
TQK4    CGCCTGATTAGCGATACTcaggcgTTgggTAggTgggTggg (SEQ ID NO: 37)
TQK5    CGCCTGATTAGCGATACTcaggcgTTgggTgAgTgggTggg (SEQ ID NO: 38)
TQK6    CGCCTGATTAGCGATACTcaggcgTTgggTggATgggTggg (SEQ ID NO: 39)
TQK7    CGCCTGATTAGCGATACTcaggcgTTgggTgggTAggTggg (SEQ ID NO: 40)
TQK8    CGCCTGATTAGCGATACTcaggcgTTgggTgggTgAgTggg (SEQ ID NO: 41)
TQK9    CGCCTGATTAGCGATACTcaggcgTTgggTgggTggATggg (SEQ ID NO: 42)
TQK10   CGCCTGATTAGCGATACTcaggcgTTgggTgggTgggTAgg (SEQ ID NO: 43)
TQK11   CGCCTGATTAGCGATACTcaggcgTTgggTgggTgggTgAg (SEQ ID NO: 44)
TQK12   CGCCTGATTAGCGATACTcaggcgTTgggTgggTgggTggA
```

Example 6

Nucleic Acid Molecules with Varying G-Quadruplex Domains

Figure 10:
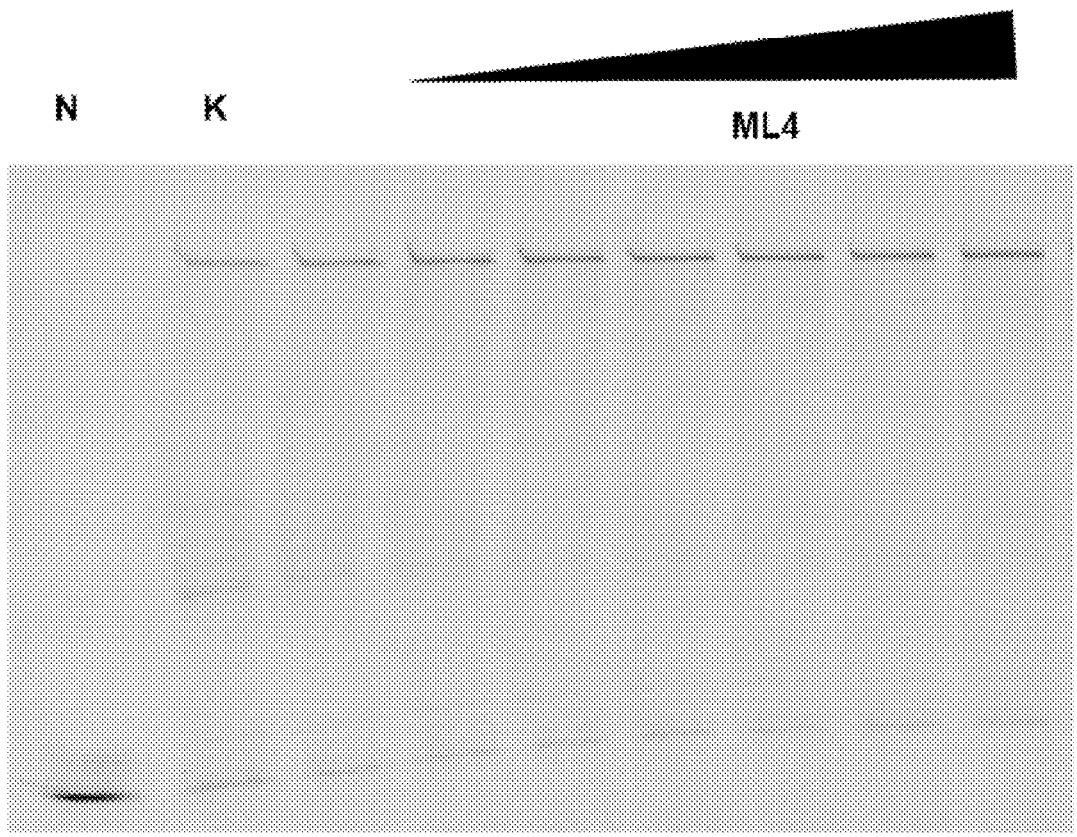
FIG. 10 shows the inhibition of HIV-1 (HXB2) RT polymerization using ssDNA molecules. ML4—a nucleic acid molecule having contains four G4 sequences in the quadruplex domain (increasing final concentrations of inhibitor in reactions as follows: 0.3, 1, 3, 10, 30, 100 and 300 nM; N—the control reaction, without RT protein; K—the control reaction, without any inhibitor).
Figure 11:
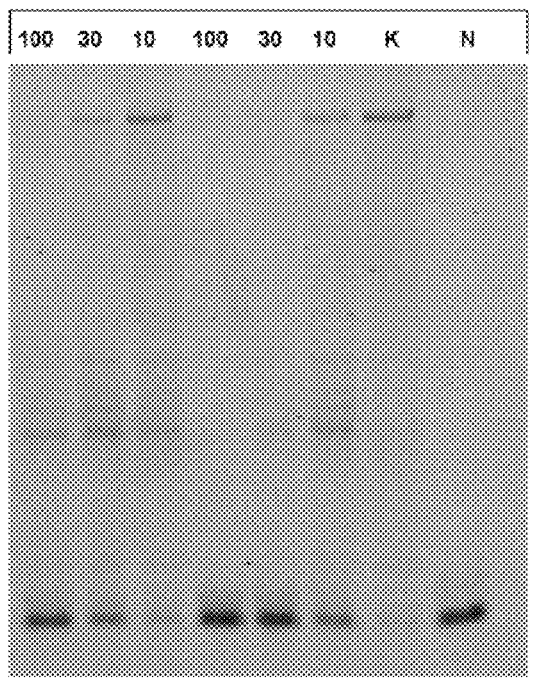
FIG. 11 shows the inhibition of HIV-1 (HXB2) RT polymerization using ssDNA molecules. R1T—the nucleic acid molecule in which the intervening bases in the quadruplex domain are single Ts; Acut—a nucleic acid molecule in which terminal ends are positioned within the quadruplex domain in which the intervening bases remain single Ts; Bcut—another nucleic acid molecule in which terminal ends are positioned within the quadruplex domain in which the intervening bases remain single Ts (increasing final concentrations of inhibitor in reactions as follows: 10, 30 and 100 nM for R1T and for Acut, and 0.3, 1, 3, 10, 30, 100 and 300 nM for Bcut; N—the control reaction, without RT protein; K—the control reaction, without any inhibitor).
Figure 11:
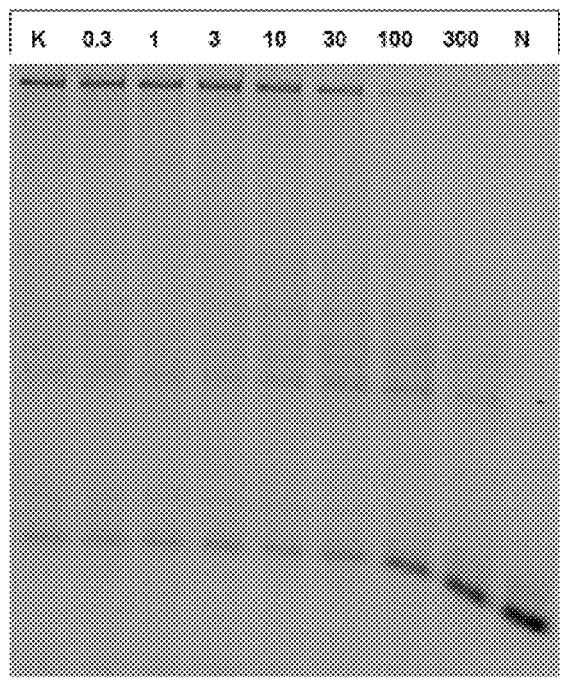

The importance of triplet of guanosines in G-tracts was tested by changing G3 for G2 and G4. The results for ML4 are shown in FIG. 10. The results indicated that nucleic acid molecules having four G3-tracts provide the highest level of RT Inhibition. However other G-quadruplex structures maintain some level of RT inhibition.

```
QK (alt. ML2):
                                                 (SEQ ID NO: 80)
CGCCTGATTAGCGATACTcaggcgTTggTggTggTgg aMu (alt. ML4):
                                                 (SEQ ID NO: 81)
CGCCTGATTAGCGATACTcaggcgTTggggTggggTggggTgggg
```

Example 7

Identification of a Novel Inhibitory DNA Structure within ssDNA Aptamers RT6, RT5 and RT47

Figure 12B:
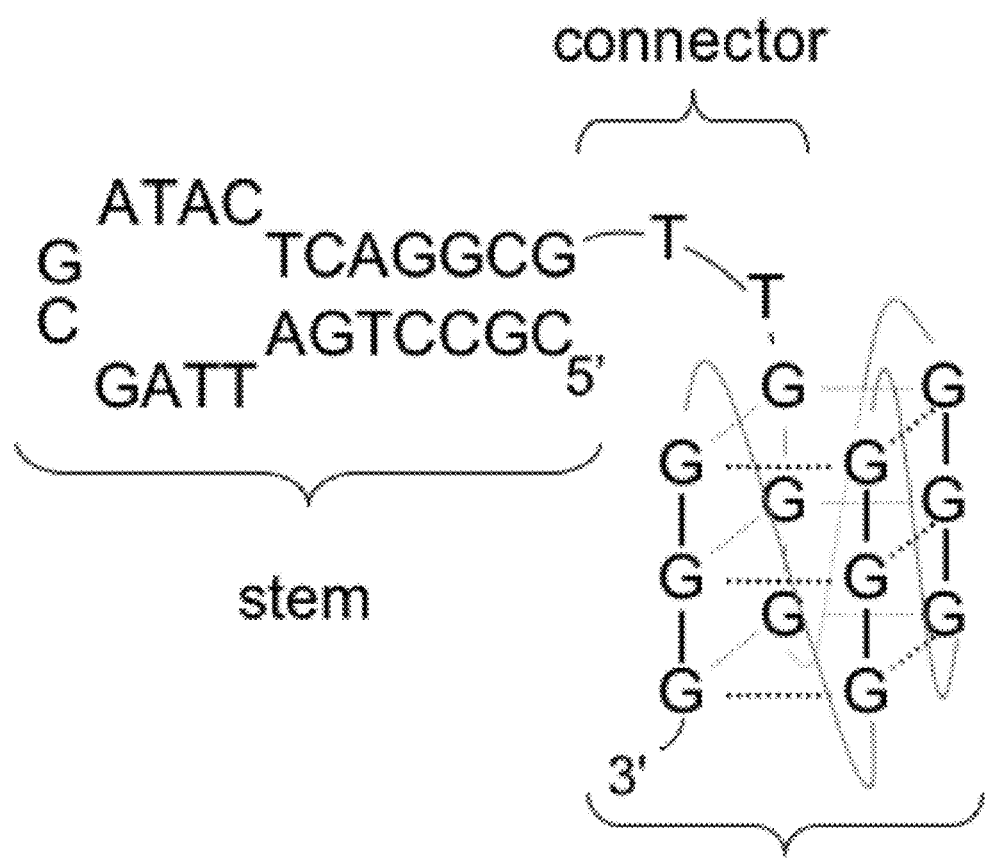
FIG. 12 Quadruplex model for RT6 family of aptamers to HIV-1 RT. (A) Sequences of aptamers RT5, RT6 and RT47 from Schneider et al. et al. as described elsewhere herein. Primer-binding sites for library amplification are in lower case, 35N originally random nucleotides are in upper case, guanosine clusters are underlined. Note that all aptamers analyzed in this work are given in Table 1. (B) Generalized secondary structure of most aptamers studied in this work. Stem and connector sequences shown are those of R1T, SN and several other aptamers. Intra-quadruplex loops are shown as curved lines. (C) Inhibition of HIV-1 RT DDDP activity by aptamer R1T. Aptamer concentrations (nM) are indicated above the lanes. RT and primer/template concentrations used in these assays are 3 nM and 30 nM, respectively. Open and filled arrows on the left indicate positions of unextended primer and full-length product bands, respectively.
Figure 12C:
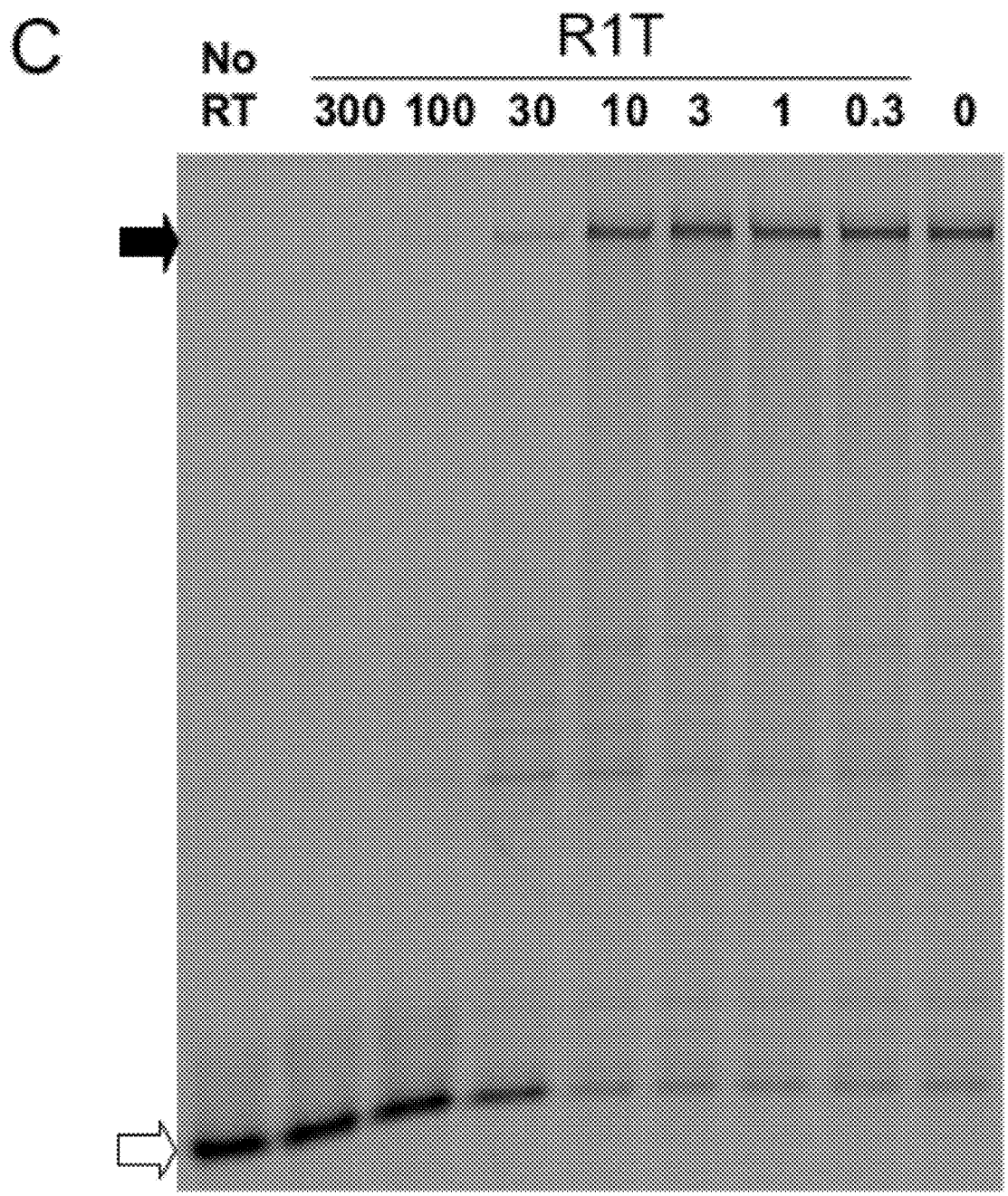

Aptamers RT5, RT6 and RT47 form a subgroup of closely related sequences within Family VI of the ssDNA aptamers identified by Schneider et al. Results disclosed herein show show strong inhibition of DNA polymerization by RT from a subtype B strain of HIV-1 by 80-nt modified versions of each of these three aptamers. The concentration required for half-maximal inhibition (IC50) by RT6 was 36 f 3 nM and was similar for the other two (data not shown). All three aptamers share the same sequence in the first 5-6 nt of the initial 35N random segment (FIG. 12A), and this shared segment is complementary to nucleotides within the 5'-primer-binding constant region. The remainder of each molecule includes four or more stretches of guanosine tri-nucleotide repeats. Five such repeats are evident in RT6. Aptamer RT6-A was generated by removing the 25 nt on the 3'-side of the fourth repeat of RT6 and modifying 5 nt between the third and fourth repeat. Aptamer RT6-A was more than 2-fold more potent for RT inhibition relative to the original RT6 aptamer (IC50=16 f 3 nM). Similar 3' deletions from RT5 and RT47 inactivated these aptamers for RT inhibition unless three guanosines were appended onto the 3'-ends of the truncated species to restore their original termini (data not shown). Removing both the 3'-terminal 25 nt and the 5'-terminal three unpaired nucleotides (ACG) of RT6 generated a 53-nt species designated RT6-B that retained potent RT inhibition (IC50=5.7 f 0.8 nM). Finally, the 41-nt aptamer variant R 1T (IC50=14 f 2 nM, FIG. 12C) was generated in which the intra-quadruplex loop sequences connecting the guanosine triplets in RT6-B were replaced with single thymidine nucleotides. These data suggest a structural model in which each of these aptamers forms a 5'-helical domain connected to a 3'-guanosine quadruplex domain (FIG. 12B).

Example 8

Mutational Support for Quadruplex Formation

To establish the quadruplex positions at which guanosine is required, each of the nucleotides that are proposed to define the G-quadruplex structures within RT6-A was individually changed to adenosine. All 12 G-to-A substitutions abolished RT inhibition (data not shown). These data provide strong evidence that RT inhibition by RT6-A (and by the original RT6) requires a three-tiered quadruplex. When similar mutations were generated in R1T, 11 of the 12 G-to-A mutations were similarly disruptive. However, deleting the first guanosine of the second triplet or changing it to A, C or T only reduced RT inhibition by two- to threefold (TQK4, FIG. 13A, and data not shown). These data suggest that only two tiers of the quadruplex may be absolutely required within R1T. However, inserting or removing one guanosine from each (TGGG) repeat in the original R1T quadruplex to yield (TGGGG)4 in ML4 and (TGG)4 in ML2 prevents aptamer-mediated RT inhibition (data not shown).

Example 9

Sequence Plasticity of Quadruplex Loops and Stem

Figure 13:
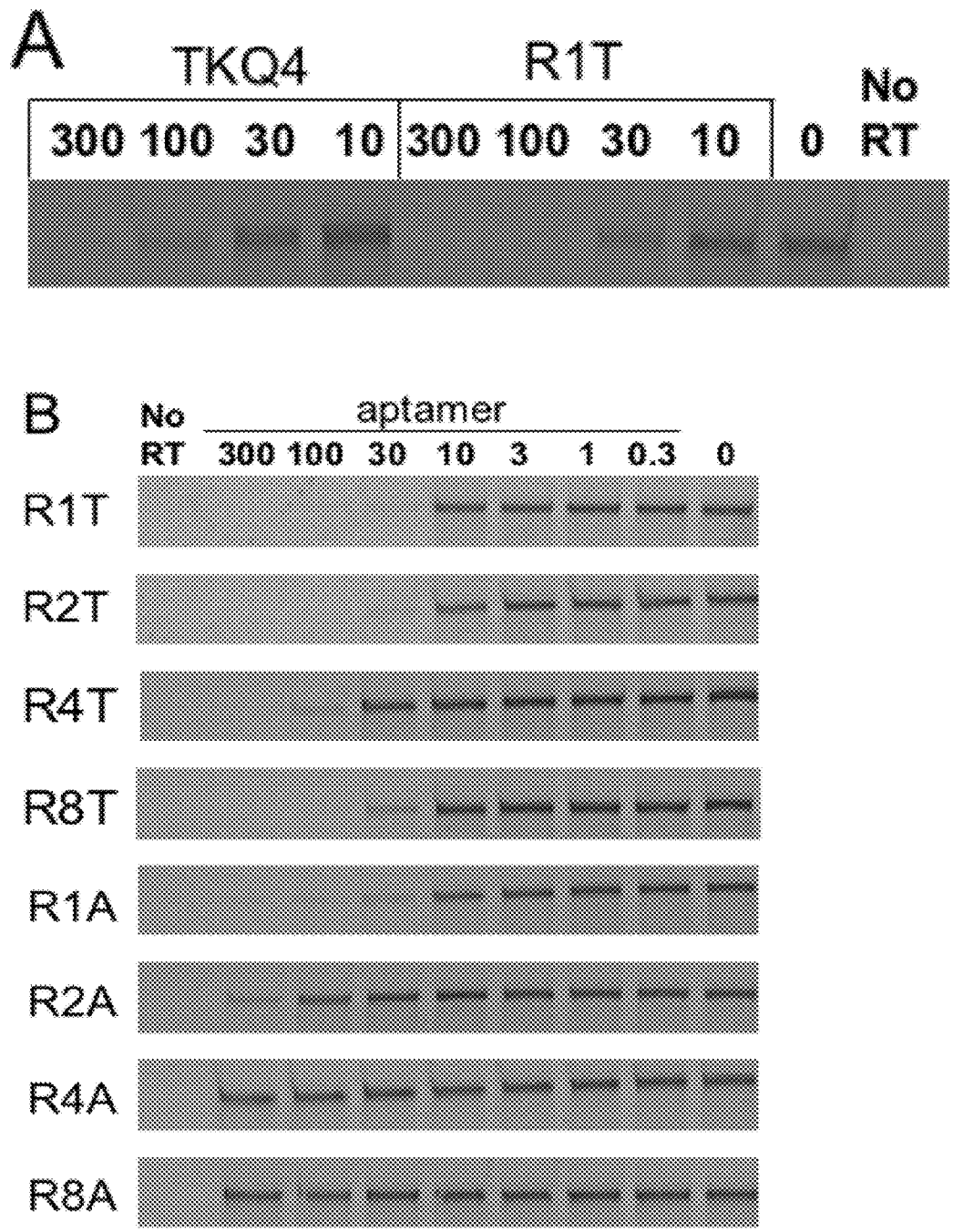
FIG. 13 Sequence plasticity of stems and loops Inhibition of RT DDDP activity by aptamer variants. Aptamer concentrations (nM) are indicated above the lanes. (A) Aptamer TKQ4 retains inhibition even though it carries a G-to-A mutation in the fourth of the 12 G's that comprise the quadruplex. All other G-to-A variants were inactive for inhibition (data not shown). (B) Full concentration range of aptamers from 0.3 nM to 300 nM was used in establishing IC50 values for R1T variants in which quadruplex loops are replaced with multiple thymidines or multiple adenosines. Similar titrations were carried out in triplicate for all aptamers for which IC50 values are reported. Aptamer R1T was included in subsequent panels to provide a consistent reference baseline of inhibition. (C) RT inhibition by aptamer SN, in which quadruplex loops are replaced with hexaethylene glycol. (D) and (E), RT inhibition by aptamers carrying mutations in helical stem domain, as detailed in text.

To define further the sequence requirements within intraquadruplex loops, the single Ts in each loop of R1T were changed to other sizes and sequences. Replacement with single adenosines (R1A, IC50=18 f 7 nM, FIG. 13B) or cytidines (R1C, IC50=26 f 9 nM) was well tolerated, while replacement with single guanosines was not (R1G, IC50>>250 nM). Expanding the loops with runs of two (R2T, $IC_{50}$=13 f 2 nM), four (R4T, IC50~35 nM) or eight (R8T, IC50=20 f 3 nM) thymidines was also well-tolerated. In contrast, expansion of the loops to two (R2A), four (R4A) or eight (R8A) adenosines or with two (R2C) or four (R4C) cytidines yielded aptamers with greatly reduced capacity for inhibiting RT (FIG. 13B). To eliminate the possibility that RT-loop nucleotide contacts are essential for aptamer recognition, the intra-quadruplex loops were replaced with the relatively inert, nonnucleosidic hexaethylene glycol (HEG) to yield the SN aptamer. Interestingly, inhibition by the SN aptamer is more than 10 times more potent (IC50=3.5 f 0.1 nM, FIG. 13C) than the original RT6, and more than fourfold more potent than R1T. The results show that specific loop nucleotides within the quadruplex region are not required for inhibition or for stability, and that the loops are only minimally constrained as to sequence.

Additional variants of R1T were generated to identify sequence constraints within the 7-bp stem comprising the 5'-structural domain. Deletion of 2 bp (S1, IC50=59 f 2 nM) or 3 bp (S2, IC50=110 f 5 nM) from the stem progressively compromised RT inhibition (data not shown), while lengthening the stem to 22 bp slightly improved inhibition (ZAM 1, IC50=10.0 f 1.5 nM). Reversing the sequence orientation within this domain (Srevstem, IC50=26 f 7 nM) had minimal impact on IC50 (FIG. 13D). Replacing the 10 nt at the end of the R1T stem with a CCCT tetraloop (S4, IC50=32 f 1 nM, FIG. 13E) had only a twofold effect on RT inhibition. These results establish that the 5'-domain requires a generic double-helical fragment stabilized by seven or more base pairs of essentially any sequence.

Example 10

Loop Sequences Affect Sensitivity to Ionic Environment

Figure 14:
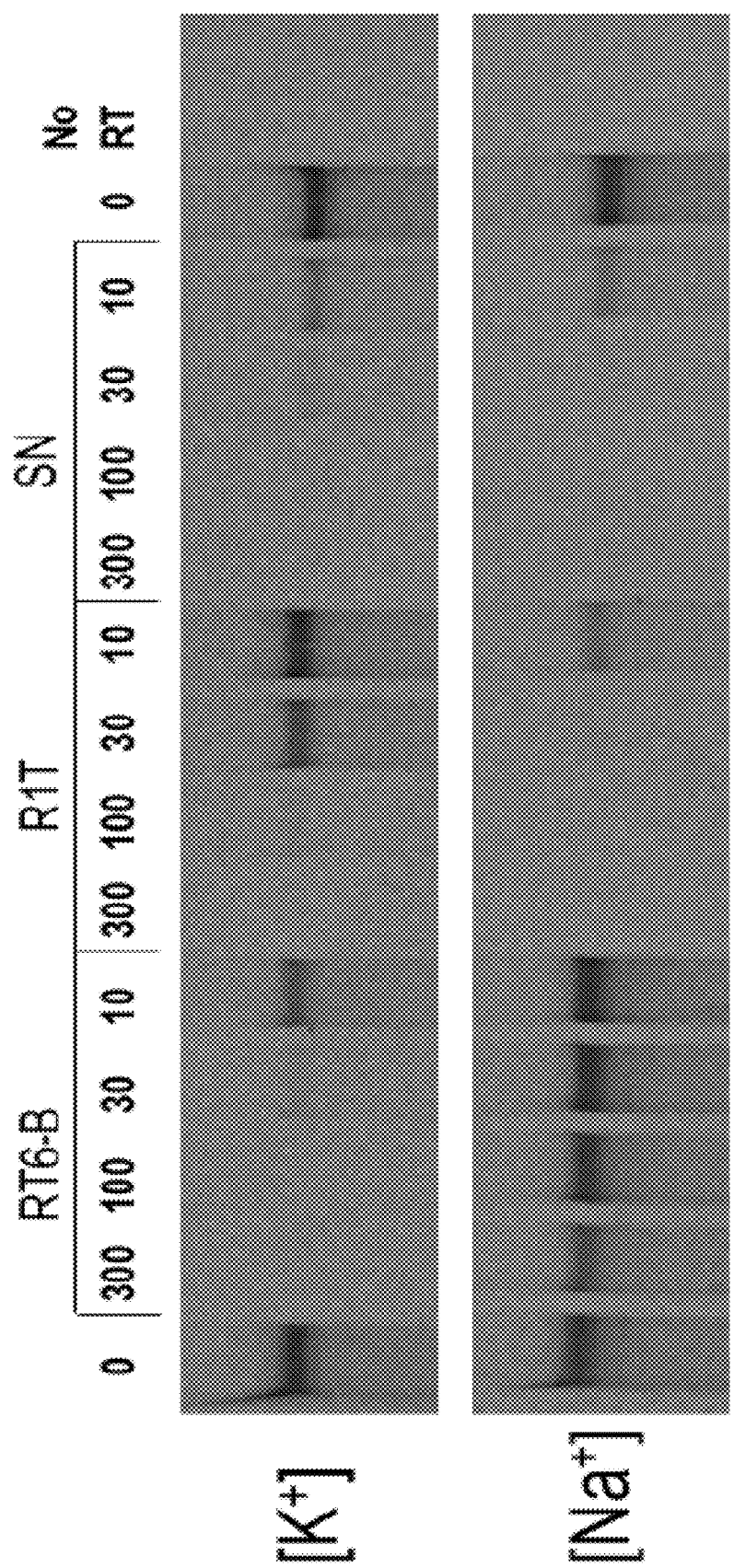
FIG. 14 Loop sequences modulate ionic sensitivity. RT inhibition by aptamers RT6-B, R1T and SN was carried out in normal buffer (potassium as the primary monovalent cation), or in buffers in which potassium was replaced with sodium. Note that in sodium, R1T effected the most potent inhibition.

Potassium ions strongly favor quadruplex formation, while sodium ions are usually less stabilizing and lithium ions are destabilizing. We observed equivalent DNA polymerization activity by HIV-1 RT in buffers containing either $K^+$ or $Na^+$. RT inhibition by aptamers SN, R1T and RT6-B was therefore monitored in the original buffer containing $K^+$ and also in a buffer in which $K^+$ was replaced with $Na^+$. The same RT was nearly inactive in buffers containing $Li^+$, preventing analysis of inhibition in the presence of $Li^+$. All three aptamers strongly inhibited RT in the presence of K. Aptamers SN and R1T were also strongly inhibitory in the $Na^+$-containing buffer, while aptamer RT6-B lost all inhibition under these conditions (FIG. 14). Because these three aptamers differ only in the loop sequences connecting the individual guanosine triplets of the quadruplex, it is concluded that the loop sequences in RT6-B render that aptamer sensitive to ionic destabilization, while the simplified structures of R1T and SN stabilize those aptamers to ionic substitution.

Figure 15:
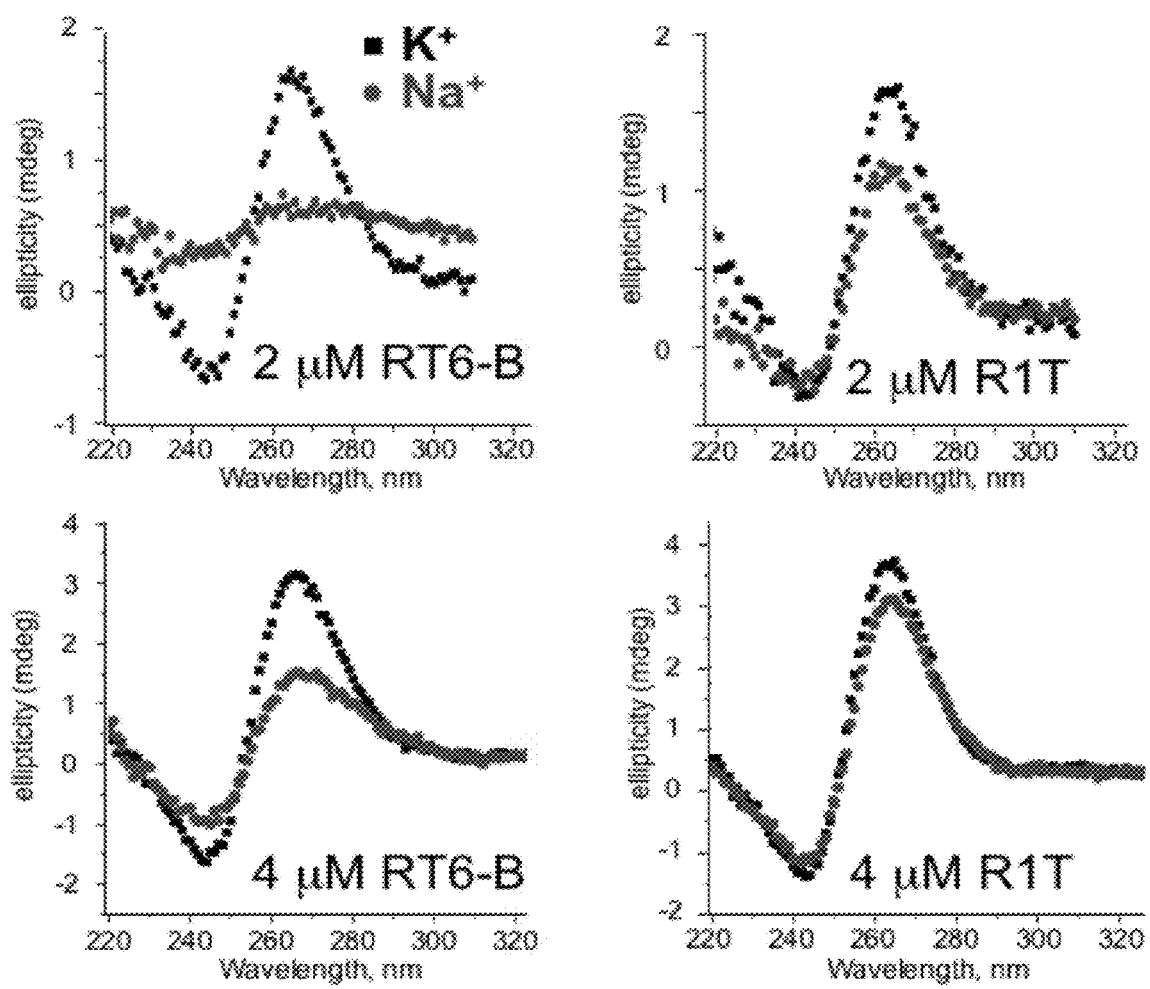
FIG. 15 CD analysis of aptamer structure. Aptamers RT6-B and R1T were analyzed at either 2 ILM or 4 ILM, as indicated on the figure. Black traces indicate normal buffer containing potassium. Red traces indicate buffer in which potassium was replaced with sodium.

Circular dichroism (CD) spectroscopy is a powerful analytical tool for identifying quadruplexes DNA structures. For quadruplexes in which all four strands are in the same orientation (parallel), CD minima and maxima are typically near 240 nm and 264 nm, respectively. For quadruplexes in which strands orientation alternates (antiparallel), the corresponding values are typically near 265 nm and 295 nm, respectively. The CD spectra for RT6-B and R1T both show maxima at 262 nm and minima at 242 nm at room temperature in the presence of $K^+$ (FIG. 15). In $Na^+$ buffer the ellipticity is strongly flattened for RT6-B, especially at low DNA concentration, indicting destabilization of the quadruplex structure. Slight flattening is also evident in R1T, although to a lesser extent. Quadruplexes containing HEG loops, such as the one in aptamer SN, have previously been shown to be more stable than quadruplexes with single T loops in both $K^+$ and $Na^+$ buffers; thus, SN is also expected to retain its quadruplex in the $Na^+$ buffer. These data provide independent confirmation of guano-sine quadruplex formation within the RT6 family of aptamers, and they establish that the structural integrity of the simple quadruplex within R1T is less sensitive to ionic conditions, consistent with the inhibition data above.

Example 11

Figure 16:
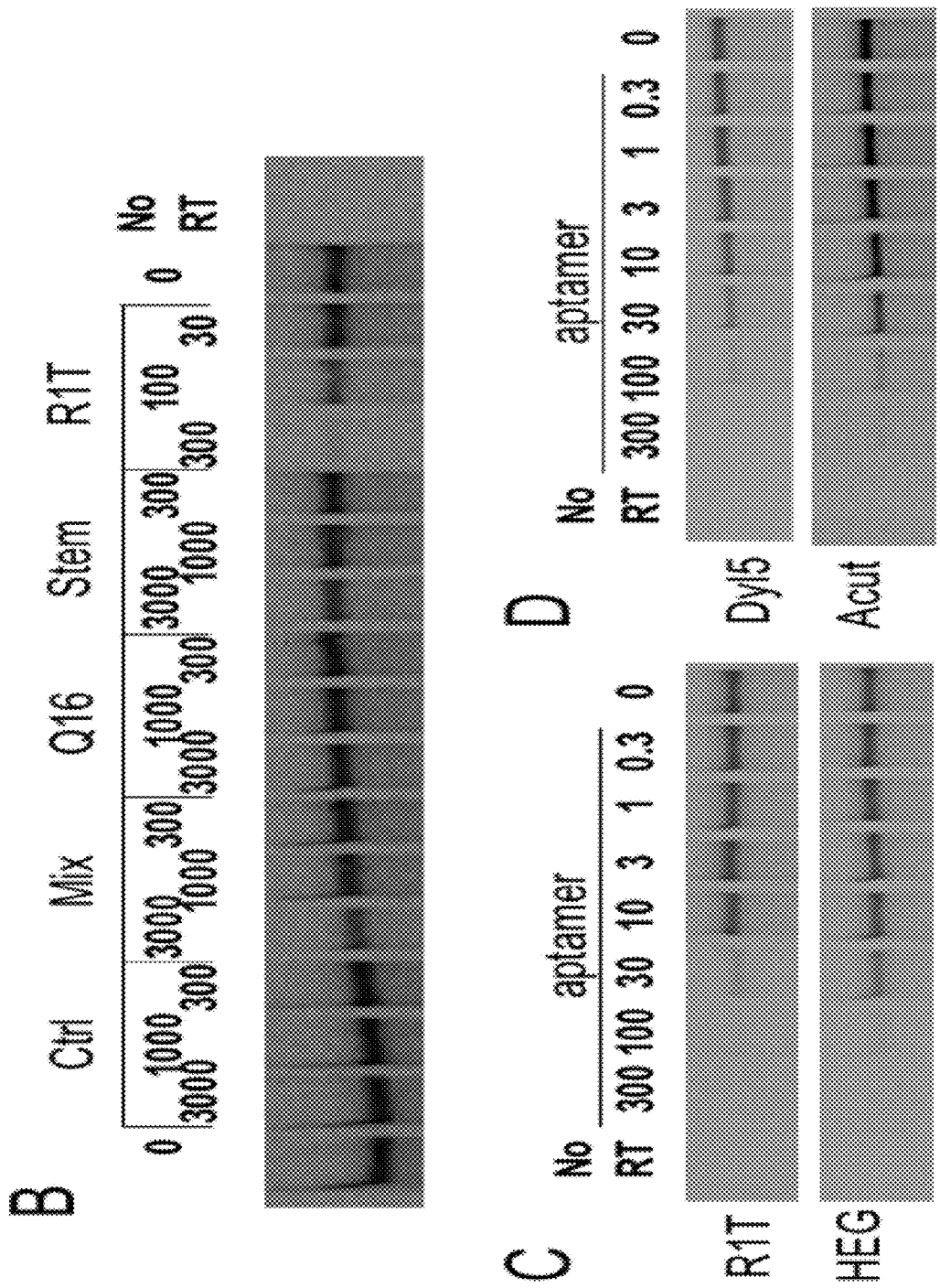
FIG. 16 Topological requirements. (A) Schematic diagrams of topological variants described in the text, assuming three-layer, parallel quadruplex stacks. (B) RT inhibition assays utilizing separated subdomains of R1T ('Stem' and 'Q16'). Inhibition is essentially eliminated when the two domains are not physically connected. 'Mix' refers to a 1:1 mixture of stem and Q16 oligos, each at the indicated concentrations. 'Ctrl' is an irrelevant control DNA: 5' d(GCGG-GACAATGGAGAGAGGG) (SEQ ID NO: 82). (C) RT inhibition assays in which the connector domain is replaced with HEG. (D) RT inhibition assays in which inter-module connection is via two strands, with 5' and 3' termini in the stem module (Dyl5) or between the second and third guanosine triplets (Acut).
Figure 16A:
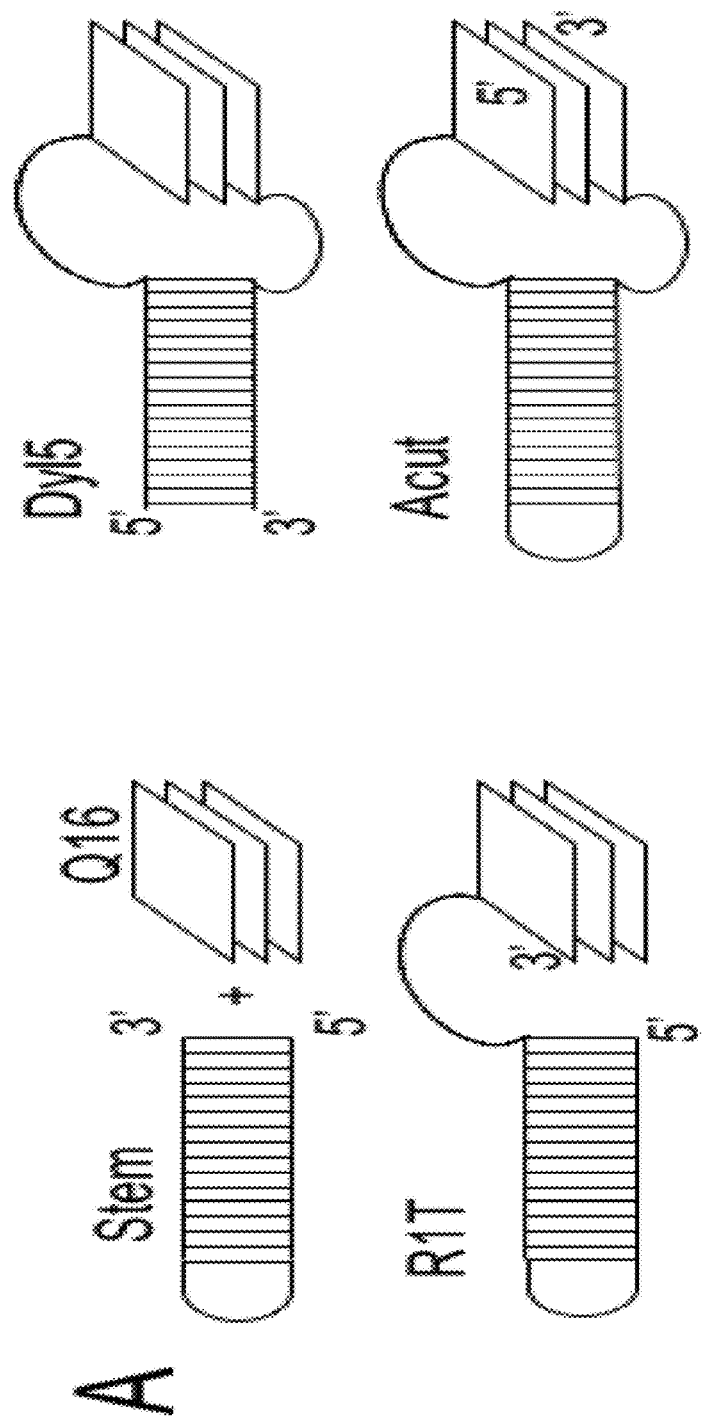

A Generic, Physical Connection is Required Between the Duplex and Quadruplex Modules RT inhibition was measured for several variants of R1T to determine the importance of the physical connection between the two structural modules (FIG. 16A). No inhibition was observed for a 28-nt oligo containing only the 5' stem-loop motif (stem), nor for a 16-nt oligo containing the (TGGG)4 quadruplex motif (Q16). Similarly, no inhibition was observed when both oligos were added simultaneously at a ratio of 1:1, even when their individual concentrations were increased to 3000 nM (FIG. 16B). A physical (covalent) connection between the DNA duplex and G-quadruplex is therefore required to effect inhibition.

The stem-loop and G-quadruplex elements within aptamers RT6, RT5 and RT47 are joined by single-stranded segments with the sequences TTA, CTT and CC, respectively, while in R1T the connector is TT. To determine the effect of varying this connector sequence, RT inhibition was measured for variants of R1T in which the connector was changed to several other sequences. Changing those two thymidines to two adenosines ($A_2$ connector in L6), or expanding it to four ($T_4$ in L3) or eight ($T_8$ in L4) thymidines had minimal effect on $IC_{50}$ values (13±1, 13±2 and 28±2 nM, respectively) (data not shown). To determine whether the negative charges or other nucleic acid-related features of these connector sequences are required for RT inhibition, the duplex and quadruplex modules were joined via HEG (FIG. 16C). The $IC_{50}$ value of the HEGlinked molecule (29±3 nM, HEG) is similar to that of the $T_8$-linked molecule. Thus, the primary role of the connector is to provide a physical connection between the two domains, rather than to provide a specific structural or functional role. However, there is an optimal range of lengths for the connector, as increasing it to T16 significantly weakened inhibition (L10, $IC_{50}$=120±6 nM).

Example 12

Topological Malleability of the Connectivity Between the Structural Elements

In all of the aptamer variants above, the two structural elements are connected via one flexible linker between the 3'-end of the helical element and the 5'-end of the quadruplex element. The 5'- and 3'-ends of the molecule are located, respectively, at the termini of the helical and quadruplex elements. Several variants of R1T were evaluated to determine whether alternative topologies are allowed. To accommodate relocating the 5' and 3' termini to other positions, the helical fragment was joined to the quadruplex by separate thymidine dinucleotides at each end of the quadruplex (FIG. 16A). For variants Dyl1, Dyl2, Dyl3 and Dyl5, the 5' and 3' termini lie within the original loop at the distal end of the helical element. The helical portions of these molecules contain a total of 15 bp, 19 bp, 22 by or 35 bp, including an internal mismatch derived from the original stem in RT6. All four variants strongly inhibit HIV-1 RT (e.g. $IC_{50}$=21.0±3.5 nM for Dyl5) (FIG. 16D). The 5' and 3' termini were next relocated to internal positions within the quadruplex (FIG. 16A). Placing the 3'-end after the second guano sine triplet (Acut, IC50=22±4 nM, FIG. 16D) yielded inhibition within a factor of two of the potency of R1T. Reversing the sequence within the central loop at the distal end of the helical element (Acutrev, IC50=33 f 2 nM) had only a slight effect on IC50. Inhibitory potency was further reduced when the 3'-end was placed after the first guanosine triplet (Bcut, IC50=48 f 1 nM) or after the third guanosine triplet (Ecut, IC50=99 f 2 nM), likely reflecting a destabilization of the quadruplex module. Potent inhibitors based on R1T can therefore be generated by joining the helical fragment and quadruplex by either a single or a double linker between the helical and quadruplex elements.

Example 13

Cross-Clade Inhibition of Divergent Primate Lentiviral RT's

The ssDNA aptamers studied here were originally selected to bind RT from HIV-1 strain BH10 (group M, subtype B). The inhibition studies presented above all utilize RT from the closely related HIV-1 strain HXB2 (six amino acid differences in 560 positions, preserving 98.9% identity). To define the phylogenetic breadth of inhibition by these bimodular ssDNA aptamers, DNA-dependent DNA polymerization was monitored for a panel of five RT variants from diverse primate lentiviral strains from within HIV-1 group M (average 92% identity with RT from BH10) and three from outside this group (see Held, D., et al. (2007) J. Virol., 81, 5375-5384). Aptamer SN was chosen for this analysis, as it was the most potent inhibitor among those studied here. All eight lentiviral RT's were inhibited. With the exception of the HIV-2 isolate, all IC50 values were (within error) within a factor of two of being identical to IC50 for inhibition of the subtype B enzyme. The SN aptamer (and related forms) are therefore highly promising reagents for developing broad-spectrum anti-HIV agents.

One skilled in the art would readily appreciate that the nucleic acids and methods described in the present disclosure are well adapted to carry out the objects and obtain the ends and advantages mentioned, as well as those inherent therein. The molecules and the methods, procedures, treatments, molecules, specific compounds described herein are presently representative of preferred embodiments, are exemplary, and are not intended as limitations on the scope of the present disclosure. It will be readily apparent to one skilled in the art that varying substitutions and modifications may be made to the present disclosure disclosed herein without departing from the scope and spirit of the present disclosure.

All patents and publications mentioned in the specification are indicative of the levels of those skilled in the art to which the present disclosure pertains. All patents and publications are herein incorporated by reference to the same extent as if each individual publication was specifically and individually indicated to be incorporated by reference.

REFERENCES

1. Abdool Karim, S. S., Abdool Karim, Q., Gouws, E. and Baxter, C. (2007) Global epidemiology of HIV-AIDS. Infect. Dis. Clin. North Am., 21, 1-17.
2. Ambrus, A., Chen, D., Dai, J., Jones, R. and Yang, D. (2005) Solution structure of the biologically relevant G-quadruplex element in the human c-MYC promoter. Implications for G-quadruplex stabilization. Biochemistry, 44, 2048-2058.
3. Andreola, M.-L., Pileur, F., Calmels, C., Ventura, M., TarragoLitvak, L., Toulme, J.-J. and Litvak, S. (2001) DNA aptamers selected against the HIV-1 RNase H display in vitro antiviral activity. Biochemistry, 40, 10087-10094.
4. Arnold, E., Jacobo-Molina, A., Nanni, R., Williams, R., Lu, X., Ding, J., Clark, A., Zhang, A., Ferris, A. L., Clark, P. et al. (1992) Structure of HIV-1 reverse transcriptase/DNA complex at 7A resolution showing active site locations. Nature, 357, 85-87.
5. Burge, S., Parkinson, G., Hazel, P., Todd, A. and Neidle, S. (2006) Quadruplex DNA: sequence, topology and structure. Nucleic Acids Res., 34, 5402-5415.
6. Burke, D. H., Scates, L. A., Andrews, K. and Gold, L. (1996) Bent pseudoknots and novel RNA inhibitors of type 1 human immunodeficiency virus (HIV-1) reverse transcriptase. J. Mol. Biol., 264, 650-666.
7. Chaloin, L., Lehmann, M. J., Sczakiel, G. and Restle, T. (2002) Endogenous expression of a high-affinity pseudoknot RNA aptamer supresses replication of HIV-1. Nucleic Acids Res., 30, 4001-4008.
8. Chen Y., et al., Antisense & Nucleic Acid Drug Development (2000), 10:415-420.
9. Cogoi, S, and Xodo, L. (2006) G-quadruplex formation within the promoter of the KRAS proto-oncogene and its effect on transcription. Nucleic Acids Res., 34, 2536-2549.
10. Christiansen, J., Kofod, M. and Nielsen, F. (1994) A guanosine quadruplex and two stable hairpins flank a major cleavage site in insulin-like growth factor II mRNA. Nucleic Acids Res., 22, 5709-5716.
11. Dai, J., Punchihewa, C., Ambrus, A., Chen, D., Jones, R. and Yang, D. (2007) Structure of the intramolecular human telomeric G-quadruplex in potassium solution: a novel adenine triple formation. Nucleic Acids Res., 35, 2440-2450.
12. de Soultrait, V., Lozach, P., Altmeyer, R., Tarrago-Litvak, L., Litvak, S, and Andreola, M. (2002) DNA aptamers derived from HIV-1 RNase H inhibitors are strong anti-integrase agents. J. Mol. Biol., 324, 195-203.
13. DeStefano, J. and Cristofaro, J. (2006) Selection of primer-template sequences that bind human immunodeficiency virus reverse transcriptase with high affinity. Nucleic Acids Res., 34, 130-139.
14. Ellington A. D. & Szostak J. W., Nature (1990), 346: 818-822.
15. Etzioni, S., Yafe, A., Khateb, S., Weisman-Shomer, P., Bengal, E. and Fry, M. (2005) Homodimeric MyoD preferentially binds tetraplex structures of regulatory sequences of muscle-specific genes. J. Biol. Chem., 280, 26805-26812.

16. Fisher, T. S., Joshi, P. and Prasad, V. R. (2002) Mutations that confer resistance to template-analog inhibitors of human immunodeficiency virus (HIV) type 1 reverse transcriptase lead to severe defects in HIV replication. J. Virol., 76, 4068-4072.
17. Fisher, T. S., Joshi, P. and Prasad, V. R. (2005) HIV-1 reverse transcriptase mutations that confer decreased in vitro susceptibility to anti-RT DNA aptamer RT1t49 Confer cross resistance to other anti-RT aptamers but not to standard RT inhibitors. AIDS Res Ther., 2, 8.
18. Girvan A. C., et al., Mol Cancer Ther (2006), 5(7):1790-1799
19. Guo, K., Pourpak, A., Beetz-Rogers, K., Gokhale, V., Sun, D. and Hurley, L. (2007) Formation of pseudosymmetrical G-quadruplex and i-motif structures in the proximal promoter region of the RET oncogene. J. Am. Chem. Soc., 129, 10220-10228.
20. Haider, S., Parkinson, G. and Neidle, S. (2002) Crystal structure of the potassium form of an Oxytricha nova G-quadruplex. J. Mol. Biol., 320, 189-200.
21. Halder, K., Mathur, V., Chugh, D., Verma, A. and Chowdhury, S. (2005) Quadruplex-duplex competition in the nuclease hypersensitive element of human c-myc promoter: C to T mutation in C-rich strand enhances duplex association. Biochem. Biophys. Res. Commun., 327, 49-56.
22. Hariri, S, and McKenna, M. T. (2007) Epidemiology of human immunodeficiency virus in the United States. Clin. Microbiol. Rev., 20, 478-488.
23. Held, D., Kissel, J., Patterson, J., Nickens, D. and Burke, D. (2006) HIV-1 inactivation by nucleic acid aptamers. Front Biosci., 11, 89-112.
24. Held, D., Kissel, J., Thacker, S., Michalowski, D., Saran, D., Ji, J., Hardy, R., Rossi, J. and Burke, D. (2007) Cross-clade inhibition of recombinant HIV-1, HIV-2 and SIVcpz reverse transcriptases by RNA pseudoknot aptamers. J. Virol., 81, 5375-5384.
25. Hershman, S., Chen, Q., Lee, J., Kozak, M., Yue, P., Wang, L. and Johnson, F. (2007) Genomic distribution and functional analyses of potential G-quadruplex-forming sequences in Saccharomyces cerevisiae. Nucleic Acids Res., 36, 144-156.
26. Held, D., Kissel, J., Saran, D., Michalowski, D. and Burke, D. (2006) Differential susceptibility of HIV-1 reverse transcriptase to inhibition by RNA aptamers in enzymatic reactions monitoring specific steps during genome replication. J. Biol. Chem., 281, 25712-25722.
27. Huang, H., Chopra, R., Verdine, G. and Harrison, S. (1998) Structure of a covalently trapped catalytic complex of HIV-1 reverse transcriptase: implications for drug resistance. Science, 282, 1669-1675.
28. Kissel, J., Held, D., Hardy, R. and Burke, D. (2007) Single-stranded DNA aptamer RT1t49 inhibits RT polymerase and RNase H functions of HIV type 1, HIV type 2, and SIVCPZ RTs. AIDS Res. Hum. Retroviruses, 23, 699-708.
29. Kissel, J., Held, D., Hardy, R. and Burke, D. (2007) Active site binding and sequence requirements for inhibition of HIV-1 reverse transcriptase by the RT1 family of single-stranded DNA aptamers. Nucleic Acids Res., 35, 5039-5050.
30. Jacobo-Molina, A., Ding, J., Nanni, R. G., Clark, A. D. J., Lu, X., Tantillo, C., Williams, R. L., Kamer, G., Ferris, A. L., Clark, P. et al. (1993) Crystal structure of human immunodeficiency virus type 1 reverse transcriptase complexed with double-stranded DNA at 3.0 A° resolution shows bent DNA. Proc. Natl. Acad. Sci., 90, 6320-6324.
31. Jaeger, J., Restle, T. and Steitz, T. A. (1998) The structure of HIV-1 reverse transcriptase complexed with an RNA pseudoknot inhibitor. EMBO J., 17, 4535-4542.
32. Jing, N., Rando, R., Pommier, Y. and Hogan, M. (1997) Ion selective folding of loop domains in a potent anti-HIV oligonucleotide. Biochemistry, 36, 12498-12505.
33. Jing N., et al., Biochemistry (2002), 41:5397-5403.
34. Jing, N., Marchand, C., Liu, J., Mitra, R., Hogan, M. and Pommier, Y. (2000) Mechanism of inhibition HIV-1 integrase by G-tetrad forming oligonucleotides in vitro. J. Biol. Chem., 275, 21460-21467.
35. Jing, N., De Clercq, E., Rando, R., Pallansch, L., Lackman-Smith, C., Lee, S, and Hogan, M. (2000) Stability-activity relationships of a family of G-tetrad forming oligonucleotides as potent HIV inhibitors. J. Biol. Chem., 275, 3421-3430.
36. Jing, N., Gao, X., Rando, R. and Hogan, M. (1997) Potassium-induced loop conformational transition of a potent anti-HIV oligonucleotide. J. Biomol. Struct. Dyn., 15, 573-585.
37. Jing, N. and Hogan, M. (1998) Structure-activity of tetrad forming oligonucleotides as a potential anti-HIV integrase therapeutic drug. J. Biol. Chem., 273, 34992-34999.
38. Joshi, P. and Prasad, V. R. (2002) Potent inhibition of human immunodeficiency virus type 1 replication by template analog reverse transcriptase inhibitors derived by SELEX (systematic evolution of ligands by exponential enrichment). J. Virol., 76, 6545-6557.
39. Joshi, P. J., North, T. W. and Prasad, V. R. (2005) Aptamers directed to HIV-1 reverse transcriptase display greater efficacy over small hairpin RNAs targeted to viral RNA in blocking HIV-1 replication Mol. Ther., 11, 677-686.
40. Kohlstaedt, L. A., Wang, J., Friedman, J. M., Rice, P. A. and Steitz, T. A. (1992) Crystal structure at 3.5 A° resolution of HIV-1 reverse transcriptase complexed with an inhibitor. Science, 256, 1783-1790.
41. Kvaratskhelia, M., Miller, J. T., Budihas, S. R., Pannell, L. K. and Le Grice, S. F. (2002) Identification of specific HIV-1 reverse transcriptase contacts to the viral RNA: tRNA complex by mass spectrometry and a primary amine selective reagent. Proc. Natl. Acad. Sci. USA, 99, 15988-15993.
42. Lyonnais, S., Hounsou, C., Teulade-Fichou, M.-P., Jeusset, J., Le Cam, E. and Mirambeau, G. (2002) G-quartets assembly within a G-rich DNA flap. a possible event at the center of the HIV-1 genome. Nucleic Acid Res., 30, 5276-5283.
43. Macaya, R. F., Schultze, P., Smith, F. W., Roe, J. A. and Feigon, J. (1993) Thrombin-binding DNA aptamer forms a unimolecular quadruplex structure in solution. Proc. Natl. Acad. Sci., 90, 3745-3749.
44. Mathews, D., Sabina, J., Zuker, M. and Turner, D. (1999) Expanded sequence dependence of thermodynamic parameters improves prediction of RNA secondary structure. J. Mol. Biol., 288, 911-940.
45. Mazumder, A., Neamati, N., Ojwang, J., Sunder, S., Rando, R. and Pommier, Y. (1996) Inhibition of the human immunodeficiency virus type 1 integrase by guanosine quartet structures. Biochemistry, 35, 13762-13771.
46. Mosing, R., Mendonsa, S, and Bowser, M. (2005) Capillary electrophoresis-SELEX selection of aptamers with affinity for HIV-1 reverse transcriptase. Anal. Chem., 77, 6107-6112.
47. Neidle & Balasubramanian (Eds.) (2006), Quadruplex Nucleic Acids (ISBN 0854043748).
48. Phan, A., Kuryavyi, V., Ma, J.-B., Faure, A., Andre'ola, M.-L. and Patel, D. (2005) An interlocked dimeric parallel-stranded DNA quadruplex: a potent inhibitor of HIV-1 integrase. Proc. Natl. Acad. Sci., USA, 102, 634-639.
49. Qin, Y., Rezler, E., Gokhale, V., Sun, D. and Hurley, L. (2007) Characterization of the G-quadruplexes in the duplex nuclease hypersensitive element of the PDGF-A promoter and modulation of PDGF-A promoter activity by TMPyP4. Nucleic Acids Res., 35, 7698-7713.
50. Rachwal, P., Findlow, I., Werner, J., Brown, T. and Fox, K. (2007) Intramolecular DNA quadruplexes with different arrangements of short and long loops. Nucleic Acid Res., 35, 4214-4222.
51. Rachwal, P., Brown, T. and Fox, K. (2007) Effect of G-tract length on the topology and stability of intramolecular DNA quadruplexes. Biochemistry, 46, 3036-3044.
52. Risitano, A. and Fox, K. (2004) Influence of loop size on the stability of intramolecular DNA quadruplexes. Nucleic Acid Res., 32, 2598-2606.
53. Risitano, A. and Fox, K. (2003) Stability of intramolecular DNA quadruplex: comparison with DNA duplexes. Biochemistry, 42, 6507-6513.
54. Sarafianos, S. G., Das, K., Tantillo, T., Clark, A. D. J., Ding, J., Whitcomb, J. M., Boyer, P. L., Hughes, S. H. and Arnold, E. T. (2001) Crystal structure of HIV-1 reverse transcriptase in complex with a polypurine tract RNA: DNA. EMBO J., 20, 1449-1461.
55. Schneider, D. J., Feigon, J., Hostomsky, Z. and Gold, L. (1995) High-affinity ssDNA inhibitors of the reverse transcriptase of type 1 human immunodeficiency virus. Biochem., 34, 9599-9610.
56. Shafer R. H. & Smirnov I., Biopolimers (2001), 56:209-211.
57. Simonsson, T. (2001) G-quadruplex DNA structures-variations on a theme. Biol. Chem., 382, 621-628.
58. Somasunderam, A., Ferguson, M. R., Rojo, D. R., Thiviyanathan, V., Li, X., O'Brien, W. A. and Gorenstein, D. G. (2005) Combinatorial selection, inhibition, and antiviral activity of DNA thioaptamers targeting the RNase H domain of HIV-1 reverse transcriptase. Biochemistry, 44, 10388-10395.
59. Teng, Y., Girvan, A., Casson, L., Pierce, W. J., Qian, M., Thomas, S, and Bates, P. (2007) AS1411 alters the localization of a complex containing protein arginine methyltransferase 5 and nucleolin. Cancer Res., 67, 10491-10500.
60. Tohl, J. and Eimer, W. (1996) Interaction energies and dynamics of alkali and alkaline-earth cations in quadruplex-DNA-structures. J. Mol. Model., 2, 327-329.
61. Travascio P., et al., J Am Chem Soc (2001), 123:1337-1348.
62. Tuerk C. & Gold L., Science (1990), 249 (4968): 505-510.
63. Tuerk, C., MacDougal, S, and Gold, L. (1992) RNA pseudoknots that inhibit human immunodeficiency virus type 1 reverse transcriptase. Proc. Natl. Acad. Sci., 89, 6988-6992.
64. Tuske, S., Sarafianos, S., Clark, A. J., Ding, J., Naeger, L., White, K., Miller, M., Gibbs, C., Boyer, P., Clark, P. et al. (2004) Structures of HIV-1 RT-DNA complexes before and after incorporation of the anti-AIDS drug tenofovir. Nat. Struct. Mol. Biol., 11, 469-474.
65. Ulrich H., et al., Comb Chem high Throughput Screen (2006), 9 (8):619-632.
66. UNReport. (2007) HIV infection on the rise worldwide: U.N. report. Clin. Infect. Dis., 44, 3-4.
67. Zuker, M. (2003) Mfold web server for nucleic acid folding and hybridization prediction. Nucleic Acids Res., 31, 3406-3415.

What is claimed is:

1. An isolated nucleic acid molecule comprising a double-helical domain and a G-quadruplex domain coupled by a linker domain, wherein the nucleic acid molecule binds a primate lenitviral reverse transcriptase polypeptide having the sequence SEQ ID. NO: 1, the isolated nucleic acid molecule having the sequence of SEQ ID NO.

2. The isolated nucleic acid molecule of claim 1 wherein the nucleic acid molecule comprises a hairpin loop structure comprising a 3' end of the double helical domain coupled to the linker domain, and the linker domain coupled to a 5' end of the G-quadruplex domain.

3. The isolated nucleic acid molecule of claim 1 wherein the nucleic acid molecule comprises a 3' end and a 5' end of the double helical domain coupled to the linker domain, and the linker domain coupled to a 5' end and to a 3' end of the G-quadruplex domain.

4. The isolated nucleic acid molecule of claim 1 wherein the G-quadruplex domain comprises a plurality of loops.

5. The isolated nucleic acid molecule of claim 1, wherein the nucleic acid molecule is labeled with a detectable marker.

6. The isolated nucleic acid molecule of claim 1 conjugated to a polypeptide.

7. The isolated nucleic acid molecule of claim 6 wherein the polypeptide is a carrier peptide or a cell-penetrating polypeptide.

8. A vector comprising the isolated nucleic acid molecule of claim 1.

9. A host cell comprising the vector of claim 8.

10. The isolated nucleic acid molecule of claim 1, wherein the nucleic acid molecule is a ribonucleic acid wherein each thymidine (T) in the sequence is replaced by a uridine (U).

11. A vector comprising the isolated nucleic acid molecule of claim 10.

12. A host cell comprising the vector of claim 11.

13. The isolated nucleic acid molecule of claim 10, wherein the nucleic acid molecule is labeled with a detectable marker.

14. The isolated nucleic acid molecule of claim 10, conjugated to a polypeptide.

15. The isolated nucleic acid molecule of claim 14, wherein the polypeptide is a carrier peptide or a cell-penetrating polypeptide.

16. A kit for inhibiting a primate lentiviral reverse transcriptase, the kit comprising at least one nucleic acid molecule of claim 1 and written material describing methods for its use to inhibit a primate lentiviral reverse transcriptase.

17. The kit according to claim 16 further comprising at least one reagent for examining inhibition of the lentiviral reverse transcriptase polypeptide activity.

18. The kit according to claim 16 wherein the at least one reagent comprises a labeled DNA primer and a DNA template corresponding to a portion of a nucleotide sequence encoding the lentiviral reverse transcriptase polypeptide.

19. The kit according to claim 16 wherein the nucleic acid molecule is labeled with a detectable marker.

* * * * *

UNITED STATES PATENT AND TRADEMARK OFFICE
CERTIFICATE OF CORRECTION

PATENT NO. : 8,030,475 B2  
APPLICATION NO. : 12/471166  
DATED : October 4, 2011  
INVENTOR(S) : Daniel Michalowski et al.

Page 1 of 1

It is certified that error appears in the above-identified patent and that said Letters Patent is hereby corrected as shown below:

Col. 89, Claim 1, last line: "SEQ ID NO." should read -- SEQ ID No. 15. --

Signed and Sealed this
Sixth Day of December, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 8,030,475 B2 | |
| APPLICATION NO. | : 12/471166 | |
| DATED | : October 4, 2011 | |
| INVENTOR(S) | : Daniel Michalowski et al. | |

It is certified that error appears in the above-identified patent and that said Letters Patent is hereby corrected as shown below:

Cover Page, item (*) Notice: "This patent is subject to a terminal disclaimer" should be deleted.

Signed and Sealed this
Twenty-fourth Day of January, 2012

David J. Kappos
*Director of the United States Patent and Trademark Office*

SEQUENCE LISTING

```
<160> NUMBER OF SEQ ID NOS: 93

<210> SEQ ID NO 1
<211> LENGTH: 560
<212> TYPE: PRT
<213> ORGANISM: Human immunodeficiency virus type 1

<400> SEQUENCE: 1

Pro Ile Ser Pro Ile Glu Thr Val Pro Val Lys Leu Lys Pro Gly Met
1               5                   10                  15

Asp Gly Pro Lys Val Lys Gln Trp Pro Leu Thr Glu Glu Lys Ile Lys
            20                  25                  30

Ala Leu Val Glu Ile Cys Thr Glu Met Glu Lys Glu Gly Lys Ile Ser
        35                  40                  45

Lys Ile Gly Pro Glu Asn Pro Tyr Asn Thr Pro Val Phe Ala Ile Lys
    50                  55                  60

Lys Lys Asp Ser Thr Lys Trp Arg Lys Leu Val Asp Phe Arg Glu Leu
65                  70                  75                  80

Asn Lys Arg Thr Gln Asp Phe Trp Glu Val Gln Leu Gly Ile Pro His
                85                  90                  95

Pro Ala Gly Leu Lys Lys Lys Ser Val Thr Val Leu Asp Val Gly
            100                 105                 110

Asp Ala Tyr Phe Ser Val Pro Leu Asp Glu Asp Phe Arg Lys Tyr Thr
        115                 120                 125

Ala Phe Thr Ile Pro Ser Ile Asn Asn Glu Thr Pro Gly Ile Arg Tyr
    130                 135                 140
```

```
Gln Tyr Asn Val Leu Pro Gln Gly Trp Lys Gly Ser Pro Ala Ile Phe
145                 150                 155                 160

Gln Ser Ser Met Thr Lys Ile Leu Glu Pro Phe Lys Lys Gln Asn Pro
                165                 170                 175

Asp Ile Val Ile Tyr Gln Tyr Met Asp Asp Leu Tyr Val Gly Ser Asp
            180                 185                 190

Leu Glu Ile Gly Gln His Arg Thr Lys Ile Glu Glu Leu Arg Gln His
        195                 200                 205

Leu Leu Arg Trp Gly Leu Thr Thr Pro Asp Lys Lys His Gln Lys Glu
    210                 215                 220

Pro Pro Phe Leu Trp Met Gly Tyr Glu Leu His Pro Asp Lys Trp Thr
225                 230                 235                 240

Val Gln Pro Ile Val Leu Pro Glu Lys Asp Ser Trp Thr Val Asn Asp
                245                 250                 255

Ile Gln Lys Leu Val Gly Lys Leu Asn Trp Ala Ser Gln Ile Tyr Pro
            260                 265                 270

Gly Ile Lys Val Arg Gln Leu Cys Lys Leu Leu Arg Gly Thr Lys Ala
        275                 280                 285

Leu Thr Glu Val Ile Pro Leu Thr Glu Glu Ala Glu Leu Glu Leu Ala
    290                 295                 300

Glu Asn Arg Glu Ile Leu Lys Glu Pro Val His Gly Val Tyr Tyr Asp
305                 310                 315                 320

Pro Ser Lys Asp Leu Ile Ala Glu Ile Gln Lys Gln Gly Gln Gly Gln
                325                 330                 335

Trp Thr Tyr Gln Ile Tyr Gln Glu Pro Phe Lys Asn Leu Lys Thr Gly
            340                 345                 350

Lys Tyr Ala Arg Met Arg Gly Ala His Thr Asn Asp Val Lys Gln Leu
        355                 360                 365

Thr Glu Ala Val Gln Lys Ile Thr Thr Glu Ser Ile Val Ile Trp Gly
    370                 375                 380

Lys Thr Pro Lys Phe Lys Leu Pro Ile Gln Lys Glu Thr Trp Glu Thr
385                 390                 395                 400

Trp Trp Thr Glu Tyr Trp Gln Ala Thr Trp Ile Pro Glu Trp Glu Phe
                405                 410                 415

Val Asn Thr Pro Pro Leu Val Lys Leu Trp Tyr Gln Leu Glu Lys Glu
            420                 425                 430

Pro Ile Val Gly Ala Glu Thr Phe Tyr Val Asp Gly Ala Ala Asn Arg
        435                 440                 445

Glu Thr Lys Leu Gly Lys Ala Gly Tyr Val Thr Asn Lys Gly Arg Gln
    450                 455                 460

Lys Val Val Pro Leu Thr Asn Thr Thr Asn Gln Lys Thr Glu Leu Gln
465                 470                 475                 480

Ala Ile Tyr Leu Ala Leu Gln Asp Ser Gly Leu Glu Val Asn Ile Val
                485                 490                 495

Thr Asp Ser Gln Tyr Ala Leu Gly Ile Ile Gln Ala Gln Pro Asp Lys
            500                 505                 510

Ser Glu Ser Glu Leu Val Asn Gln Ile Ile Glu Gln Leu Ile Lys Lys
        515                 520                 525

Glu Lys Val Tyr Leu Ala Trp Val Pro Ala His Lys Gly Ile Gly Gly
    530                 535                 540

Asn Glu Gln Val Asp Lys Leu Val Ser Ala Gly Ile Arg Lys Ile Leu
545                 550                 555                 560
```

<210> SEQ ID NO 2
<211> LENGTH: 560
<212> TYPE: PRT
<213> ORGANISM: Human immunodeficiency virus type 1

<400> SEQUENCE: 2

```
Pro Ile Ser Pro Ile Glu Thr Val Pro Val Lys Leu Lys Pro Gly Met
1               5                   10                  15

Asp Gly Pro Lys Val Lys Gln Trp Pro Leu Thr Glu Glu Lys Ile Lys
            20                  25                  30

Ala Leu Val Glu Ile Cys Thr Glu Met Glu Lys Glu Gly Lys Ile Ser
        35                  40                  45

Lys Ile Gly Pro Glu Asn Pro Tyr Asn Thr Pro Val Phe Ala Ile Lys
    50                  55                  60

Lys Lys Asp Ser Thr Lys Trp Arg Lys Leu Val Asp Phe Arg Glu Leu
65                  70                  75                  80

Asn Lys Arg Thr Gln Asp Phe Trp Glu Val Gln Leu Gly Ile Pro His
                85                  90                  95

Pro Ala Gly Leu Lys Lys Lys Lys Ser Val Thr Val Leu Asp Val Gly
            100                 105                 110

Asp Ala Tyr Phe Ser Val Pro Leu Asp Glu Asp Phe Arg Lys Tyr Thr
        115                 120                 125

Ala Phe Thr Ile Pro Ser Ile Asn Asn Glu Thr Pro Gly Ile Arg Tyr
    130                 135                 140

Gln Tyr Asn Val Leu Pro Gln Gly Trp Lys Gly Ser Pro Ala Ile Phe
145                 150                 155                 160

Gln Ser Ser Met Thr Lys Ile Leu Glu Pro Phe Arg Lys Gln Asn Pro
                165                 170                 175

Asp Ile Val Ile Tyr Gln Tyr Met Asp Asp Leu Tyr Val Gly Ser Asp
            180                 185                 190

Leu Glu Ile Gly Gln His Arg Thr Lys Ile Glu Glu Leu Arg Gln His
        195                 200                 205

Leu Leu Arg Trp Gly Leu Thr Thr Pro Asp Lys Lys His Gln Lys Glu
    210                 215                 220

Pro Pro Phe Leu Trp Met Gly Tyr Glu Leu His Pro Asp Lys Trp Thr
225                 230                 235                 240

Val Gln Pro Ile Val Leu Pro Glu Lys Asp Ser Trp Thr Val Asn Asp
                245                 250                 255

Ile Gln Lys Leu Val Gly Lys Leu Asn Trp Ala Ser Gln Ile Tyr Pro
            260                 265                 270

Gly Ile Lys Val Arg Gln Leu Cys Lys Leu Leu Arg Gly Thr Lys Ala
        275                 280                 285

Leu Thr Glu Val Ile Pro Leu Thr Glu Glu Ala Glu Leu Glu Leu Ala
    290                 295                 300

Glu Asn Arg Glu Ile Leu Lys Glu Pro Val His Gly Val Tyr Tyr Asp
305                 310                 315                 320

Pro Ser Lys Asp Leu Ile Ala Glu Ile Gln Lys Gln Gly Gln Gly Gln
                325                 330                 335

Trp Thr Tyr Gln Ile Tyr Gln Glu Pro Phe Lys Asn Leu Lys Thr Gly
            340                 345                 350

Lys Tyr Ala Arg Met Arg Gly Ala His Thr Asn Asp Val Lys Gln Leu
        355                 360                 365

Thr Glu Ala Val Gln Lys Ile Thr Thr Glu Ser Ile Val Ile Trp Gly
    370                 375                 380

Lys Thr Pro Lys Phe Lys Leu Pro Ile Gln Lys Glu Thr Trp Glu Thr
```

```
                385                 390                 395                 400
Trp Trp Thr Glu Tyr Trp Gln Ala Thr Trp Ile Pro Glu Trp Glu Phe
                    405                 410                 415

Val Asn Thr Pro Pro Leu Val Lys Leu Trp Tyr Gln Leu Glu Lys Glu
            420                 425                 430

Pro Ile Val Gly Ala Glu Thr Phe Tyr Val Asp Gly Ala Ala Asn Arg
        435                 440                 445

Glu Thr Lys Leu Gly Lys Ala Gly Tyr Val Thr Asn Arg Gly Arg Gln
    450                 455                 460

Lys Val Val Thr Leu Thr Asp Thr Thr Asn Gln Lys Thr Glu Leu Gln
465                 470                 475                 480

Ala Ile Tyr Leu Ala Leu Gln Asp Ser Gly Leu Glu Val Asn Ile Val
                485                 490                 495

Thr Asp Ser Gln Tyr Ala Leu Gly Ile Ile Gln Ala Gln Pro Asp Gln
            500                 505                 510

Ser Glu Ser Glu Leu Val Asn Gln Ile Ile Glu Gln Leu Ile Lys Lys
        515                 520                 525

Glu Lys Val Tyr Leu Ala Trp Val Pro Ala His Lys Gly Ile Gly Gly
    530                 535                 540

Asn Glu Gln Val Asp Lys Leu Val Ser Ala Gly Ile Arg Lys Val Leu
545                 550                 555                 560

<210> SEQ ID NO 3
<211> LENGTH: 560
<212> TYPE: PRT
<213> ORGANISM: Human immunodeficiency virus type 1

<400> SEQUENCE: 3

Pro Ile Ser Pro Ile Glu Thr Val Pro Val Lys Leu Lys Pro Gly Met
1               5                   10                  15

Asp Gly Pro Lys Val Lys Gln Trp Pro Leu Thr Glu Glu Lys Ile Lys
            20                  25                  30

Ala Leu Thr Glu Ile Cys Lys Glu Met Glu Lys Glu Gly Lys Ile Ser
        35                  40                  45

Lys Ile Gly Pro Glu Asn Pro Tyr Asn Thr Pro Val Phe Ala Ile Lys
    50                  55                  60

Lys Lys Asp Ser Thr Lys Trp Arg Lys Leu Val Asp Phe Arg Glu Leu
65                  70                  75                  80

Asn Lys Arg Thr Gln Asp Phe Trp Glu Val Gln Leu Gly Ile Pro His
                85                  90                  95

Pro Ala Gly Leu Lys Lys Lys Ala Val Thr Val Leu Asp Val Gly
            100                 105                 110

Asp Ala Tyr Phe Ser Val Pro Leu His Glu Asp Phe Arg Lys Tyr Thr
        115                 120                 125

Ala Phe Thr Ile Pro Ser Thr Asn Asn Glu Thr Pro Gly Val Arg Tyr
    130                 135                 140

Gln Tyr Asn Val Leu Pro Gln Gly Trp Lys Gly Ser Pro Ala Ile Phe
145                 150                 155                 160

Gln Ser Ser Met Thr Lys Ile Leu Glu Pro Phe Arg Ser Lys Asn Thr
                165                 170                 175

Glu Leu Ile Ile Tyr Gln Tyr Met Asp Asp Leu Tyr Val Gly Ser Asp
            180                 185                 190

Leu Glu Ile Ser Gln His Arg Val Lys Ile Glu Glu Leu Arg Ala His
        195                 200                 205

Leu Leu Lys Trp Gly Phe Tyr Thr Pro Asp Lys Lys His Gln Lys Glu
```

```
                    210                 215                 220
Pro Pro Phe Leu Trp Met Gly Tyr Glu Leu His Pro Asp Lys Trp Thr
225                 230                 235                 240

Val Gln Pro Ile Lys Leu Pro Glu Lys Asp Ser Trp Thr Val Asn Asp
                    245                 250                 255

Ile Gln Lys Leu Val Gly Lys Leu Asn Trp Ala Ser Gln Ile Tyr Ala
                260                 265                 270

Gly Ile Lys Val Lys Gln Leu Cys Lys Leu Leu Arg Gly Ala Lys Ala
                275                 280                 285

Leu Thr Asp Ile Val Thr Leu Thr Lys Glu Ala Glu Leu Glu Leu Glu
290                 295                 300

Glu Asn Arg Glu Ile Leu Lys Thr Pro Val His Gly Val Tyr Tyr Asp
305                 310                 315                 320

Pro Ser Lys Asp Leu Ile Ala Glu Ile Gln Lys Gln Gly Gln Asp Gln
                325                 330                 335

Trp Thr Tyr Gln Ile Tyr Gln Glu Pro Phe Lys Asn Leu Lys Thr Gly
                340                 345                 350

Lys Tyr Ala Lys Arg Arg Ser Thr His Thr Asn Asp Ile Lys Gln Leu
                355                 360                 365

Thr Glu Ala Val Gln Lys Ile Thr Met Glu Ser Ile Val Ile Trp Gly
370                 375                 380

Lys Thr Pro Lys Phe Lys Leu Pro Ile Gln Lys Glu Thr Trp Glu Thr
385                 390                 395                 400

Trp Trp Ala Glu Tyr Trp Gln Ala Thr Trp Ile Pro Glu Trp Glu Phe
                405                 410                 415

Val Asn Thr Pro Pro Leu Val Lys Leu Trp Tyr Gln Leu Glu Lys Glu
                420                 425                 430

Pro Ile Ala Gly Ala Glu Thr Phe Tyr Val Asp Gly Ala Ala Asn Arg
                435                 440                 445

Glu Thr Lys Leu Gly Lys Ala Gly Tyr Val Thr Asp Arg Gly Arg Gln
                450                 455                 460

Lys Ile Val Ser Leu Thr Glu Thr Thr Asn Gln Lys Thr Glu Leu His
465                 470                 475                 480

Ala Ile Tyr Leu Ala Leu Gln Asp Ser Gly Leu Glu Val Asn Ile Val
                485                 490                 495

Thr Asp Ser Gln Tyr Ala Leu Gly Ile Ile Gln Ala Gln Pro Glu Arg
                500                 505                 510

Ser Glu Ser Glu Ile Val Asn Gln Ile Ile Glu Lys Leu Ile Glu Lys
                515                 520                 525

Glu Arg Val Tyr Leu Ser Trp Val Pro Ala His Lys Gly Ile Gly Gly
                530                 535                 540

Asn Glu Gln Val Asp Lys Leu Val Ser Ser Gly Ile Arg Lys Val Leu
545                 550                 555                 560

<210> SEQ ID NO 4
<211> LENGTH: 560
<212> TYPE: PRT
<213> ORGANISM: Human immunodeficiency virus type 1

<400> SEQUENCE: 4

Pro Ile Ser Pro Ile Asp Thr Val Pro Val Lys Leu Lys Pro Gly Met
1               5                   10                  15

Asp Gly Pro Lys Val Lys Gln Trp Pro Leu Thr Glu Glu Lys Ile Lys
                20                  25                  30

Ala Leu Thr Glu Ile Cys Thr Glu Met Glu Lys Glu Gly Lys Ile Ser
```

```
                35                  40                  45
Arg Ile Gly Pro Glu Asn Pro Tyr Asn Thr Pro Ile Phe Ala Ile Lys
 50                  55                  60

Lys Lys Asp Ser Thr Lys Trp Arg Lys Leu Val Asp Phe Arg Glu Leu
 65                  70                  75                  80

Asn Lys Arg Thr Gln Asp Phe Trp Glu Val Gln Leu Gly Ile Pro His
                 85                  90                  95

Pro Ala Gly Leu Lys Lys Lys Ser Val Thr Val Leu Asp Val Gly
            100                 105                 110

Asp Ala Tyr Phe Ser Val Pro Leu Cys Glu Asp Phe Arg Lys Tyr Thr
            115                 120                 125

Ala Phe Thr Ile Pro Ser Ile Asn Asn Glu Thr Pro Gly Ile Arg Tyr
    130                 135                 140

Gln Tyr Asn Val Leu Pro Gln Gly Trp Lys Gly Ser Pro Ala Ile Phe
145                 150                 155                 160

Gln Ser Ser Met Thr Lys Ile Leu Asp Pro Phe Arg Lys Gln Asn Pro
                165                 170                 175

Glu Met Val Ile Tyr Gln Tyr Met Asp Asp Leu Tyr Val Gly Ser Asp
            180                 185                 190

Leu Glu Ile Gly Gln His Arg Thr Lys Ile Glu Glu Leu Arg Glu His
        195                 200                 205

Leu Leu Lys Trp Gly Phe Thr Thr Pro Asp Lys Lys His Gln Lys Glu
210                 215                 220

Pro Pro Phe Leu Trp Met Gly Tyr Glu Leu His Pro Asp Lys Trp Thr
225                 230                 235                 240

Val Gln Pro Ile Met Leu Pro Glu Lys Glu Ser Trp Thr Val Asn Asp
                245                 250                 255

Ile Gln Lys Leu Val Gly Lys Leu Asn Trp Ala Ser Gln Ile Tyr Pro
            260                 265                 270

Gly Ile Arg Val Lys Gln Leu Cys Lys Cys Leu Arg Gly Ala Lys Ala
        275                 280                 285

Leu Thr Glu Val Ile Pro Leu Thr Glu Glu Ala Glu Leu Glu Leu Ala
290                 295                 300

Glu Asn Arg Glu Ile Leu Lys Glu Pro Val His Gly Val Tyr Tyr Asp
305                 310                 315                 320

Pro Ser Lys Asp Leu Ile Ala Glu Ile Gln Lys Gln Gly Gln Asp Pro
                325                 330                 335

Trp Thr Tyr Gln Ile Tyr Gln Glu Gln Tyr Lys Asn Leu Lys Thr Gly
            340                 345                 350

Lys Tyr Ala Lys Thr Arg Gly Thr His Thr Asn Asp Val Lys Gln Leu
        355                 360                 365

Thr Glu Ala Val Gln Lys Ile Ala Gln Glu Cys Ile Val Ile Trp Gly
370                 375                 380

Lys Thr Pro Lys Phe Arg Leu Pro Ile Gln Lys Glu Thr Trp Glu Thr
385                 390                 395                 400

Trp Trp Thr Glu Tyr Trp Gln Ala Thr Trp Pro Glu Trp Glu Phe
                405                 410                 415

Val Asn Thr Pro Pro Leu Val Lys Leu Trp Tyr Gln Leu Glu Lys Glu
            420                 425                 430

Pro Ile Val Gly Ala Glu Thr Phe Tyr Val Asp Gly Ala Ala Asn Arg
        435                 440                 445

Glu Thr Lys Leu Gly Lys Ala Gly Tyr Val Thr Asp Lys Gly Arg Gln
450                 455                 460
```

```
Lys Val Val Ser Met Thr Asp Ile Thr Asn Gln Lys Ala Glu Leu Gln
465                 470                 475                 480

Ala Ile Asn Leu Ala Leu Gln Asp Ser Gly Leu Glu Val Asn Ile Val
                485                 490                 495

Thr Asp Ser Gln Tyr Ala Leu Gly Ile Ile Gln Ala Gln Pro Asp Lys
            500                 505                 510

Ser Glu Ser Glu Leu Val Ser Gln Ile Ile Glu Gln Leu Ile Lys Lys
        515                 520                 525

Glu Lys Val Tyr Leu Ser Trp Val Pro Ala His Lys Gly Ile Gly Gly
    530                 535                 540

Asn Glu Gln Val Asp Lys Leu Val Ser Asn Gly Ile Arg Lys Ile Leu
545                 550                 555                 560

<210> SEQ ID NO 5
<211> LENGTH: 560
<212> TYPE: PRT
<213> ORGANISM: Human immunodeficiency virus type 1

<400> SEQUENCE: 5

Pro Ile Ser Pro Ile Asp Thr Val Pro Val Lys Leu Lys Pro Gly Met
1               5                   10                  15

Asp Gly Pro Lys Val Lys Gln Trp Pro Leu Thr Glu Glu Lys Ile Lys
            20                  25                  30

Ala Leu Thr Glu Ile Cys Lys Glu Met Glu Glu Glu Gly Lys Ile Ser
        35                  40                  45

Lys Ile Gly Pro Glu Asn Pro Tyr Asn Thr Pro Val Phe Ala Ile Lys
    50                  55                  60

Lys Lys Asp Ser Thr Lys Trp Arg Lys Leu Val Asp Phe Arg Glu Leu
65                  70                  75                  80

Asn Lys Arg Thr Gln Asp Phe Trp Glu Val Gln Leu Gly Ile Pro His
                85                  90                  95

Pro Ala Gly Leu Lys Lys Lys Ser Val Thr Val Leu Asp Val Gly
            100                 105                 110

Asp Ala Tyr Phe Ser Val Pro Leu Asp Glu Ser Phe Arg Lys Tyr Thr
        115                 120                 125

Ala Phe Thr Ile Pro Ser Ile Asn Asn Glu Thr Pro Gly Ile Arg Tyr
    130                 135                 140

Gln Tyr Asn Val Leu Pro Gln Gly Trp Lys Gly Ser Pro Ala Ile Phe
145                 150                 155                 160

Gln Ser Ser Met Thr Lys Ile Leu Glu Pro Phe Arg Ile Lys Asn Pro
                165                 170                 175

Glu Met Val Ile Tyr Gln Tyr Met Asp Asp Leu Tyr Val Gly Ser Asp
            180                 185                 190

Leu Glu Ile Gly Gln His Arg Thr Lys Ile Glu Glu Leu Arg Ala His
        195                 200                 205

Leu Leu Ser Trp Gly Phe Thr Thr Pro Asp Lys Lys His Gln Lys Glu
    210                 215                 220

Pro Pro Phe Leu Trp Met Gly Tyr Glu Leu His Pro Asp Arg Trp Thr
225                 230                 235                 240

Val Gln Pro Ile Glu Leu Pro Glu Lys Asp Ser Trp Thr Val Asn Asp
                245                 250                 255

Ile Gln Lys Leu Val Gly Lys Leu Asn Trp Ala Ser Gln Ile Tyr Ala
            260                 265                 270

Gly Ile Lys Val Lys Gln Leu Cys Lys Leu Leu Arg Gly Thr Lys Ala
        275                 280                 285
```

```
Leu Thr Asp Ile Val Pro Leu Thr Glu Glu Ala Glu Leu Glu Leu Glu
    290                 295                 300

Glu Asn Arg Glu Ile Leu Arg Ile Pro Val His Gly Val Tyr Tyr Asp
305                 310                 315                 320

Pro Ser Lys Asp Leu Val Ala Glu Val Gln Lys Gln Gly Gln Asp Gln
                325                 330                 335

Trp Thr Tyr Gln Ile Tyr Gln Glu Pro Phe Lys Asn Leu Lys Thr Gly
                340                 345                 350

Lys Tyr Ser Arg Lys Arg Ser Ala His Thr Asn Asp Val Arg Gln Leu
            355                 360                 365

Thr Glu Val Val Gln Lys Ile Ala Thr Glu Ser Ile Val Ile Trp Gly
    370                 375                 380

Lys Thr Pro Lys Phe Arg Leu Pro Ile Gln Arg Glu Thr Trp Glu Thr
385                 390                 395                 400

Trp Trp Met Glu Tyr Trp Gln Ala Thr Trp Ile Pro Glu Trp Glu Phe
                405                 410                 415

Val Asn Thr Pro Pro Leu Val Lys Leu Trp Tyr Gln Leu Glu Lys Asp
                420                 425                 430

Pro Ile Val Gly Ala Glu Thr Phe Tyr Val Asp Gly Ala Ala Ser Arg
            435                 440                 445

Glu Thr Lys Leu Gly Lys Ala Gly Tyr Val Thr Asp Arg Gly Arg Gln
    450                 455                 460

Lys Val Ile Ser Leu Thr Glu Thr Thr Asn Gln Lys Thr Glu Leu His
465                 470                 475                 480

Ala Ile His Leu Ala Leu Gln Asp Ser Gly Ser Glu Val Asn Ile Val
                485                 490                 495

Thr Asp Ser Gln Tyr Ala Leu Gly Ile Ile Gln Ala Gln Pro Asp Arg
            500                 505                 510

Ser Glu Ser Glu Val Val Ser Gln Ile Ile Glu Glu Leu Ile Lys Lys
    515                 520                 525

Glu Lys Val Tyr Leu Ser Trp Val Pro Ala His Lys Gly Ile Gly Gly
    530                 535                 540

Asn Glu Gln Val Asp Lys Leu Val Ser Gly Ile Arg Lys Val Leu
545                 550                 555                 560

<210> SEQ ID NO 6
<211> LENGTH: 560
<212> TYPE: PRT
<213> ORGANISM: Human immunodeficiency virus type 1

<400> SEQUENCE: 6

Pro Ile Ser Pro Ile Glu Thr Val Pro Val Lys Leu Lys Pro Gly Met
1               5                   10                  15

Asp Gly Pro Lys Val Lys Gln Trp Pro Leu Thr Glu Glu Lys Ile Lys
                20                  25                  30

Ala Leu Thr Ala Ile Cys Asp Glu Met Glu Lys Glu Gly Lys Ile Thr
            35                  40                  45

Lys Ile Gly Pro Glu Asn Pro Tyr Asn Thr Pro Ile Phe Ala Ile Lys
    50                  55                  60

Lys Lys Asp Ser Thr Lys Trp Arg Lys Leu Val Asp Phe Arg Glu Leu
65                  70                  75                  80

Asn Lys Arg Thr Gln Asp Phe Trp Glu Val Gln Leu Gly Ile Pro His
                85                  90                  95

Pro Ala Gly Leu Lys Arg Lys Lys Ser Val Thr Val Leu Asp Val Gly
            100                 105                 110
```

```
Asp Ala Tyr Phe Ser Val Pro Leu Tyr Glu Asp Phe Arg Lys Tyr Thr
            115                 120                 125

Ala Phe Thr Ile Pro Ser Thr Asn Asn Glu Thr Pro Gly Ile Arg Tyr
        130                 135                 140

Gln Tyr Asn Val Leu Pro Gln Gly Trp Lys Gly Ser Pro Ala Ile Phe
145                 150                 155                 160

Gln Ser Ser Met Thr Lys Ile Leu Glu Pro Phe Arg Lys Gln Asn Pro
                165                 170                 175

Asp Ile Val Ile Tyr Gln Tyr Met Asp Asp Leu Tyr Val Gly Ser Asp
            180                 185                 190

Leu Glu Ile Gly Gln His Arg Thr Lys Ile Glu Leu Arg Gln His
        195                 200                 205

Leu Leu Arg Trp Gly Phe Thr Thr Pro Asp Lys Lys His Gln Lys Glu
210                 215                 220

Pro Pro Phe Leu Trp Met Gly Tyr Glu Leu His Pro Asp Lys Trp Thr
225                 230                 235                 240

Val Gln Pro Ile Gln Leu Pro Glu Lys Asp Ser Trp Thr Val Asn Asp
                245                 250                 255

Ile Gln Lys Leu Val Gly Lys Leu Asn Trp Ala Ser Gln Ile Tyr Pro
            260                 265                 270

Gly Ile Lys Val Arg Gln Leu Cys Lys Leu Leu Arg Gly Ala Lys Ala
        275                 280                 285

Leu Thr Asp Ile Val Pro Leu Thr Glu Glu Ala Glu Leu Glu Leu Ala
290                 295                 300

Glu Asn Arg Glu Ile Leu Lys Glu Pro Val His Gly Ile Tyr Tyr Asp
305                 310                 315                 320

Pro Ser Lys Asp Leu Ile Ala Glu Ile Gln Lys Gln Gly Gln Asp Gln
                325                 330                 335

Trp Thr Tyr Gln Ile Tyr Gln Glu Pro Phe Lys Asn Leu Lys Thr Gly
            340                 345                 350

Lys Tyr Ala Lys Met Arg Thr Ala His Thr Asn Asp Val Lys Gln Leu
        355                 360                 365

Thr Glu Ala Val Gln Lys Ile Ala Met Glu Ser Ile Val Ile Trp Gly
370                 375                 380

Lys Thr Pro Lys Phe Arg Leu Pro Ile Gln Lys Glu Thr Trp Glu Ile
385                 390                 395                 400

Trp Trp Thr Asp Tyr Trp Gln Ala Thr Trp Ile Pro Glu Trp Glu Phe
                405                 410                 415

Val Asn Thr Pro Pro Leu Val Lys Leu Trp Tyr Gln Leu Glu Lys Asp
            420                 425                 430

Pro Ile Val Gly Val Glu Thr Phe Tyr Val Asp Gly Ala Ala Asn Arg
        435                 440                 445

Glu Thr Lys Ile Gly Lys Ala Gly Tyr Val Thr Asp Arg Gly Arg Lys
450                 455                 460

Lys Val Val Ser Leu Thr Glu Thr Thr Asn Gln Lys Thr Glu Leu His
465                 470                 475                 480

Ala Ile Cys Ile Ala Leu Gln Asp Ser Gly Ser Glu Val Asn Ile Val
                485                 490                 495

Thr Asp Ser Gln Tyr Ala Leu Gly Ile Ile Gln Ala Gln Pro Asp Lys
            500                 505                 510

Ser Glu Ser Glu Leu Val Asn Gln Ile Ile Glu Gln Leu Ile Lys Lys
        515                 520                 525

Glu Arg Val Tyr Leu Ser Trp Val Pro Ala His Lys Gly Ile Gly Gly
530                 535                 540
```

```
Asn Glu Gln Val Asp Lys Leu Val Ser Ser Gly Ile Arg Lys Val Leu
545                 550                 555                 560

<210> SEQ ID NO 7
<211> LENGTH: 559
<212> TYPE: PRT
<213> ORGANISM: Human immunodeficiency virus type 1

<400> SEQUENCE: 7

Pro Val Ala Arg Ile Glu Pro Val Lys Val Gln Leu Lys Pro Glu Lys
1               5                   10                  15

Asp Gly Pro Lys Ile Arg Gln Trp Pro Leu Ser Lys Glu Lys Ile Leu
            20                  25                  30

Ala Leu Lys Glu Ile Cys Glu Lys Met Glu Lys Glu Gly Gln Leu Glu
        35                  40                  45

Glu Ala Pro Pro Thr Asn Pro Tyr Asn Ser Pro Thr Phe Ala Ile Lys
    50                  55                  60

Lys Lys Asp Lys Asn Lys Trp Arg Met Leu Ile Asp Phe Arg Glu Leu
65                  70                  75                  80

Asn Lys Val Thr Gln Glu Phe Thr Glu Val Gln Leu Gly Ile Pro His
                85                  90                  95

Pro Ala Gly Leu Ala Ser Lys Lys Arg Ile Thr Val Leu Asp Val Gly
            100                 105                 110

Asp Ala Tyr Phe Ser Val Pro Leu Asp Pro Asp Phe Arg Gln Tyr Thr
        115                 120                 125

Ala Phe Thr Leu Pro Ala Val Asn Asn Ala Glu Pro Gly Lys Arg Tyr
    130                 135                 140

Leu Tyr Lys Val Leu Pro Gln Gly Trp Lys Gly Ser Pro Ala Ile Phe
145                 150                 155                 160

Gln Tyr Thr Met Ala Lys Val Leu Asp Pro Phe Arg Lys Ala Asn Asn
                165                 170                 175

Asp Val Thr Ile Ile Gln Tyr Met Asp Asp Ile Leu Val Ala Ser Asp
            180                 185                 190

Arg Ser Asp Leu Glu His Asp Arg Val Val Ser Gln Leu Lys Glu Leu
        195                 200                 205

Leu Asn Asn Met Gly Phe Ser Thr Pro Glu Glu Lys Phe Gln Lys Asp
    210                 215                 220

Pro Pro Phe Lys Trp Met Gly Tyr Glu Leu Trp Pro Lys Lys Trp Lys
225                 230                 235                 240

Leu Gln Lys Ile Gln Leu Pro Glu Lys Glu Val Trp Thr Val Asn Asp
                245                 250                 255

Ile Gln Lys Leu Val Gly Val Leu Asn Trp Ala Ala Gln Leu Phe Pro
            260                 265                 270

Gly Ile Lys Thr Arg His Ile Cys Lys Leu Ile Arg Gly Lys Met Thr
        275                 280                 285

Leu Thr Glu Glu Val Gln Trp Thr Glu Leu Ala Glu Ala Glu Phe Gln
    290                 295                 300

Glu Asn Lys Ile Ile Leu Glu Gln Glu Gln Gly Ser Tyr Tyr Lys
305                 310                 315                 320

Glu Gly Val Pro Leu Glu Ala Thr Val Gln Lys Asn Leu Ala Asn Gln
                325                 330                 335

Trp Thr Tyr Lys Ile His Gln Gly Asp Lys Ile Leu Lys Val Gly Lys
            340                 345                 350

Tyr Ala Lys Val Lys Asn Thr His Thr Asn Gly Val Arg Leu Leu Ala
        355                 360                 365
```

```
His Val Gln Lys Ile Gly Lys Glu Ala Leu Val Ile Trp Gly Glu
    370             375                 380
Ile Pro Met Phe His Leu Pro Val Glu Arg Glu Thr Trp Asp Gln Trp
385                 390                 395                 400
Trp Thr Asp Tyr Trp Gln Val Thr Trp Ile Pro Glu Trp Asp Phe Val
                405                 410                 415
Ser Thr Pro Pro Leu Ile Arg Leu Ala Tyr Asn Leu Val Lys Asp Pro
            420                 425                 430
Leu Glu Gly Val Glu Thr Tyr Tyr Thr Asp Gly Ser Cys Asn Lys Ala
        435                 440                 445
Ser Lys Glu Gly Lys Ala Gly Tyr Val Thr Asp Arg Gly Lys Asp Lys
    450                 455                 460
Val Lys Pro Leu Glu Gln Thr Thr Asn Gln Gln Ala Glu Leu Glu Ala
465                 470                 475                 480
Phe Ala Leu Ala Leu Gln Asp Ser Gly Pro Gln Val Asn Ile Ile Val
                485                 490                 495
Asp Ser Gln Tyr Val Met Gly Ile Val Ala Ala Gln Pro Thr Glu Thr
            500                 505                 510
Glu Ser Pro Ile Val Arg Glu Ile Ile Glu Glu Met Ile Lys Lys Glu
        515                 520                 525
Lys Ile Tyr Val Gly Trp Val Pro Ala His Lys Gly Leu Gly Gly Asn
    530                 535                 540
Gln Glu Val Asp His Leu Val Ser Gln Gly Ile Arg Gln Ile Leu
545                 550                 555

<210> SEQ ID NO 8
<211> LENGTH: 560
<212> TYPE: PRT
<213> ORGANISM: Human immunodeficiency virus type 2

<400> SEQUENCE: 8

Pro Ile Ser Pro Ile Ala Pro Val Pro Val Lys Leu Lys Pro Gly Met
1               5                   10                  15
Asp Gly Pro Lys Val Lys Gln Trp Pro Leu Ser Arg Glu Lys Ile Glu
            20                  25                  30
Ala Leu Thr Ala Ile Cys Gln Glu Met Glu Gln Glu Gly Lys Ile Ser
        35                  40                  45
Arg Ile Gly Pro Glu Asn Pro Tyr Asn Thr Pro Ile Phe Ala Ile Lys
    50                  55                  60
Lys Lys Asp Ser Thr Lys Trp Arg Lys Leu Val Asp Phe Arg Glu Leu
65                  70                  75                  80
Asn Lys Arg Thr Gln Asp Phe Trp Glu Val Gln Leu Gly Ile Pro His
                85                  90                  95
Pro Gly Gly Leu Lys Gln Arg Gln Ser Val Thr Val Leu Asp Val Gly
            100                 105                 110
Asp Ala Tyr Phe Ser Cys Pro Leu Asp Pro Asp Phe Arg Lys Tyr Thr
        115                 120                 125
Ala Phe Thr Ile Pro Ser Val Asn Asn Glu Thr Pro Gly Val Arg Tyr
    130                 135                 140
Gln Tyr Asn Val Leu Pro Gln Gly Trp Lys Gly Ser Pro Ala Ile Phe
145                 150                 155                 160
Gln Ser Ser Met Thr Lys Ile Leu Asp Pro Phe Arg Lys Ser Asn Pro
                165                 170                 175
Glu Val Glu Ile Tyr Gln Tyr Ile Asp Asp Leu Tyr Val Gly Ser Asp
            180                 185                 190
```

```
Leu Pro Leu Ala Glu His Arg Lys Arg Val Glu Leu Arg Glu His
            195                 200                 205
Leu Tyr Gln Trp Gly Phe Thr Thr Pro Asp Lys Lys His Gln Lys Glu
    210                 215                 220
Pro Pro Phe Leu Trp Met Gly Tyr Glu Leu His Pro Asp Lys Trp Thr
225                 230                 235                 240
Val Gln Pro Ile Gln Leu Pro Asp Lys Glu Val Trp Thr Val Asn Asp
                245                 250                 255
Ile Gln Lys Leu Val Gly Lys Leu Asn Trp Ala Ser Gln Ile Tyr Gln
        260                 265                 270
Gly Ile Arg Val Lys Glu Leu Cys Lys Leu Ile Arg Gly Thr Lys Ser
    275                 280                 285
Leu Thr Glu Val Val Pro Leu Ser Lys Glu Ala Glu Leu Glu Leu Glu
290                 295                 300
Glu Asn Arg Glu Lys Leu Lys Glu Pro Val His Gly Val Tyr Tyr Gln
305                 310                 315                 320
Pro Asp Lys Asp Leu Trp Val Ser Ile Gln Lys His Gly Glu Gly Gln
                325                 330                 335
Trp Thr Tyr Gln Val Tyr Gln Asp Glu His Lys Asn Leu Lys Thr Gly
        340                 345                 350
Lys Tyr Ala Arg Gln Lys Ala Ser His Thr Asn Asp Ile Arg Gln Leu
    355                 360                 365
Ala Glu Val Val Gln Lys Val Ser Gln Glu Ala Ile Val Ile Trp Gly
370                 375                 380
Lys Leu Pro Lys Phe Arg Leu Pro Val Thr Arg Glu Thr Trp Glu Thr
385                 390                 395                 400
Trp Trp Ala Glu Tyr Trp Gln Ala Thr Trp Ile Pro Glu Trp Glu Phe
                405                 410                 415
Val Ser Thr Pro Pro Leu Ile Lys Leu Trp Tyr Gln Leu Glu Thr Glu
        420                 425                 430
Pro Ile Val Gly Ala Glu Thr Phe Tyr Val Asp Gly Ala Ala Asn Arg
    435                 440                 445
Asn Thr Lys Leu Gly Lys Ala Gly Tyr Val Thr Glu Gln Gly Lys Gln
450                 455                 460
Asn Ile Ile Lys Leu Glu Glu Thr Thr Asn Gln Lys Ala Glu Leu Met
465                 470                 475                 480
Ala Val Leu Ile Ala Leu Gln Asp Ser Lys Glu Gln Val Asn Ile Val
                485                 490                 495
Thr Asp Ser Gln Tyr Val Leu Gly Ile Ile Ser Ser Gln Pro Thr Gln
        500                 505                 510
Ser Asp Ser Pro Ile Val Gln Gln Ile Ile Glu Glu Leu Thr Lys Lys
    515                 520                 525
Glu Arg Val Tyr Leu Thr Trp Val Pro Ala His Lys Gly Ile Gly Gly
530                 535                 540
Asn Glu Lys Ile Asp Lys Leu Val Ser Lys Asp Ile Arg Arg Val Leu
545                 550                 555                 560

<210> SEQ ID NO 9
<211> LENGTH: 560
<212> TYPE: PRT
<213> ORGANISM: Simian immunodeficiency virus

<400> SEQUENCE: 9

Pro Ile Ser Pro Ile Glu Val Val Lys Val Gln Leu Lys Glu Gly Met
1               5                   10                  15
```

-continued

Asp Gly Pro Lys Val Lys Gln Trp Pro Leu Ser Lys Glu Lys Ile Glu
            20                  25                  30

Ala Leu Thr Glu Ile Cys Lys Thr Leu Glu Lys Glu Gly Lys Ile Ser
        35                  40                  45

Ala Val Gly Pro Glu Asn Pro Tyr Asn Thr Pro Ile Phe Ala Ile Lys
    50                  55                  60

Lys Lys Asp Thr Ser Lys Trp Arg Lys Leu Val Asp Phe Arg Glu Leu
65                  70                  75                  80

Asn Lys Arg Thr Gln Asp Phe Trp Glu Leu Gln Leu Gly Ile Pro His
                85                  90                  95

Pro Ala Gly Leu Arg Lys Arg Asn Met Val Thr Val Leu Asp Val Gly
            100                 105                 110

Asp Ala Tyr Phe Ser Ile Pro Leu Asp Pro Asp Phe Arg Lys Tyr Thr
        115                 120                 125

Ala Phe Thr Ile Pro Ser Leu Asn Asn Asn Thr Pro Gly Lys Arg Phe
    130                 135                 140

Gln Tyr Asn Val Leu Pro Gln Gly Trp Lys Gly Ser Pro Ala Ile Phe
145                 150                 155                 160

Gln Ser Ser Met Thr Lys Ile Leu Asp Pro Phe Arg Lys Glu His Pro
                165                 170                 175

Asp Val Asp Ile Tyr Gln Tyr Met Asp Asp Leu Tyr Ile Gly Ser Asp
            180                 185                 190

Leu Asn Glu Glu Glu His Arg Lys Leu Ile Lys Lys Leu Arg Gln His
        195                 200                 205

Leu Leu Thr Trp Gly Leu Glu Thr Pro Asp Lys Lys Tyr Gln Glu Lys
    210                 215                 220

Pro Pro Phe Met Trp Met Gly Tyr Glu Leu His Pro Asn Lys Trp Thr
225                 230                 235                 240

Val Gln Asn Ile Thr Leu Pro Glu Pro Glu Gln Trp Thr Val Asn His
                245                 250                 255

Ile Gln Lys Leu Val Gly Lys Leu Asn Trp Ala Ser Gln Ile Tyr His
            260                 265                 270

Gly Ile Lys Thr Lys Glu Leu Cys Lys Leu Ile Arg Gly Val Lys Gly
        275                 280                 285

Leu Thr Glu Pro Val Glu Met Thr Arg Glu Ala Glu Leu Glu Leu Glu
    290                 295                 300

Glu Asn Lys Gln Ile Leu Lys Glu Lys Val Gln Gly Ala Tyr Tyr Asp
305                 310                 315                 320

Pro Lys Leu Pro Leu Gln Ala Ala Ile Gln Lys Gln Gly Gln Gly Gln
                325                 330                 335

Trp Thr Tyr Gln Ile Tyr Gln Glu Glu Gly Lys Asn Leu Lys Thr Gly
            340                 345                 350

Lys Tyr Ala Lys Ser Pro Gly Thr His Thr Asn Glu Ile Arg Gln Leu
        355                 360                 365

Ala Gly Leu Ile Gln Lys Ile Gly Asn Glu Ser Ile Ile Trp Gly
    370                 375                 380

Ile Val Pro Lys Phe Leu Leu Pro Val Ser Lys Glu Thr Trp Ser Gln
385                 390                 395                 400

Trp Trp Thr Asp Tyr Trp Gln Val Thr Trp Pro Glu Trp Glu Phe
                405                 410                 415

Ile Asn Thr Pro Pro Leu Ile Arg Leu Trp Tyr Asn Leu Leu Ser Asp
            420                 425                 430

Pro Ile Pro Glu Ala Glu Thr Phe Tyr Val Asp Gly Ala Ala Asn Arg

```
                435              440              445
Asp Ser Lys Lys Gly Arg Ala Gly Tyr Val Thr Asn Arg Gly Arg Tyr
    450              455              460

Arg Ser Lys Asp Leu Glu Asn Thr Thr Asn Gln Gln Ala Glu Leu Trp
465              470              475              480

Ala Val Asp Leu Ala Leu Lys Asp Ser Gly Ala Gln Val Asn Ile Val
            485              490              495

Thr Asp Ser Gln Tyr Val Met Gly Val Leu Gly Leu Pro Asp Gln
        500              505              510

Ser Asp Ser Pro Ile Val Glu Gln Ile Ile Gln Lys Leu Thr Gln Lys
        515              520              525

Thr Ala Ile Tyr Leu Ala Trp Val Pro Ala His Lys Gly Ile Gly Gly
    530              535              540

Asn Glu Glu Val Asp Lys Leu Val Ser Lys Asn Ile Arg Lys Ile Leu
545              550              555              560

<210> SEQ ID NO 10
<211> LENGTH: 80
<212> TYPE: DNA
<213> ORGANISM: Artificial Sequence
<220> FEATURE:
<223> OTHER INFORMATION: completely synthesized as part of library

<400> SEQUENCE: 10
atccgcctga ttagcgatac tcaggcgccg ggggggtggg aatacagtga tcagcgactt      60
gagcaaaatc acctgcaggg                                                  80

<210> SEQ ID NO 11
<211> LENGTH: 80
<212> TYPE: DNA
<213> ORGANISM: Artificial Sequence
<220> FEATURE:
<223> OTHER INFORMATION: completely synthesized as part of library

<400> SEQUENCE: 11
atccgcctga ttagcgatac tcaggccttg ggcgggccgg gacaatggag agatttactt      60
gagcaaaatc acctgcaggg                                                  80

<210> SEQ ID NO 12
<211> LENGTH: 80
<212> TYPE: DNA
<213> ORGANISM: Artificial Sequence
<220> FEATURE:
<223> OTHER INFORMATION: completely synthesized as part of library

<400> SEQUENCE: 12
atccgcctga ttagcgatac tcaggcgtta gggaagggcg tcgaaagcag ggtgggactt      60
gagcaaaatc acctgcaggg                                                  80

<210> SEQ ID NO 13
<211> LENGTH: 55
<212> TYPE: DNA
<213> ORGANISM: Artificial Sequence
<220> FEATURE:
<223> OTHER INFORMATION: completely synthesized as part of library

<400> SEQUENCE: 13
atccgcctga ttagcgatac tcaggcgtta gggaagggta gcgatacagg gtggg           55

<210> SEQ ID NO 14
<211> LENGTH: 53
```

```
<212> TYPE: DNA
<213> ORGANISM: Artificial Sequence
<220> FEATURE:
<223> OTHER INFORMATION: completely synthesized as part of library

<400> SEQUENCE: 14
cgcctgatta gcgatactca ggcgttaggg aagggcgtcg aaagcagggt ggg            53

<210> SEQ ID NO 15
<211> LENGTH: 41
<212> TYPE: DNA
<213> ORGANISM: Artificial Sequence
<220> FEATURE:
<223> OTHER INFORMATION: completely synthesized as part of library

<400> SEQUENCE: 15
cgcctgatta gcgatactca ggcgttgggt gggtgggtgg g                        41

<210> SEQ ID NO 16
<211> LENGTH: 44
<212> TYPE: DNA
<213> ORGANISM: Artificial Sequence
<220> FEATURE:
<223> OTHER INFORMATION: completely synthesized as part of library

<400> SEQUENCE: 16
cgcctgatta gcgatactca ggcgttgggt tgggttgggt tggg                     44

<210> SEQ ID NO 17
<211> LENGTH: 50
<212> TYPE: DNA
<213> ORGANISM: Artificial Sequence
<220> FEATURE:
<223> OTHER INFORMATION: completely synthesized as part of library

<400> SEQUENCE: 17
cgcctgatta gcgatactca ggcgttgggt tttgggtttt gggttttggg               50

<210> SEQ ID NO 18
<211> LENGTH: 62
<212> TYPE: DNA
<213> ORGANISM: Artificial Sequence
<220> FEATURE:
<223> OTHER INFORMATION: completely synthesized as part of library

<400> SEQUENCE: 18
cgcctgatta gcgatactca ggcgttgggt tttttttggg tttttttttgg gtttttttg    60 gg                                                                   62

<210> SEQ ID NO 19
<211> LENGTH: 41
<212> TYPE: DNA
<213> ORGANISM: Artificial Sequence
<220> FEATURE:
<223> OTHER INFORMATION: completely synthesized as part of library

<400> SEQUENCE: 19
cgcctgatta gcgatactca ggcgttggga gggagggagg g                        41

<210> SEQ ID NO 20
<211> LENGTH: 44
<212> TYPE: DNA
<213> ORGANISM: Artificial Sequence
<220> FEATURE:
<223> OTHER INFORMATION: completely synthesized as part of library

<400> SEQUENCE: 20
```
cgcctgatta gcgatactca ggcgttggga agggaaggga aggg       44

<210> SEQ ID NO 21
<211> LENGTH: 50
<212> TYPE: DNA
<213> ORGANISM: Artificial Sequence
<220> FEATURE:
<223> OTHER INFORMATION: completely synthesized as part of library

<400> SEQUENCE: 21
cgcctgatta gcgatactca ggcgttggga aagggaaaa gggaaaaggg       50

<210> SEQ ID NO 22
<211> LENGTH: 62
<212> TYPE: DNA
<213> ORGANISM: Artificial Sequence
<220> FEATURE:
<223> OTHER INFORMATION: completely synthesized as part of library

<400> SEQUENCE: 22
cgcctgatta gcgatactca ggcgttggga aaaaaaggg aaaaaaagg gaaaaaaaag       60 gg       62

<210> SEQ ID NO 23
<211> LENGTH: 41
<212> TYPE: DNA
<213> ORGANISM: Artificial Sequence
<220> FEATURE:
<223> OTHER INFORMATION: completely synthesized as part of library

<400> SEQUENCE: 23
cgcctgatta gcgatactca ggcgttgggc gggcgggcgg g       41

<210> SEQ ID NO 24
<211> LENGTH: 44
<212> TYPE: DNA
<213> ORGANISM: Artificial Sequence
<220> FEATURE:
<223> OTHER INFORMATION: completely synthesized as part of library

<400> SEQUENCE: 24
cgcctgatta gcgatactca ggcgttgggc cgggccgggc cggg       44

<210> SEQ ID NO 25
<211> LENGTH: 50
<212> TYPE: DNA
<213> ORGANISM: Artificial Sequence
<220> FEATURE:
<223> OTHER INFORMATION: completely synthesized as part of library

<400> SEQUENCE: 25
cgcctgatta gcgatactca ggcgttgggc cccgggcccc gggccccggg       50

<210> SEQ ID NO 26
<211> LENGTH: 39
<212> TYPE: DNA
<213> ORGANISM: Artificial Sequence
<220> FEATURE:
<223> OTHER INFORMATION: completely synthesized as part of library
<220> FEATURE:
<221> NAME/KEY: misc_binding
<222> LOCATION: (29)..(30)
<223> OTHER INFORMATION: HEXAETHYLENE GLYCOL
<220> FEATURE:
<221> NAME/KEY: misc_binding
<222> LOCATION: (32)..(33)
<223> OTHER INFORMATION: HEXAETHYLENE GLYCOL

```
<220> FEATURE:
<221> NAME/KEY: misc_binding
<222> LOCATION: (35)..(36)
<223> OTHER INFORMATION: HEXAETHYLENE GLYCOL

<400> SEQUENCE: 26
cgcctgatta gcgatactca ggcgttgggg ggggggggg                          39

<210> SEQ ID NO 27
<211> LENGTH: 37
<212> TYPE: DNA
<213> ORGANISM: Artificial Sequence
<220> FEATURE:
<223> OTHER INFORMATION: completely synthesized as part of library

<400> SEQUENCE: 27
cgtgattagc gatactcacg ttgggtgggt gggtggg                            37

<210> SEQ ID NO 28
<211> LENGTH: 35
<212> TYPE: DNA
<213> ORGANISM: Artificial Sequence
<220> FEATURE:
<223> OTHER INFORMATION: completely synthesized as part of library

<400> SEQUENCE: 28
cggattagcg atactccgtt gggtgggtgg gtggg                              35

<210> SEQ ID NO 29
<211> LENGTH: 35
<212> TYPE: DNA
<213> ORGANISM: Artificial Sequence
<220> FEATURE:
<223> OTHER INFORMATION: completely synthesized as part of library

<400> SEQUENCE: 29
cgcctgaccc ttcaggcgtt gggtgggtgg gtggg                              35

<210> SEQ ID NO 30
<211> LENGTH: 47
<212> TYPE: DNA
<213> ORGANISM: Artificial Sequence
<220> FEATURE:
<223> OTHER INFORMATION: completely synthesized as part of library

<400> SEQUENCE: 30
atccgcctga ttagcgatac tcagaaggat ttgggtgggt gggtggg                 47

<210> SEQ ID NO 31
<211> LENGTH: 65
<212> TYPE: DNA
<213> ORGANISM: Artificial Sequence
<220> FEATURE:
<223> OTHER INFORMATION: completely synthesized as part of library

<400> SEQUENCE: 31
cgcctgatta gcgcgcgccg cgttttcgcg gcgcgcgcta ctcaggcgtt gggtgggtgg   60
gtggg                                                              65

<210> SEQ ID NO 32
<211> LENGTH: 41
<212> TYPE: DNA
<213> ORGANISM: Artificial Sequence
<220> FEATURE:
<223> OTHER INFORMATION: completely synthesized as part of library

<400> SEQUENCE: 32
```
ccggactcat agcgattagt ccggttgggt gggtgggtgg g    41

<210> SEQ ID NO 33
<211> LENGTH: 41
<212> TYPE: DNA
<213> ORGANISM: Artificial Sequence
<220> FEATURE:
<223> OTHER INFORMATION: completely synthesized as part of library

<400> SEQUENCE: 33
cgcctgatta gcgatactca ggcgttaggt gggtgggtgg g    41

<210> SEQ ID NO 34
<211> LENGTH: 41
<212> TYPE: DNA
<213> ORGANISM: Artificial Sequence
<220> FEATURE:
<223> OTHER INFORMATION: completely synthesized as part of library

<400> SEQUENCE: 34
cgcctgatta gcgatactca ggcgttgagt gggtgggtgg g    41

<210> SEQ ID NO 35
<211> LENGTH: 41
<212> TYPE: DNA
<213> ORGANISM: Artificial Sequence
<220> FEATURE:
<223> OTHER INFORMATION: completely synthesized as part of library

<400> SEQUENCE: 35
cgcctgatta gcgatactca ggcgttggat gggtgggtgg g    41

<210> SEQ ID NO 36
<211> LENGTH: 41
<212> TYPE: DNA
<213> ORGANISM: Artificial Sequence
<220> FEATURE:
<223> OTHER INFORMATION: completely synthesized as part of library

<400> SEQUENCE: 36
cgcctgatta gcgatactca ggcgttgggt aggtgggtgg g    41

<210> SEQ ID NO 37
<211> LENGTH: 41
<212> TYPE: DNA
<213> ORGANISM: Artificial Sequence
<220> FEATURE:
<223> OTHER INFORMATION: completely synthesized as part of library

<400> SEQUENCE: 37
cgcctgatta gcgatactca ggcgttgggt gagtgggtgg g    41

<210> SEQ ID NO 38
<211> LENGTH: 41
<212> TYPE: DNA
<213> ORGANISM: Artificial Sequence
<220> FEATURE:
<223> OTHER INFORMATION: completely synthesized as part of library

<400> SEQUENCE: 38
cgcctgatta gcgatactca ggcgttgggt ggatgggtgg g    41

<210> SEQ ID NO 39
<211> LENGTH: 41
<212> TYPE: DNA
<213> ORGANISM: Artificial Sequence

```
<220> FEATURE:
<223> OTHER INFORMATION: completely synthesized as part of library

<400> SEQUENCE: 39
cgcctgatta gcgatactca ggcgttgggt gggtaggtgg g                    41

<210> SEQ ID NO 40
<211> LENGTH: 41
<212> TYPE: DNA
<213> ORGANISM: Artificial Sequence
<220> FEATURE:
<223> OTHER INFORMATION: completely synthesized as part of library

<400> SEQUENCE: 40
cgcctgatta gcgatactca ggcgttgggt gggtgagtgg g                    41

<210> SEQ ID NO 41
<211> LENGTH: 41
<212> TYPE: DNA
<213> ORGANISM: Artificial Sequence
<220> FEATURE:
<223> OTHER INFORMATION: completely synthesized as part of library

<400> SEQUENCE: 41
cgcctgatta gcgatactca ggcgttgggt gggtggatgg g                    41

<210> SEQ ID NO 42
<211> LENGTH: 41
<212> TYPE: DNA
<213> ORGANISM: Artificial Sequence
<220> FEATURE:
<223> OTHER INFORMATION: completely synthesized as part of library

<400> SEQUENCE: 42
cgcctgatta gcgatactca ggcgttgggt gggtgggtag g                    41

<210> SEQ ID NO 43
<211> LENGTH: 41
<212> TYPE: DNA
<213> ORGANISM: Artificial Sequence
<220> FEATURE:
<223> OTHER INFORMATION: completely synthesized as part of library

<400> SEQUENCE: 43
cgcctgatta gcgatactca ggcgttgggt gggtgggtga g                    41

<210> SEQ ID NO 44
<211> LENGTH: 41
<212> TYPE: DNA
<213> ORGANISM: Artificial Sequence
<220> FEATURE:
<223> OTHER INFORMATION: completely synthesized as part of library

<400> SEQUENCE: 44
cgcctgatta gcgatactca ggcgttgggt gggtgggtgg a                    41

<210> SEQ ID NO 45
<211> LENGTH: 37
<212> TYPE: DNA
<213> ORGANISM: Artificial Sequence
<220> FEATURE:
<223> OTHER INFORMATION: completely synthesized as part of library

<400> SEQUENCE: 45
cgcctgatta gcgatactca ggcgttggtg gtggtgg                         37
```

-continued

```
<210> SEQ ID NO 46
<211> LENGTH: 45
<212> TYPE: DNA
<213> ORGANISM: Artificial Sequence
<220> FEATURE:
<223> OTHER INFORMATION: completely synthesized as part of library

<400> SEQUENCE: 46
cgcctgatta gcgatactca ggcgttgggg tggggtgggg tgggg            45

<210> SEQ ID NO 47
<211> LENGTH: 24
<212> TYPE: DNA
<213> ORGANISM: Artificial Sequence
<220> FEATURE:
<223> OTHER INFORMATION: completely synthesized as part of library

<400> SEQUENCE: 47
cgcctgatta gcgatactca ggcg                                   24

<210> SEQ ID NO 48
<211> LENGTH: 16
<212> TYPE: DNA
<213> ORGANISM: Artificial Sequence
<220> FEATURE:
<223> OTHER INFORMATION: completely synthesized as part of library

<400> SEQUENCE: 48
tgggtgggtg ggtggg                                            16

<210> SEQ ID NO 49
<211> LENGTH: 49
<212> TYPE: DNA
<213> ORGANISM: Artificial Sequence
<220> FEATURE:
<223> OTHER INFORMATION: completely synthesized as part of library

<400> SEQUENCE: 49
cgcgctactc aggcgttggg tgggtgggtg ggttcgcctg attagcgcg         49

<210> SEQ ID NO 50
<211> LENGTH: 57
<212> TYPE: DNA
<213> ORGANISM: Artificial Sequence
<220> FEATURE:
<223> OTHER INFORMATION: completely synthesized as part of library

<400> SEQUENCE: 50
cgcgcgcgct actcaggcgt tgggtgggtg ggtgggttcg cctgattagc gcgcgcg   57

<210> SEQ ID NO 51
<211> LENGTH: 63
<212> TYPE: DNA
<213> ORGANISM: Artificial Sequence
<220> FEATURE:
<223> OTHER INFORMATION: completely synthesized as part of library

<400> SEQUENCE: 51
cgcggcgcgc gctactcagg cgttgggtgg gtgggtgggt tcgcctgatt agcgcgcgcc   60
gcg                                                          63

<210> SEQ ID NO 52
<211> LENGTH: 89
<212> TYPE: DNA
<213> ORGANISM: Artificial Sequence
<220> FEATURE:
<223> OTHER INFORMATION: completely synthesized as part of library
```

```
<400> SEQUENCE: 52
cgcgcgcgcg cgcggcggcg cgcgctactc aggcgttggg tgggtgggtg ggttcgcctg     60
attagcgcgc gccgccgcgc gcgcgcgcg                                       89

<210> SEQ ID NO 53
<211> LENGTH: 42
<212> TYPE: DNA
<213> ORGANISM: Artificial Sequence
<220> FEATURE:
<223> OTHER INFORMATION: completely synthesized as part of library

<400> SEQUENCE: 53
gggtgggttc gcctgattag cgatactcag gcgttgggtg gg                        42

<210> SEQ ID NO 54
<211> LENGTH: 42
<212> TYPE: DNA
<213> ORGANISM: Artificial Sequence
<220> FEATURE:
<223> OTHER INFORMATION: completely synthesized as part of library

<400> SEQUENCE: 54
gggtgggttg cggactcata gcgattagtc cgcttgggtg gg                        42

<210> SEQ ID NO 55
<211> LENGTH: 42
<212> TYPE: DNA
<213> ORGANISM: Artificial Sequence
<220> FEATURE:
<223> OTHER INFORMATION: completely synthesized as part of library

<400> SEQUENCE: 55
gggttcgcct gattagcgat actcaggcgt tgggtgggtg gg                        42

<210> SEQ ID NO 56
<211> LENGTH: 42
<212> TYPE: DNA
<213> ORGANISM: Artificial Sequence
<220> FEATURE:
<223> OTHER INFORMATION: completely synthesized as part of library

<400> SEQUENCE: 56
gggtgggtgg gttcgcctga ttagcgatac tcaggcgttg gg                        42

<210> SEQ ID NO 57
<211> LENGTH: 16
<212> TYPE: DNA
<213> ORGANISM: Artificial Sequence
<220> FEATURE:
<223> OTHER INFORMATION: completely synthesized as part of library

<400> SEQUENCE: 57
ggggtgggag gagggt                                                     16

<210> SEQ ID NO 58
<211> LENGTH: 42
<212> TYPE: DNA
<213> ORGANISM: Artificial Sequence
<220> FEATURE:
<223> OTHER INFORMATION: completely synthesized as part of library

<400> SEQUENCE: 58
cgcctgatta gcgatactca ggcgttgggg tgggaggagg gt                        42
```

```
<210> SEQ ID NO 59
<211> LENGTH: 43
<212> TYPE: DNA
<213> ORGANISM: Artificial Sequence
<220> FEATURE:
<223> OTHER INFORMATION: completely synthesized as part of library

<400> SEQUENCE: 59
cgcctgatta gcgatactca ggcgttttgg gtgggtgggt ggg                43

<210> SEQ ID NO 60
<211> LENGTH: 47
<212> TYPE: DNA
<213> ORGANISM: Artificial Sequence
<220> FEATURE:
<223> OTHER INFORMATION: completely synthesized as part of library

<400> SEQUENCE: 60
cgcctgatta gcgatactca ggcgtttttt ttgggtgggt gggtggg            47

<210> SEQ ID NO 61
<211> LENGTH: 41
<212> TYPE: DNA
<213> ORGANISM: Artificial Sequence
<220> FEATURE:
<223> OTHER INFORMATION: completely synthesized as part of library

<400> SEQUENCE: 61
cgcctgatta gcgatactca ggcgaagggt gggtgggtgg g                  41

<210> SEQ ID NO 62
<211> LENGTH: 55
<212> TYPE: DNA
<213> ORGANISM: Artificial Sequence
<220> FEATURE:
<223> OTHER INFORMATION: completely synthesized as part of library

<400> SEQUENCE: 62
cgcctgatta gcgatactca ggcgtttttt tttttttttt gggtgggtgg gtggg   55

<210> SEQ ID NO 63
<211> LENGTH: 39
<212> TYPE: DNA
<213> ORGANISM: Artificial Sequence
<220> FEATURE:
<223> OTHER INFORMATION: completely synthesized as part of library
<220> FEATURE:
<221> NAME/KEY: misc_binding
<222> LOCATION: (24)..(25)
<223> OTHER INFORMATION: hexaethylene glycol

<400> SEQUENCE: 63
cgcctgatta gcgatactca ggcggggtgg gtgggtggg                     39

<210> SEQ ID NO 64
<211> LENGTH: 18
<212> TYPE: DNA
<213> ORGANISM: Human immunodeficiency virus type 1
<220> FEATURE:
<221> NAME/KEY: misc_binding
<222> LOCATION: (1)..(1)
<223> OTHER INFORMATION: CYANINE DYE

<400> SEQUENCE: 64
gtccctgttc gggcgcca                                            18

<210> SEQ ID NO 65
<211> LENGTH: 60
```

```
<212> TYPE: DNA
<213> ORGANISM: Human immunodeficiency virus type 1

<400> SEQUENCE: 65
aagtagtgtg tgcccgtctg ttgtgtgact ctggtaacta gagatccctc agaccctttt    60

<210> SEQ ID NO 66
<211> LENGTH: 43
<212> TYPE: DNA
<213> ORGANISM: Human immunodeficiency virus type 1
<220> FEATURE:
<221> NAME/KEY: misc_binding
<222> LOCATION: (1)..(1)
<223> OTHER INFORMATION: CYANINE DYE

<400> SEQUENCE: 66
ggucucucug guuagaccag aucugagccu gggagcucuc ugg                      43

<210> SEQ ID NO 67
<211> LENGTH: 53
<212> TYPE: DNA
<213> ORGANISM: Human immunodeficiency virus type 1

<400> SEQUENCE: 67
ccctagttag ccagagagct cccaggctca gatctggtct aaccagagag acc           53

<210> SEQ ID NO 68
<211> LENGTH: 21
<212> TYPE: DNA
<213> ORGANISM: Artificial Sequence
<220> FEATURE:
<223> OTHER INFORMATION: completely synthesized as part of library

<400> SEQUENCE: 68
gggtttgggt ttgggtttgg g                                              21

<210> SEQ ID NO 69
<211> LENGTH: 27
<212> TYPE: DNA
<213> ORGANISM: Artificial Sequence
<220> FEATURE:
<223> OTHER INFORMATION: completely synthesized as part of library

<400> SEQUENCE: 69
gggttttggg gtttttgggt ttttggg                                        27

<210> SEQ ID NO 70
<211> LENGTH: 30
<212> TYPE: DNA
<213> ORGANISM: Artificial Sequence
<220> FEATURE:
<223> OTHER INFORMATION: completely synthesized as part of library

<400> SEQUENCE: 70 gggtttttg ggtttttgg gtttttggg                                        30

<210> SEQ ID NO 71
<211> LENGTH: 33
<212> TYPE: DNA
<213> ORGANISM: Artificial Sequence
<220> FEATURE:
<223> OTHER INFORMATION: completely synthesized as part of library

<400> SEQUENCE: 71
gggttttttt gggtttttt gggtttttt ggg                                   33
```

```
<210> SEQ ID NO 72
<211> LENGTH: 21
<212> TYPE: DNA
<213> ORGANISM: Artificial Sequence
<220> FEATURE:
<223> OTHER INFORMATION: completely synthesized as part of library

<400> SEQUENCE: 72
gggaaaggga aagggaaagg g                                              21

<210> SEQ ID NO 73
<211> LENGTH: 21
<212> TYPE: DNA
<213> ORGANISM: Artificial Sequence
<220> FEATURE:
<223> OTHER INFORMATION: completely synthesized as part of library

<400> SEQUENCE: 73
gggcccgggc ccgggcccgg g                                              21

<210> SEQ ID NO 74
<211> LENGTH: 26
<212> TYPE: DNA
<213> ORGANISM: Artificial Sequence
<220> FEATURE:
<223> OTHER INFORMATION: completely synthesized as part of library

<400> SEQUENCE: 74
gggaagggcg tcgaaagcag ggtggg                                         26

<210> SEQ ID NO 75
<211> LENGTH: 40
<212> TYPE: DNA
<213> ORGANISM: Artificial Sequence
<220> FEATURE:
<223> OTHER INFORMATION: completely synthesized as part of library

<400> SEQUENCE: 75
cgcctgatta gcgatactca ggcgtgggtg ggtgggtggg                          40

<210> SEQ ID NO 76
<211> LENGTH: 40
<212> TYPE: DNA
<213> ORGANISM: Artificial Sequence
<220> FEATURE:
<223> OTHER INFORMATION: completely synthesized as part of library

<400> SEQUENCE: 76
cgcctgatta gcgatactca ggcgagggtg ggtgggtggg                          40

<210> SEQ ID NO 77
<211> LENGTH: 43
<212> TYPE: DNA
<213> ORGANISM: Artificial Sequence
<220> FEATURE:
<223> OTHER INFORMATION: completely synthesized as part of library

<400> SEQUENCE: 77
cgcctgatta gcgatactca ggcgaaaagg gtgggtgggt ggg                      43

<210> SEQ ID NO 78
<211> LENGTH: 47
<212> TYPE: DNA
<213> ORGANISM: Artificial Sequence
<220> FEATURE:
<223> OTHER INFORMATION: completely synthesized as part of library

<400> SEQUENCE: 78
```

```
cgcctgatta gcgatactca ggcgaaaaaa aagggtgggt gggtggg      47
```

<210> SEQ ID NO 79
<211> LENGTH: 51
<212> TYPE: DNA
<213> ORGANISM: Artificial Sequence
<220> FEATURE:
<223> OTHER INFORMATION: completely synthesized as part of library

<400> SEQUENCE: 79

```
cgcctgatta gcgatactca ggcgtttttt tttttgggt gggtgggtgg g      51
```

<210> SEQ ID NO 80
<211> LENGTH: 37
<212> TYPE: DNA
<213> ORGANISM: Artificial Sequence
<220> FEATURE:
<223> OTHER INFORMATION: completely synthesized as part of library

<400> SEQUENCE: 80

```
cgcctgatta gcgatactca ggcgttggtg gtggtgg      37
```

<210> SEQ ID NO 81
<211> LENGTH: 45
<212> TYPE: DNA
<213> ORGANISM: Artificial Sequence
<220> FEATURE:
<223> OTHER INFORMATION: completely synthesized as part of library

<400> SEQUENCE: 81

```
cgcctgatta gcgatactca ggcgttgggg tggggtgggg tgggg      45
```

<210> SEQ ID NO 82
<211> LENGTH: 21
<212> TYPE: DNA
<213> ORGANISM: Artificial Sequence
<220> FEATURE:
<223> OTHER INFORMATION: completely synthesized as part of library

<400> SEQUENCE: 82

```
dgcgggacaa tggagagagg g      21
```

<210> SEQ ID NO 83
<211> LENGTH: 15
<212> TYPE: DNA
<213> ORGANISM: Artificial Sequence
<220> FEATURE:
<223> OTHER INFORMATION: completely synthesized as part of library
<220> FEATURE:
<221> NAME/KEY: MISC_FEATURE
<222> LOCATION: (4)..(4)
<223> OTHER INFORMATION: N = hexaethylene glycol
<220> FEATURE:
<221> NAME/KEY: MISC_FEATURE
<222> LOCATION: (8)..(8)
<223> OTHER INFORMATION: N = hexaethylene glycol
<220> FEATURE:
<221> NAME/KEY: MISC_FEATURE
<222> LOCATION: (12)..(12)
<223> OTHER INFORMATION: N = hexaethylene glycol

<400> SEQUENCE: 83

```
gggngggngg gnggg      15
```

<210> SEQ ID NO 84
<211> LENGTH: 15
<212> TYPE: DNA
<213> ORGANISM: Artificial Sequence

```
<220> FEATURE:
<223> OTHER INFORMATION: completely synthesized as part of library

<400> SEQUENCE: 84
gggtgggtgg gtggg                                                         15

<210> SEQ ID NO 85
<211> LENGTH: 18
<212> TYPE: DNA
<213> ORGANISM: Artificial Sequence
<220> FEATURE:
<223> OTHER INFORMATION: completely synthesized as part of library

<400> SEQUENCE: 85
gggttgggtt gggttggg                                                      18

<210> SEQ ID NO 86
<211> LENGTH: 24
<212> TYPE: DNA
<213> ORGANISM: Artificial Sequence
<220> FEATURE:
<223> OTHER INFORMATION: completely synthesized as part of library

<400> SEQUENCE: 86
gggttttggg ttttgggttt tggg                                               24

<210> SEQ ID NO 87
<211> LENGTH: 36
<212> TYPE: DNA
<213> ORGANISM: Artificial Sequence
<220> FEATURE:
<223> OTHER INFORMATION: completely synthesized as part of library

<400> SEQUENCE: 87
gggttttttt tgggttttttt ttgggttttt tttggg                                 36

<210> SEQ ID NO 88
<211> LENGTH: 15
<212> TYPE: DNA
<213> ORGANISM: Artificial Sequence
<220> FEATURE:
<223> OTHER INFORMATION: completely synthesized as part of library

<400> SEQUENCE: 88
gggagggagg gaggg                                                         15

<210> SEQ ID NO 89
<211> LENGTH: 18
<212> TYPE: DNA
<213> ORGANISM: Artificial Sequence
<220> FEATURE:
<223> OTHER INFORMATION: completely synthesized as part of library

<400> SEQUENCE: 89
gggaagggaa gggaaggg                                                      18

<210> SEQ ID NO 90
<211> LENGTH: 24
<212> TYPE: DNA
<213> ORGANISM: Artificial Sequence
<220> FEATURE:
<223> OTHER INFORMATION: completely synthesized as part of library

<400> SEQUENCE: 90
gggaaaaggg aaagggaaa aggg                                                24
```

```
<210> SEQ ID NO 91
<211> LENGTH: 18
<212> TYPE: DNA
<213> ORGANISM: Artificial Sequence
<220> FEATURE:
<223> OTHER INFORMATION: completely synthesized as part of library

<400> SEQUENCE: 91
gggccgggcc gggccggg                                                 18

<210> SEQ ID NO 92
<211> LENGTH: 24
<212> TYPE: DNA
<213> ORGANISM: Artificial Sequence
<220> FEATURE:
<223> OTHER INFORMATION: completely synthesized as part of library

<400> SEQUENCE: 92
gggccccggg ccccgggccc cggg                                          24

<210> SEQ ID NO 93
<211> LENGTH: 15
<212> TYPE: DNA
<213> ORGANISM: Artificial Sequence
<220> FEATURE:
<223> OTHER INFORMATION: completely synthesized as part of library

<400> SEQUENCE: 93
gggcgggcgg gcggg                                                    15
```